(12) United States Patent
Dack et al.

(10) Patent No.: US 7,045,653 B2
(45) Date of Patent: May 16, 2006

(54) PHARMACEUTICALS

(75) Inventors: Kevin Neil Dack, Sandwich (GB); Robert John Maguire, Groton, CT (US)

(73) Assignee: Pfizer, Inc., New York, NY (US)

( * ) Notice: Subject to any disclaimer, the term of this patent is extended or adjusted under 35 U.S.C. 154(b) by 227 days.

(21) Appl. No.: 10/739,425

(22) Filed: Dec. 18, 2003

(65) Prior Publication Data

US 2005/0075392 A1   Apr. 7, 2005

Related U.S. Application Data

(60) Provisional application No. 60/448,230, filed on Feb. 18, 2003.

(51) Int. Cl.
C07C 229/00 (2006.01)
(52) U.S. Cl. .................. 562/450; 560/121; 560/122
(58) Field of Classification Search ................ 562/450; 560/121, 122
See application file for complete search history.

(56) References Cited

U.S. PATENT DOCUMENTS

| | | | |
|---|---|---|---|
| 4,722,810 A | 2/1988 | Delaney et al. |
| 4,929,641 A | 5/1990 | Haslanger et al. |
| 5,208,236 A | 5/1993 | Neustadt |
| 5,244,889 A | 9/1993 | MacPherson et al. |
| 5,389,610 A | 2/1995 | Neustadt et al. |
| 5,508,272 A | 4/1996 | Robl |
| 5,552,397 A | 9/1996 | Karanewsky et al. |
| 5,672,599 A | 9/1997 | Robl |
| 5,677,297 A | 10/1997 | Waldeck et al. |
| 5,723,457 A | 3/1998 | Karanewsky et al. |
| 5,723,602 A | 3/1998 | Karanewsky et al. |
| 5,783,573 A | 7/1998 | Rozsa et al. |
| 5,859,239 A | 1/1999 | Karanewsky et al. |
| 5,891,912 A | 4/1999 | Kawashima et al. |
| 5,968,980 A | 10/1999 | Kawashima et al. |

FOREIGN PATENT DOCUMENTS

| | | |
|---|---|---|
| EP | 0136883 | 4/1985 |
| EP | 0254032 | 1/1988 |
| EP | 0358398 | 3/1990 |
| EP | 0274234 | 9/1991 |
| EP | 0509442 | 10/1992 |
| EP | 0519738 | 12/1992 |
| EP | 0544620 | 6/1993 |
| EP | 0599444 | 6/1994 |
| EP | 0629627 | 12/1994 |
| EP | 0640594 | 3/1995 |
| EP | 0655461 | 5/1995 |
| EP | 0690070 | 1/1996 |
| EP | 0738711 | 10/1996 |
| EP | 0798291 | 9/2002 |
| JP | (1993)592948 | 4/1993 |
| JP | (1995)7157459 | 6/1995 |
| JP | (1996)841015 | 2/1996 |
| JP | (1996)8245609 | 9/1996 |
| WO | WO 91/07386 | 5/1991 |
| WO | WO 91/13054 | 9/1991 |
| WO | WO 93/09101 | 5/1993 |
| WO | WO 94/15908 | 7/1994 |
| WO | WO 91/08195 | 11/1994 |
| WO | WO 91/09840 | 5/1995 |
| WO | WO 97/24342 | 7/1997 |
| WO | WO 02/03995 | 1/2002 |
| WO | WO 2004/056750 A1 * | 7/2004 |

OTHER PUBLICATIONS

Biochem. Biophys. Res. Commun. vol., 164, p. 58, 1989.
Biochem. Soc. Trans. vol., 21(3), p. 678, 1993.
Bioorg. Med. Chem. Letts. vol., 4(22), p. 2715, 1994.
Bioorg. Med. Chem. Letts. vol., 6(1), p. 65, 1996.
Bioorg. Med. Chem. Letts vol., 11(3), p. 375, 2001.
Bioorg. Med. Chem. Letts vol., 12, p. 3059, 2002.
Cardiovasc. Drug Rev. vol., 9(3), p. 285, 1991.
Cardiovasc. Drug Rev. vol., 12(4), p. 271, 1994.
Cardiovasc. Drug Rev. vol., 14(2), p. 166, 1996.
Chemtracts vol., 10(11), p. 804, 1997.
Clin. Exp. Pharmacol. Physiol. vol., 22(1), p. 63, 1995.
Curr. Opin. Inves. Drugs vol., 2(11), p. 1175, 1993.
Current Pharm. Design vol., 2(5), p. 443, 1996.

(Continued)

Primary Examiner—Cecilia J. Tsang
Assistant Examiner—Hector M. Reyes
(74) Attorney, Agent, or Firm—Cynthia M. Bott; Andrew J. Leon

(57) ABSTRACT

The invention relates to NEP inhibitors for treating cardiovascular disorders. Preferred NEP inhibitors are compounds of formula (I) wherein $R^1$ is $C_1$–$C_6$alkyl, $C_1$–$C_6$alkoxyC$_1$–$C_3$alkyl or $C_1$–$C_6$alkoxyC$_1$–$C_6$alkoxyC$_1$–$C_3$alkyl; $R^2$ is hydrogen or $C_1$–$C_6$alkyl; L is a three atom linkage selected from —CH$_2$—X—CH$_2$— and —CH$_2$—CH$_2$—X— where the right hand side of the linkage is attached to $R^3$ and where X is oxygen, sulfur or methylene; $R^3$ is phenyl or aromatic heterocyclyl, either of which may be independently substituted by one or more groups selected from: $C_1$–$C_6$alkyl, halo, haloC$_1$–$C_6$alkyl, $C_1$–$C_6$alkoxy, haloC$_1$–$C_6$alkoxy, $C_1$–$C_6$alkylthio, haloC$_1$–$C_6$alkylthio and nitrile; and $R^4$ and $R^5$ are either both hydrogen, or one of $R^4$ and $R^5$ is hydrogen and the other is a biolabile ester-forming group that in the body of a patient is replaced by hydrogen.

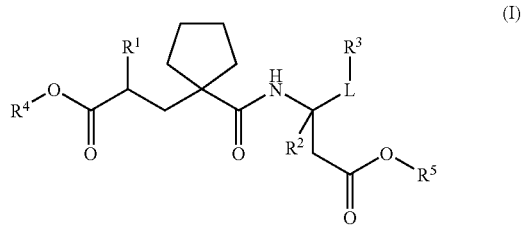

(I)

30 Claims, No Drawings

OTHER PUBLICATIONS

Exp. Opin. Ther. Patents vol., 6(11), p. 1147, 1996.
Gen. Pharmacol. vol., 27(4), p. 581, 1996.
Handbook Exp. Pharmacol. vol., 104(1), p. 547, 1993.
J. Med. Chem. vol., 36(1), p. 87, 1993.
J. Med. Chem. vol., 36(16), p. 2420, 1993.
J. Med. Chem vol., 36(24) p. 3821, 1993.
J. Med. Chem vol., 38(26), p. 5023, 1995.
Pathol. Biol. vol., 46(3), p. 191, 1998.
Perspect. Med. Chem. p. 45, 1993.
Pharmacol. Rev. vol., 45(1), p. 87, 1993.
TiPS vol., 11, p. 245, 1990.
Zinc Metalloproteases Health Dis. p. 105, 1996.

Fournie-Zaluski MC, Gonzalez W, Turcaud S, Pham I, Roques BP, Michel JB, Dual inhibition of angiotensin-converting enzyme and neutral endopeptidase by the orally active inhibitor mixanpril: a potential therapeutic approach in hypertension. Proceedings of the National Academy of Sciences of the United States of America. 91(9):4072-6, Apr. 26, 1994.

Fournie-Zaluski MC, Corie P, Turcaud S, Rousselet N, Gonzalez W, Barbe B, Pham I, Jullian N. Michel JB, Roques BP, New dual inhibitors of neutral endopeptidase and angiotensin-converting enzyme: rational design, bioavailability, and pharmacological responses in experimental hypertension, Journal of Medicinal Chemistry, 37(8):1070-83, Apr. 15, 1994.

* cited by examiner

PHARMACEUTICALS

This application claims the benefit of foreign priority under 35 U.S.C. section 119(a) to United Kingdom provisional patent application No. 0230036.6, filed on Dec. 23, 2002. The present application also claims priority under 35 U.S.C. section 119(e) to U.S. provisional application No. 60/448,230, filed Feb. 18, 2003.

The invention relates to a series of cyclopentyl substituted glutaramide derivatives and compositions and uses thereof. The derivatives are potent and selective inhibitors of neutral endopeptidase (NEP) and may be used to treat a number of diseases and conditions particularly cardiovascular disorders, especially hypertension.

WO91/08195 discloses a series of 3-styryl β-alanine substituted glutaramide derivatives which have inhibitory activity against NEP.

According to a first aspect, the invention provides a compound of formula (I), a pharmaceutically acceptable salt or solvate thereof

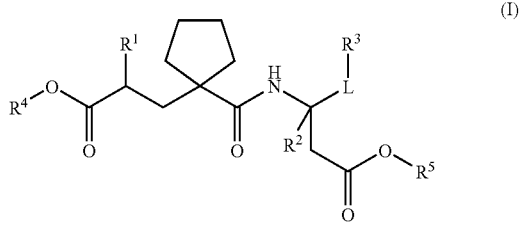

wherein
$R^1$ is $C_1$–$C_6$alkyl, $C_1$–$C_6$alkoxy$C_1$–$C_3$alkyl or $C_1$–$C_6$alkoxy$C_1$–$C_6$alkoxy$C_1$–$C_3$alkyl;
$R^2$ is hydrogen or $C_1$–$C_6$alkyl;
L is a three atom linkage selected from —$CH_2$—X—$CH_2$— and —$CH_2$—$CH_2$—X— where the right hand side of the linkage is attached to $R^3$ and where X is oxygen, sulfur or methylene;
$R^3$ is phenyl or aromatic heterocyclyl, either of which may be independently substituted by one or more groups selected from: $C_1$–$C_6$alkyl, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio and nitrile; and
$R^4$ and $R^5$ are either both hydrogen, or one of $R^4$ and $R^5$ is hydrogen and the other is a biolabile ester-forming group that in the body of a patient is replaced by hydrogen.

Unless otherwise indicated, any alkyl group may be straight or branched and is of 1 to 6 carbon atoms, preferably 1 to 4.

Unless otherwise indicated, any carbocyclyl group contains 3 to 8 ring-atoms, and may be saturated, unsaturated or aromatic. Preferred saturated carbocyclyl groups are cyclopropyl, cyclobutyl, cyclopentyl or cyclohexyl. Preferred unsaturated carbocyclyl groups contain up to 3 double bonds. A preferred aromatic carbocyclyl group is phenyl. The term carbocylic should be similarly construed. In addition, the term carbocyclyl includes any fused combination of carbocyclyl groups, for example naphthyl, phenanthryl, indanyl and indenyl.

Unless otherwise indicated, any heterocyclyl group contains 5 to 7 ring-atoms up to 4 of which may be hetero-atoms such as nitrogen, oxygen and sulfur, and may be saturated, unsaturated or aromatic. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Halo means fluoro, chloro, bromo or iodo.

Unless otherwise indicate, any haloalkyl, haloalkoxy or haloalkylthio group contains one or more halo atoms which halo atoms may be the same or different.

Preferably $R^1$ is $C_1$–$C_6$alkyl or $C_1$–$C_6$alkoxy$C_1$–$C_3$alkyl. More preferably $R^1$ is propyl or methoxyethyl.

Preferably $R^2$ is hydrogen.

Preferably L is a three atom linkage selected from —$CH_2$—O—$CH_2$—, —$CH_2$—$CH_2$—O— and $CH_2$—$CH_2$—$CH_2$—, where the right hand side of the linkage is attached to $R^3$. More preferably L is —$CH_2$—$CH_2$—O— or $CH_2$—$CH_2$—$CH_2$—.

Preferably $R^3$ is phenyl which may be independently substituted by one or more groups selected from: $C_1$–$C_6$alkyl, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio and nitrile. More preferably $R^3$ is phenyl which may be independently substituted by one or more groups selected from: $C_1$–$C_6$ alkyl, halo, halo$C_1$–$C_6$alkyl, $C_1$–$C_6$alkoxy and halo $C_1$–$C_6$alkoxy. More preferably still $R^3$ is 4-fluorophenyl, 4-chlorophenyl, 4-methoxyphenyl or 4-methylphenyl.

The term biolabile ester-forming group is well understood in the art as meaning a group which provides an ester that can be readily cleaved in the body to liberate the corresponding diacid of formula (I) wherein $R^4$ and $R^5$ are both hydrogen. A number of such ester groups are well known, for example in the penicillin area or in the case of the ACE inhibitor hypertensives such as enalapril and quinapril. Compounds of formula (I) containing such biolabile ester-forming groups are particularly advantageous in providing compounds suitable for oral administration. The suitability of any particular ester-forming group can be assessed by conventional animal or in vitro enzyme hydrolysis studies. For optimum effect, the ester should only be hydrolysed after absorption. Accordingly the ester should be resistant to hydrolysis before absorption by digestive enzymes but should be readily hydrolysed by, for example, liver or plasma enzymes. In this way the active diacid is released into the blood stream following oral absorption.

Preferred biolabile ester-forming groups are $C_1$–$C_6$alkyl, carbocyclyl or heterocyclyl each of which may be substituted.

More preferred biolabile ester-forming groups are: i) $C_1$–$C_6$alkyl optionally substituted by hydroxy, oxo, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio, nitrile, carbocyclyl, heterocyclyl, carbocyclyloxy, heterocyclyloxy, $C_1$–$C_7$alkylcarbonyloxy, carbocyclylcarbonyloxy, heterocyclylcarbonyloxy, alkylcarbonylamino, and alkylaminocarbonyl, wherein any carbocyclyl or heterocyclyl group is optionally substituted by $C_1$–$C_6$alkyl, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio or nitrile; or ii) carbocyclyl or heterocyclyl optionally substituted by $C_1$–$C_6$alkyl, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio or nitrile. In the definitions of i) and ii) any carbocyclic group is preferably phenyl and any heterocyclic group is aromatic.

Still more preferred biolabile ester-forming groups are selected from the list: ethyl, propyl, butyl, isobutyl, cyclopentyl, benzyl, 1-(2,2-diethylbutyryloxy)ethyl, 2-ethylpropionyloxymethyl, 1-(2-ethylpropionyloxy)ethyl, 1-(2,4-dimethylbenzoyloxy)ethyl, 1-benzoyloxy)benzyl, 1-(benzoyloxy)ethyl, 2-methyl-1-propionyloxypropyl, 2,4,6-trimethylbenzoyloxymethyl, 1-(2,4,6-trimethylbenzyloxy)ethyl, pivaloyloxymethyl, phenethyl, phenpropyl, 2,2,2-trifluororethyl, 1-naphthyl, 2-naphthyl, 2,4-dimethylphenyl, 4-t-butylphenyl, 5-(4-methyl-1,3-dioxalynyl-2-onyl)methyl, N,N-diethylaminocarbonylmethyl and 5-indanyl.

Preferably $R^4$ and $R^5$ are both hydrogen.

A preferred compound is of formula (Ia) wherein $R^1$, $R^2$, $R^3$, $R^4$, $R^5$ and L are as defined in the first aspect.

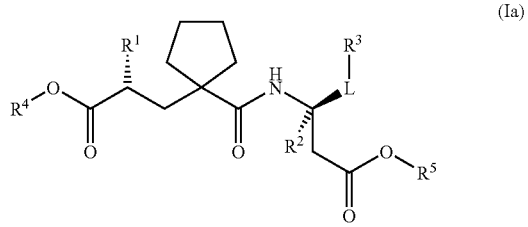

(Ia)

A preferred compound of formula (Ia) is where
$R^1$ is $C_1$–$C_6$alkyl or $C_1$–$C_6$alkoxy$C_1$–$C_3$alkyl;
$R^2$ is hydrogen;
L is a three atom linkage selected from: —$CH_2$—O—$CH_2$—, —$CH_2$—$CH_2$—O— and $CH_2$—$CH_2$—$CH_2$—, where the right hand side of the linkage is attached to $R^3$;
$R^3$ is phenyl which may be independently substituted by one or more groups selected from: $C_1$–$C_6$alkyl, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio and nitrile; and
$R^4$ and $R^5$ are either both hydrogen, or one of $R^4$ and $R^5$ is hydrogen and the other is a biolabile ester-forming group that in the body of a patient is replaced by hydrogen.

A more preferred compound of formula (Ia) is where
$R^1$ is $C_1$–$C_6$alkyl or $C_1$–$C_6$alkoxy$C_1$–$C_3$alkyl;
$R^2$ is hydrogen;
L is —$CH_2$—$CH_2$—O— or $CH_2$—$CH_2$—$CH_2$— where the right hand side of the linkage is attached to $R^3$;
$R^3$ is phenyl which may be independently substituted by one or more groups selected from: $C_1$–$C_6$alkyl, halo, halo$C_1$–$C_6$alkyl, $C_1$–$C_6$alkoxy and halo$C_1$–$C_6$alkoxy; and
$R^4$ and $R^5$ are either both hydrogen, or one of $R^4$ and $R^5$ is hydrogen and the other is a biolabile ester-forming group that in the body of a patient is replaced by hydrogen.

A still more preferred compound of formula (Ia) is where
$R^1$ is $C_1$–$C_6$alkyl or $C_1$–$C_6$alkoxy$C_1$–$C_3$alkyl;
$R^2$ is hydrogen;
L is —$CH_2$—$CH_2$—O— or $CH_2$—$CH_2$—$CH_2$— where the right hand side of the linkage is attached to $R^3$;
$R^3$ is phenyl which may be independently substituted by one or more groups selected from: $C_1$–$C_6$alkyl, halo, halo$C_1$–$C_6$alkyl, $C_1$–$C_6$alkoxy and halo$C_1$–$C_6$alkoxy; and
$R^4$ and $R^5$ are both hydrogen.

A still more preferred compound of formula (Ia) is where
$R^1$ is propyl or methoxyethyl;
$R^2$ is hydrogen;
L is —$CH_2$—$CH_2$—O— or $CH_2$—$CH_2$—$CH_2$—, where the right hand side of the linkage is attached to $R^3$;
$R^3$ is 4-fluorophenyl, 4-chlorophenyl, 4-methoxyphenyl or 4-methylphenyl; and
$R^4$ and $R^5$ are either both hydrogen, or one of $R^4$ and $R^5$ is hydrogen and the other is a biolabile ester-forming group that in the body of a patient is replaced by hydrogen.

A still more preferred compound of formula (Ia) is where
$R^1$ is propyl or methoxyethyl;
$R^2$ is hydrogen;
L is —$CH_2$—$CH_2$—O— or $CH_2$—$CH_2$—$CH_2$—, where the right hand side of the linkage is attached to $R^3$;
$R^3$ is 4-fluorophenyl, 4-chlorophenyl, 4-methoxyphenyl or 4-methylphenyl; and
$R^4$ and $R^5$ are either both hydrogen, or one of $R^4$ and $R^5$ is hydrogen and the other is a biolabile ester-forming group that in the body of a patient is replaced by hydrogen, selected from: i) $C_1$–$C_6$alkyl optionally substituted by hydroxy, oxo, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio, nitrile, carbocyclyl, heterocyclyl, carbocyclyloxy, heterocyclyloxy, alkylcarbonyloxy, carbocyclylcarbonyloxy, heterocyclylcarbonyloxy, alkylcarbonylamino, and alkylaminocarbonyl, wherein any carbocyclyl or heterocyclyl group is optionally substituted by $C_1$–$C_6$alkyl, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio or nitrile; or ii) carbocyclyl or heterocyclyl optionally substituted by $C_1$–$C_6$alkyl, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio or nitrile.

A most preferred compound of formula (Ia) is where
$R^1$ is propyl or methoxyethyl;
$R^2$ is hydrogen;
L is —$CH_2$—$CH_2$—O— or $CH_2$—$CH_2$—$CH_2$—, where the right hand side of the linkage is attached to $R^3$;
$R^3$ is 4-fluorophenyl, 4-chlorophenyl, 4-methoxyphenyl or 4-methylphenyl; and
$R^4$ and $R^5$ are both hydrogen.

A particularly preferred compound of formula (I) is selected from:
(2S)-2-[(1-{[((1R)-2-carboxy-1-{[(4-chlorobenzyl)oxy]methyl}ethyl)-amino]carbonyl}cyclopentyl)methyl]-4-methoxybutanoic acid (Example 16);
(3S)-3-[({1-[(2R)-2-carboxypentyl]cyclopentyl}carbonyl)amino]-5-(4-chlorophenoxy)pentanoic acid (Example 41);
Ethyl (3S)-3-[({1-[(2S)-2-Carboxy-4-methoxybutyl]cyclopentyl}carbonyl)amino]-5-(4-chlorophenoxy)pentanoate (Example 47);
(3S)-3-[({1-[(2S)-2-carboxy-4-methoxybutyl]cyclopentyl}carbonyl)amino]-5-(4-chlorophenoxy)pentanoic acid (Example 48);
(2S)-2-({1-[({(1S)-3-butoxy-1-[2-(4-chlorophenoxy)ethyl]-3-oxopropyl}amino)carbonyl]cyclopentyl}methyl)-4-methoxybutanoic acid (Example 49);
(3S)-3-[({1-[(2S)-2-carboxy-4-methoxybutyl]cyclopentyl}carbonyl)amino]-6-(4-chlorophenyl)hexanoic acid (Example 53);
Ethyl (3S)-3-[({1-[(2S)-2-carboxy-4-methoxybutyl]cyclopentyl}carbonyl)amino]-6-(4-chlorophenyl)hexanoate (Example 52); and
(3S)-3-[({1-[(2S)-2-carboxy-4-methoxybutyl]cyclopentyl}carbonyl)amino]-6-(4-methoxyphenyl)hexanoic acid (Example 54).

For the avoidance of doubt, unless otherwise indicated, the term substituted means substituted by one or more defined groups. In the case where groups may be selected from a number of alternative groups, the selected groups may be the same or different.

For the avoidance of doubt, the term independently means that where more than one substituent is selected from a number of possible substituents, those substituents may be the same or different.

The pharmaceutically or veterinarily acceptable salts of the compounds of the invention which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For reviews on suitable pharmaceutical salts see Berge et al, J. Pharm, Sci., 66, 1–19, 1977; P L Gould, International Journal of Pharmaceutics, 33 (1986), 201–217; and Bighley et al, Encyclopedia of Pharmaceutical Technology, Marcel Dekker Inc, New York 1996, Volume 13, page 453–497.

The pharmaceutically acceptable solvates of the compounds of the invention include the hydrates thereof.

Also included within the scope of the invention and various salts of the invention are polymorphs thereof.

Hereinafter, compounds their pharmaceutically acceptable salts, their solvates or polymorphs, defined in any aspect of the invention (except intermediate compounds in chemical processes) are referred to as "compounds of the invention".

The compounds of the invention may possess one or more chiral centres and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

The compounds of the invention may exist in one or more tautomeric forms. All tautomers and mixtures thereof are included in the scope of the present invention. For example, a claim to 2-hydroxypyridinyl would also cover its tautomeric form, α-pyridonyl.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the invention, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples and Preparations hereafter using appropriate isotopic variations of suitable reagents.

The compounds of the invention, by inhibiting NEP (particularly EC.3.4.24.11), can potentiate the biological effects of bioactive peptides and thus there is rationale for the compounds of the invention to treat or prevent number of diseases and conditions.

Shepperson et al have demonstrated that the NEP inhibitor candoxatrilat lowers systolic blood pressure in hypertensive rats [see Clin.Sci (Lond), Vol 80(3):265–9]. Kosoglou et al have demonstrated that the NEP inhibitor SCH34826 significantly lowered supine blood pressure in a clinical study of 24 black patients with essential hypertension [Circulation, Supplement III, Vol 82, No. 4, page 554, 2201]. Stergiou et al have demonstrated that when added to the ACE inhibitor lisinopril, candoxatril (the oral prodrug of candoxatrilat) led to a marked reduction in both supine and erect blood pressure in a clinical study involving 37 hypertensive patients [J. Hypertens, Vol 12, No 11, page 1310–1311]. Accordingly, the compounds of the invention should treat or prevent cardiovascular diseases and conditions, particularly hypertension, pulmonary hypertension, peripheral vascular disease, heart failure, angina, renal insufficiency, acute renal failure, cyclical oedema, Menières disease, hyperaldosteroneism (primary and secondary) and hypercalciuria. The term hypertension includes all diseases characterised by supranormal blood pressure, such as essential hypertension, pulmonary hypertension, secondary hypertension, isolated systolic hypertension, hypertension associated with diabetes, hypertension associated with atherosclerosis, and renovascular hypertension, and further extends to conditions for which elevated blood pressure is a known risk factor. Accordingly, the term "treatment of hypertension" includes the treatment or prevention of complications arising from hypertension, and other associated co-morbidities, including congestive heart failure, angina, stroke, glaucoma, impaired renal function, including renal failure, obesity, and metabolic diseases (including Metabolic Syndrome). Metabolic diseases include in particular diabetes and impaired glucose tolerance, including complications thereof, such as diabetic retinopathy and diabetic neuropathy.

The compounds of the invention should be particularly efficacious in treating or preventing hypertension.

Wayman et al [WO 02/079143] have demonstrated that NEP inhibitors increase vaginal and clitoral blood flow in a rabbit model of female sexual arousal disorder (FSAD). Accordingly the compounds of the invention should treat or prevent female sexual dysfunction, particularly FSAD.

Wayman et al (WO 02/03995) have demonstrated that NEP inhibitors potentiate nerve-stimulated erections in anaesthetised dog model of penile erections.

Accordingly the compounds of the invention should treat or prevent male erectile dysfunction (MED).

As a result of their ability to inhibit NEP, the compounds of the invention should treat or prevent menstrual disorders, pre-term labour, pre-eclampsia, endometriosis, and reproductive disorders (especially male and female infertility, polycystic ovarian syndrome, implantation failure).

In addition, the compounds of the invention should: treat or prevent asthma, inflammation, leukemia, pain, epilepsy, affective disorders, dementia and geriatric confusion, septic shock, obesity and gastrointestinal disorders (especially diarrhoea and irritable bowel syndrome); promote wound healing (especially diabetic and venous ulcers and pressure sores); modulate gastric acid secretion; and treat hyperreninaemia, cystic fibrosis, restenosis, diabetic complications and atherosclerosis.

As used herein, the terms "treat", "treating" and "treatment" include palliative, curative and prophylactic treatment.

Compounds of the invention may be prepared, in known manner in a variety of ways. In the following reaction schemes and hereafter, unless otherwise stated, $R^1$ to $R^5$, L and X are as defined in the first aspect. These processes form further aspects of the invention.

Throughout the specification, general formulae are designated by Roman numerals I, II, III, IV etc. Subsets of these general formulae are defined as Ia, Ib, Ic etc, . . . IVa, IVb, IVc etc.

Compounds of formula (Ib), i.e. compounds of general formula (I) where $R^4$ and $R^5$ are hydrogen and L is —$CH_2OCH_2$—, may be prepared according to reaction scheme 1, by de protecting a compound of general formula (II) where $P^1$ is a suitable carboxyl protecting group, such as $C_1$–$C_4$ alkyl or benzyl, preferably ethyl or t-butyl.

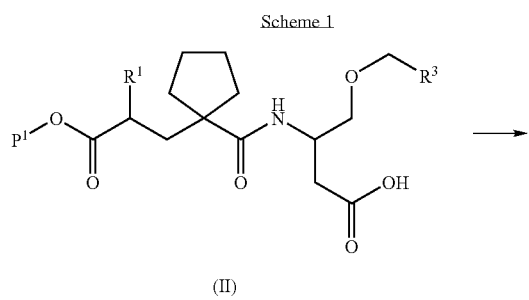

Deprotection can be performed using standard methodology, as described in "Protecting Groups in Organic Synthesis" by T. W. Greene and P. Wutz". When $P^1$ is t-butyl, then the preferred conditions are 9–40% trifluoroacetic acid in dichloromethane (by volume) at room temperature for 1 to 72 hours. When $P^1$ is allyl, preferred conditions are pyrrolidine (4 equiv), tetrakistriphenylphosphine paladium (0) (catalytic) in tetrahydrofuran at room temperature for 2–3 hours. When $P^1$ is ethyl, preferred conditions are 1N sodium hydroxide in dioxan, methanol or tetrahydrofuran at a temperature between room temperature and reflux for 2–18 hours.

Compounds of formula (II) may be prepared by reacting compounds of formula (III) with $R^3CH_2Y$ (where Y is a halogen atom, preferably bromine or iodine).

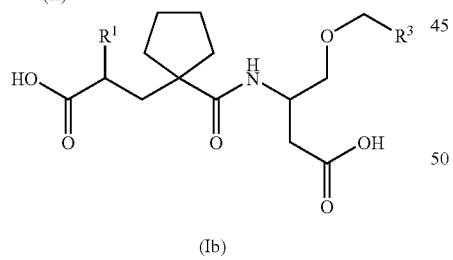

Preferred conditions comprise reacting (III) with $R^3CH_2Y$ in the presence of a suitable alkali metal base (for example sodium hydride, potassium carbonate or caesium carbonate) in a suitable solvent (for example tetrahydrofuran or N,N-dimethylformamide), optionally in the presence of a catalyst (for example imidazole or 4-dimethylaminopyridine). Particularly preferred conditions are sodium hydride (6–10 equiv), imidazole (0.2 equiv) and $R^3CH_2Y$ (1.1 equiv) in tetrahydrofuran at between −15° C. and room temperature for 2–3 hrs.

Compounds of formula (III) may be prepared from compounds of formula (IV) according to reaction scheme 3.

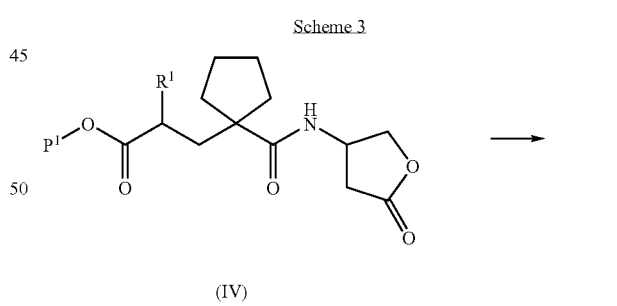

Preferred reaction conditions comprise reacting compounds of formula (IV) under acid conditions (for example hydrochloric acid) or basic conditions (for example sodium hydroxide or caesium hydroxide) in the presence of a catalyst in a suitable solvent (for example methanol or dioxan) at a temperature of between room temperature and the reflux temperature of the reaction mixture. Preferred conditions are 1N sodium hydroxide:methanol (25:75, by volume) at room temperature for 18 hours.

Compounds of formula (IV) may be prepared by reacting compounds of formula (V) with compounds of formula (VI) according to reaction scheme 4.

Scheme 4

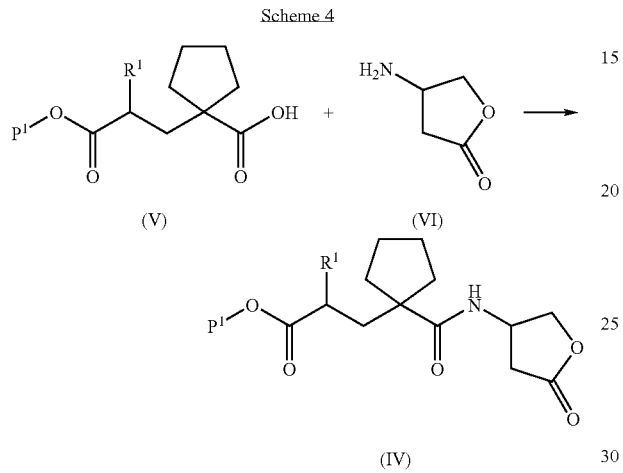

(V)    (VI)

(IV)

Typical reaction conditions comprise generating the acid chloride of compounds of formula (V) followed by addition of compounds of formula (VI), optionally in the presence of an excess of tertiary amine (such as triethylamine, Hünig's base or N-methylmorpholine) in a suitable solvent (such as dichloromethane or tetrahydrofuran) at room temperature for between 1 to 24 hours.

Alternative reaction conditions comprise reacting compounds of formula (V), 1-(3-dimethylaminopropyl)-3-ethylcarbodiimide hydrochloride (WSCDI)/1,3-dicyclohexylcarbodiimide (DCC), 1-hydroxybenzotriazole hydrate (HOBT)/HOAT and compounds of formula (VI), with an excess of a tertiary amine (such as N-methylmorpholine, triethylamine or Hünig's base) in a suitable solvent (for example tetrahydrofuran, dichloromethane or ethyl acetate) at room temperature for between 4 to 48 hours.

Further reaction conditions comprise reacting a compound of formula (V), PYBOP®/PyBrOP®/Mukaiyama's reagent and an excess of compound of formula (VI), with an excess of tertiary amine (N-methylmorpholine, triethylamine or Hünig's base) in a suitable solvent (such as tetrahydrofuran, dichloromethane or ethyl acetate) at room temperature for 4 to 24 hours.

Preferred reaction conditions comprise reacting compounds of formula (VI) (1 equiv), a compound of formula (V) (1–1.1 equiv), WSCDI (1–1.1 eq), 1-hydroxybenzotriazole hydrate (HOBT) (1–1.1 eq) and N-methylmorpholine (2 equiv) in dichloromethane at room temperature for about 18 hours.

Compounds of formula (V) may be prepared by published methods, or by simple modifications of these methods. See for example: A. S. Cook et al., European Patent Application EP 1 258 474 A2 (Pfizer Ltd. et al.); S. Challenger et al., International Patent Application WO02/79143 (Pfizer Ltd. et al.); C. G. Barber et al., International Patent Application WO02/02513 (Pfizer Ltd. et al.); C. J. Cobley et al., Tetrahedron Letts. 42(42), 7481–7483 (2001); S. Challenger, European Patent Application 0 644 176 A1 (Pfizer Ltd.).

Compounds of formula (Ic), i.e. compounds of general formula (I) where $R^5$ is hydrogen, $R^4$ is nor hydrogen and L is —$CH_2OCH_2$—, may be prepared from compounds of formula (II) according to reaction scheme 5.

Scheme 5

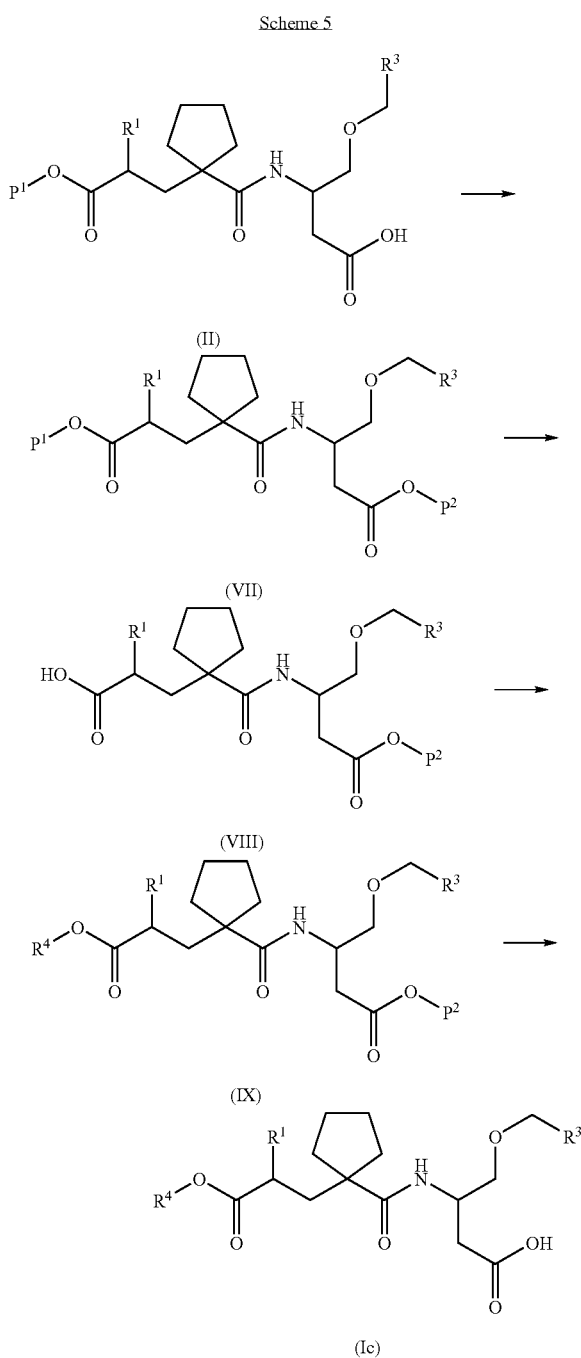

(II)

(VII)

(VIII)

(IX)

(Ic)

Compounds of formula (VII) may be prepared by reacting a compound of formula (II) (where $P^1$ is a protecting group removable under acidic conditions, such as t-butyl) with $P^2Y^1$ (where $P^2$ is an acid stable protecting group, such as benzyl or allyl, and $Y^1$ is a leaving group, typically halogen, preferably bromine or iodine), with an excess of an alkali metal base (for example potassium carbonate or caesium carbonate), or a tertiary amine base (for example triethylamine) in a suitable solvent (for example N,N-dimethylformamide or acetonitrile) at room temperature. Preferred reaction conditions comprise reacting a compound of formula (II) with of $P^2Y^1$ (2.3 equiv) and potassium carbonate (1–3 equiv) in N,N-dimethylformamide for 18 to 72 hours.

Compounds of formula (VIII) may be prepared from compounds of formula (VII). When $P^1$ is t-butyl, then the preferred conditions are 9–40% trifluoroacetic acid in dichloromethane (by volume) at room temperature for 1 to 72 hours.

Compounds of formula (IX) may be prepared from compounds of formula (VIII) using analogous methods described for the preparation of compounds of formula (VII) replacing $P^2Y^1$ with $R^4Y^1$.

Compounds of formula (Ic) may be prepared from compounds of formula (IX). When $P^2$ is benzyl, preferred conditions comprise hydrogenation. When $P^2$ is allyl preferred conditions comprise pyrrolidine, tetrakistriphenylphosphine paladium (0) (catalytic) in tetrahydrofuran at room temperature for 2–3 hours.

Compounds of formula (Id), i.e. compounds of general formula (I) where $R^4$ is hydrogen, $R^5$ is not hydrogen and L is —$CH_2OCH_2$—, may be prepared according to reaction scheme 6, where $P^1$ is a suitable carboxyl protecting group, preferably t-butyl.

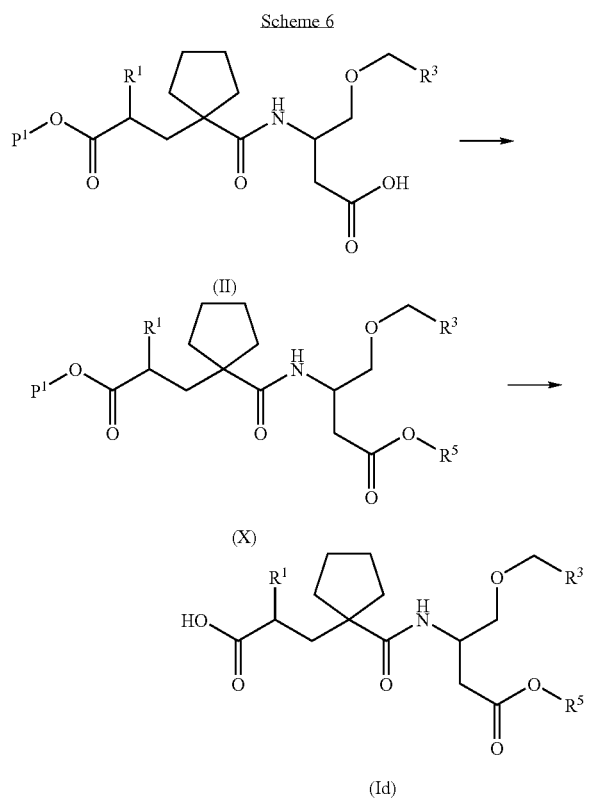

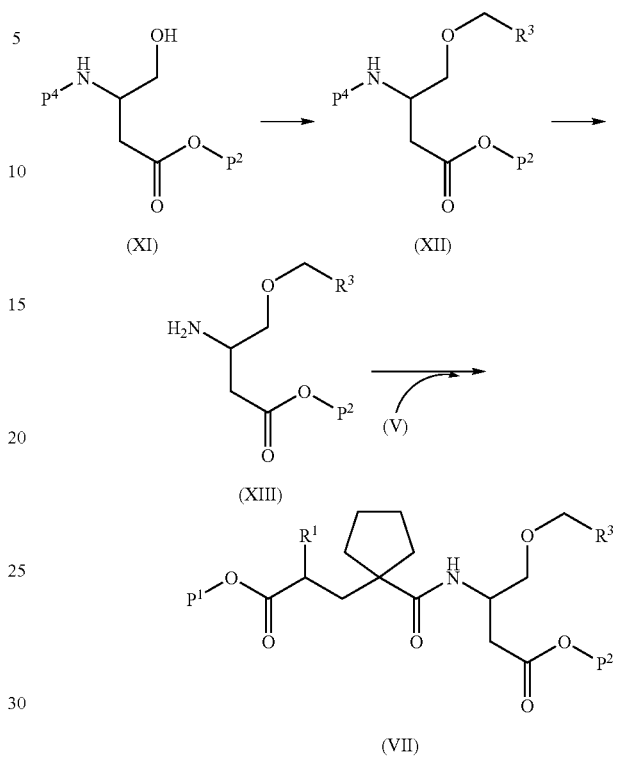

Compounds of formula (X) where $P^1$ is a suitable carbonyl protecting group preferably t-butyl, may be prepared from compounds of formula (II) in analogous fashion to the preparation of compounds of formula (IX) (see scheme 5).

Compounds of formula (Id) may be prepared from compounds of formula (X) in analogous fashion to scheme 1. For example when $P^1$ is t-butyl preferred reaction conditions comprise trifluoroacetic acid or hydrochloric acid.

Alternatively compounds of formula VII may be prepared according to reaction scheme 7.

Compounds of formula (XII) may be prepared by treating a compound of formula (XI) with $R^3CH_2Hal$ in analogous fashion the methods described for Scheme 2 where $P^4$ is a suitable nitrogen protecting group, such as tert-butyloxycarbonyl (Boc) or benzyloxycarbonyl (CBz), preferably Boc. The amine protecting group $P^4$ in compounds of formula (XII) may then be selectively removed using standard methodology, as described in "Protecting Groups in Organic Synthesis" by T. W. Greene and P. Wutz". Preferred conditions, when $P^4$ is Boc are hydrochloric acid in ethyl acetate, ethanol or dichloromethane or, trifluoroacetic acid in dichloromethane at room temperature for between 15 minutes and 3 hours. Preferred conditions when $P^4$ is CBz are hydrobromic acid in acetic acid at room temperature for about 5 hrs. Compounds of formula (VII) may then be obtained by reaction compounds of formula (XIII) with compounds of formula (V) in analogous fashion to the methods described for Scheme 4.

Compounds of formula (Id), i.e. compounds of general formula (I) where $R^4$ and $R^5$ are hydrogen and L is —$CH_2CH_2O$—, may be prepared according to reaction scheme 8.

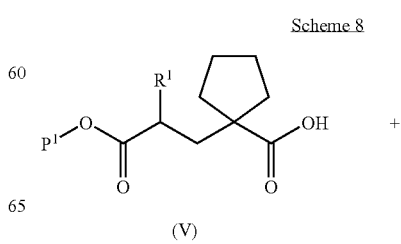

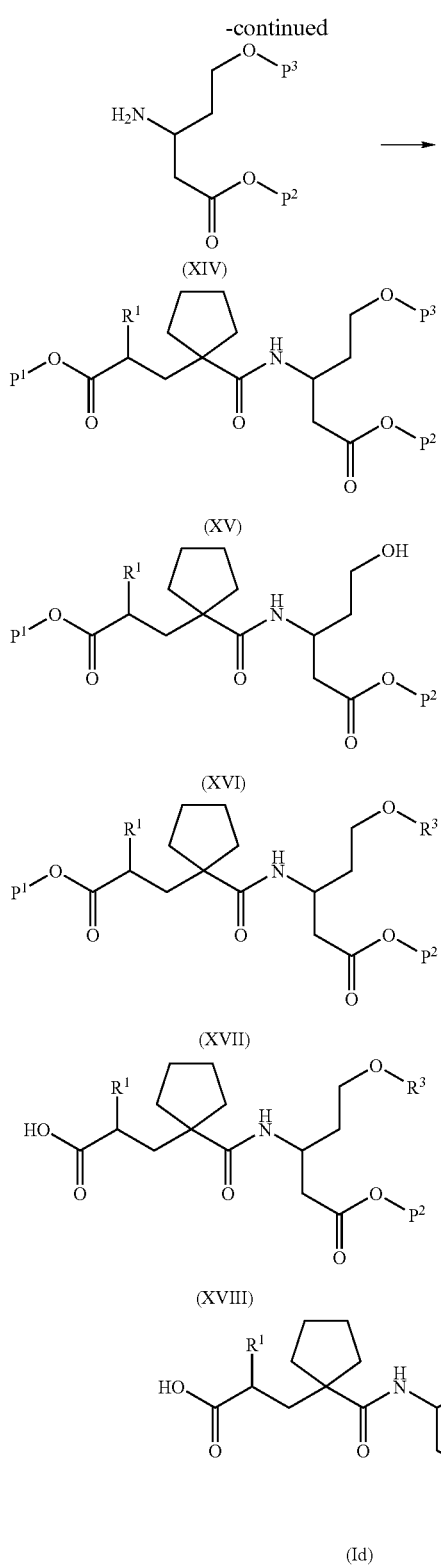

(XIV)

(XV)

(XVI)

(XVII)

(XVIII)

(Id)

Compounds of formula (XV) may be prepared by reacting a compound of formula (V) with a compound of formula (XIV) using analogous conditions to those described for Scheme 4, where $P^1$ and $P^2$ are suitable carboxyl protecting groups, typically $C_1$–$C_4$ alkyl or benzyl, preferably ethyl or t-butyl, and $P^3$ is a suitable hydroxyl-protecting group, typically silyl. Compounds of formula (XVI) may be prepared by removal of the alcohol protecting group using standard methodology, as described in "Protecting Groups in Organic Synthesis" by T. W. Greene and P. Wutz". When $P^3$ is a silyl group, such as t-butyldimethylsilyl, preferred conditions are acetic acid:tetrahydrofuran:water (50:25:25) at room temperature for 2 hours. Compounds of formula (XVII) may be prepared by reacting (XVI) with $R^3$OH using Mitsunobu conditions described in Synthesis 1 (1981) or Org. React. 42; 335 (1992). Preferred reaction conditions comprise diisopropylazadicarboxylate (DIAD) (1.3 equiv), triphenylphosphine (1.3 equiv), $R^3$OH (1.3 equiv) in tetrahydrofuran for 18 hours at room temperature. Compounds of formula (Id) may be prepared in two steps from (XVII) by deprotection methodology described previously in Scheme 1.

Compounds of formula (Id) where X is S, may be prepared by reaction of (XVI) with $R^3$SH, under the Mitsunobu conditions described for the preparation of (XVII), followed by removal of the carboxyl protecting groups, as described in step for scheme 1.

Compounds of formula (XIV) may be prepared according to reaction scheme 9 by reacting compounds of formula (XIX) where $P^2$ is a suitable carboxyl protecting group, typically $C_1$–$C_4$ alkyl or benzyl, preferably ethyl or t-butyl, and $P^3$ is a suitable hydroxyl protecting group, typically silyl, with a suitable chiral amine according to the methods described by Davies et. al. (Tet. Asymm. 1991; 2; 183).

Scheme 9

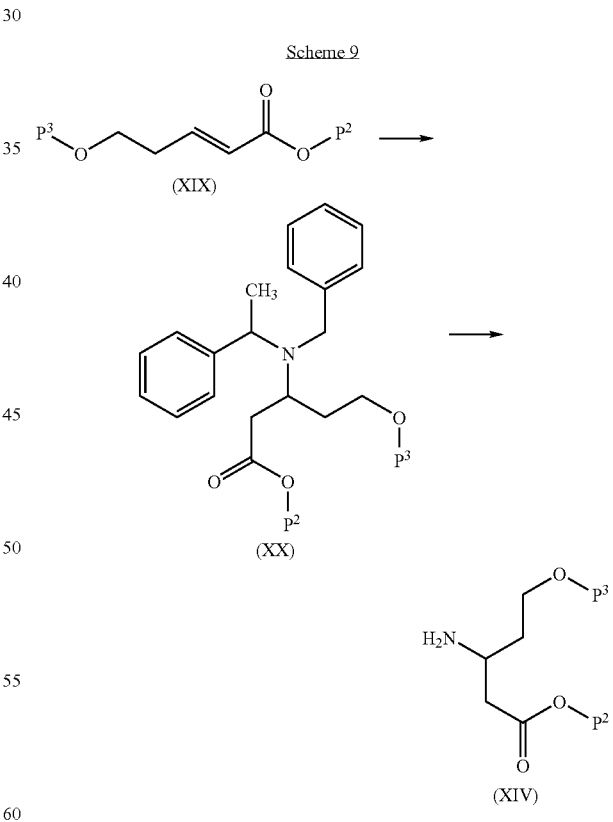

(XIX)

(XX)

(XIV)

Preferred conditions comprise n-butyl lithium (1.5 equiv) and the chiral auxiliary NH(benzyl)(α-methylbenzyl) (1.6 equiv) in tetrahydrofuran at −78° C. for about 3 hours. The N-benzyl protecting groups may be removed by reacting (XX) in the presence of a suitable palladium catalyst (such as palladium on charcoal or palladium hydroxide) in a suitable solvent (such as acetic acid or ethanol). Preferred conditions are 10% palladium on charcoal in acetic acid at room temperature for up to 72 hours.

Compounds of formula (Ie), i.e. compounds of general formula (I) where $R^4$ is hydrogen, $R^5$ is not hydrogen and L is —$CH_2CH_2O$— may be prepared from compounds of formula (XVII) according to reaction scheme 10, wherein $P^1$ is a suitable carboxyl protecting group, typically $C_1$–$C_4$alkyl or benzyl, preferably, t-butyl.

groups, typically $C_1$–$C_4$ alkyl or benzyl, preferably t-butyl. $P^4$ is a suitable amino protecting group, preferably benzyloxycarbonyl.

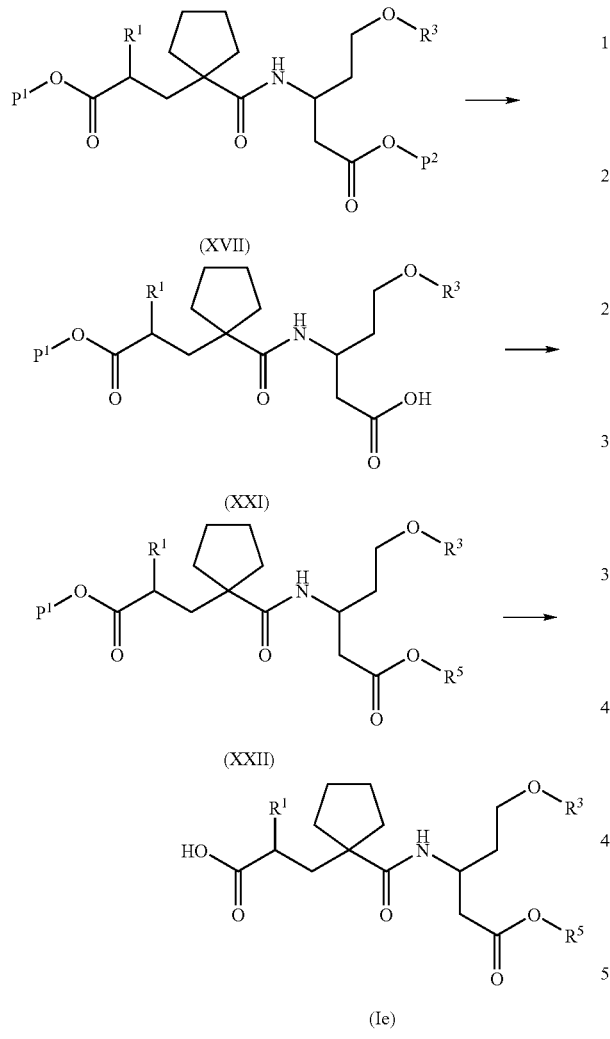

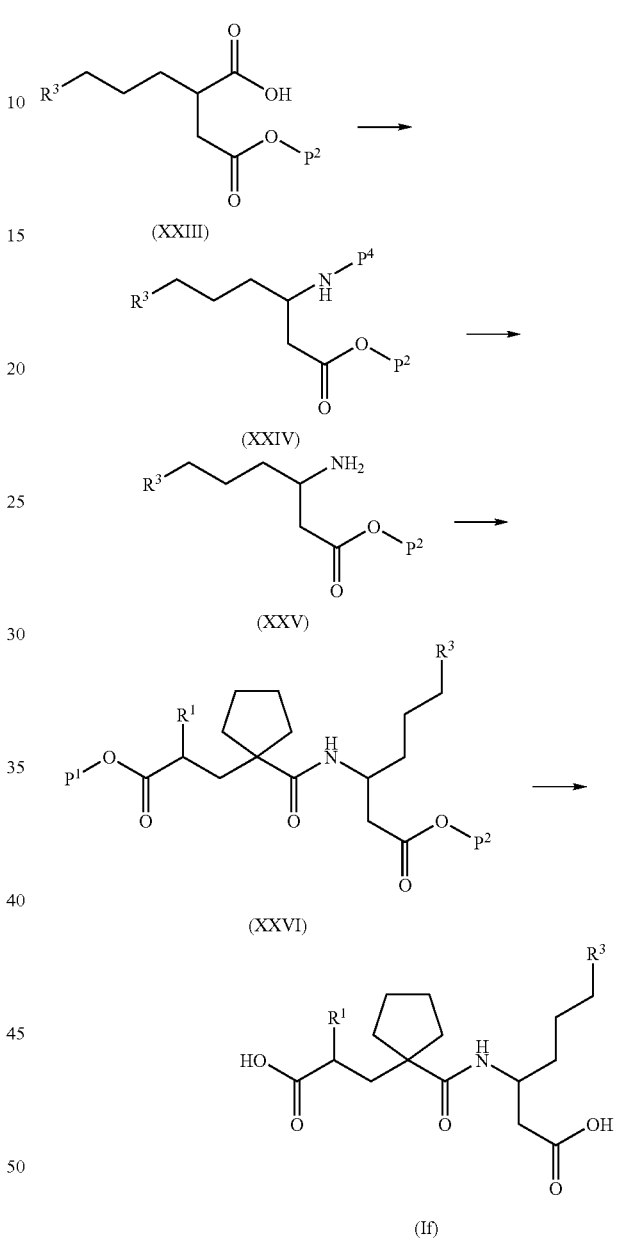

Compounds of formula (XXI) may be prepared by removal of the protecting group $P^2$ from compounds of formula (XVII) using analogous methods to those described for Scheme 5 and 6. Compounds of formula (XXII) may be prepared in turn by reaction of compounds of formula (XXI) with $R^5$Hal using analogous methods described for the preparation of compounds of formula (VII). Compounds of formula (Ie) may be prepared from compounds of formula (XXII) by deprotection methods as described for Scheme 6.

Compounds of formula (If), i.e. compounds of general formula (I) wherein L is —$CH_2CH_2CH_2$—, and $R^4$ and $R^5$ are both hydrogen may be prepared according to reaction scheme 11 where $P^1$ and $P^2$ are suitable carboxyl protecting Compounds of formula (XXIV) may be prepared from compounds of formula (XXIII) under the conditions described by Evans et. al (J.Org.Chem. 1999; 64; 6411) or Talley (EP 0561758). Compounds of formula (XXIII) may be prepared in analogous fashion to the methods described by Beeley et. al. in WO 9504033. Preferred conditions for the preparation of compounds of formula (XXIV) are diphenylphosphoryl azide (1 equiv), triethylamine (1.2 equiv) in toluene at reflux for 2 to 3.5 hours, followed by addition of benzyl alcohol (3 equiv) at a temperature between room temperature and reflux for about 18 hours. Compounds of formula (XXV) may be obtained from compounds of formula (XXIV) by removal of protecting group $P^4$ using methods analogous to those described for the preparation of compounds of formula (XIII) (see scheme 7). Compounds of formula (XXVI) may be prepared by coupling compounds of formula (XXV) with the compounds of formula (V) using analogous methods to those described for Scheme 4. Removal of the protecting groups from compounds of formula (XXVI) using analogous methods to those described for Scheme 1 gave compounds of formula (If).

Compounds of formula (Ig), i.e. compounds of general formula (I) where L is —$CH_2CH_2CH_2$—, $R^4$ is hydrogen and $R^5$ is not hydrogen may be prepared according to reaction scheme 12 where $P^1$ and $P^2$ are suitable carboxyl protecting groups, typically $C_1$–$C_4$ alkyl or benzyl, preferably t-butyl, and $P^4$ is a suitable amino protecting group, preferably CBz.

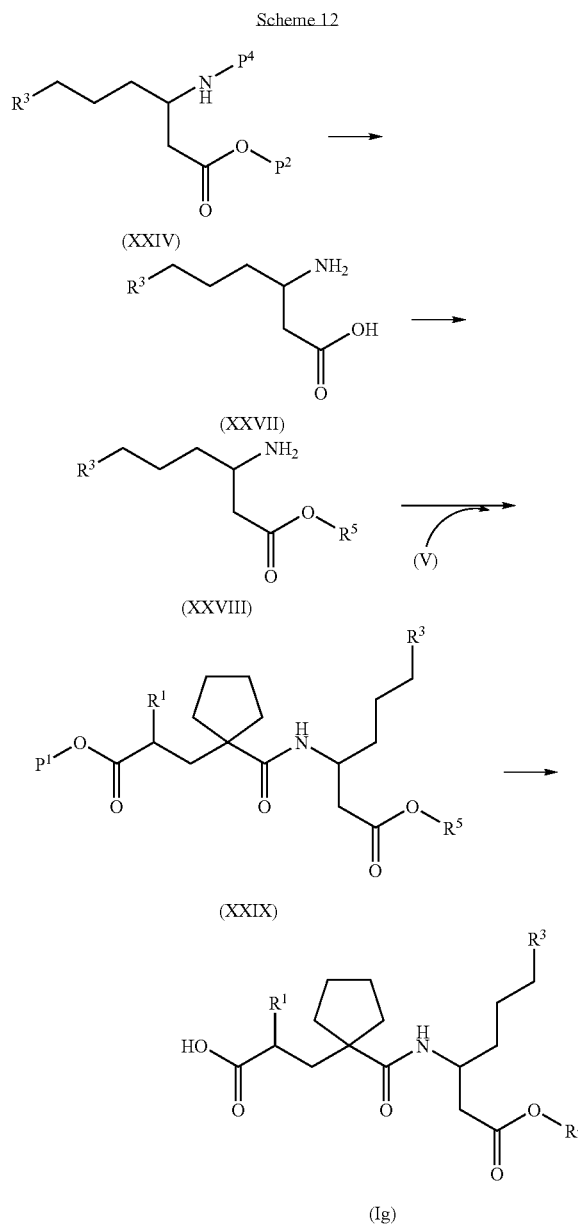

Compounds of formula (XXVII) may be prepared by de protecting compounds of formula (XXIV). When $P^2$ is t-butyl and $P^4$ is benzyloxycarbonyl, preferred conditions are hydrobromic acid in acetic acid at room temperature for about 5 hours. Compounds of formula (XXVIII) may be obtained by reacting compounds of formula (XXVII) with $R^5OH$ under acid catalysis. Compounds of formula (XXIX) may be prepared by coupling the compounds of formula (XXVIII) with compounds of formula (V) using methods analogous to those described for Scheme 4. Removal of the protecting groups from compounds of formula (XXIX) using methods analogous to those described for Scheme 6 gave compounds of formula (Ig).

It will be appreciated by those skilled in the art, that certain compounds of formula (I) where $R^4$ or $R^5$ are not hydrogen may be converted to compounds of formula (I) where $R^4$ or $R^5$ are hydrogen, using standard ester hydrolysis conditions analogous to those described for Scheme 1.

In addition, it will be appreciated by those skilled in the art, that certain compounds of formula (I) where $R^4$ or $R^5$ are hydrogen, may be converted to compounds of formula (I) where $R^4$ or $R^5$ are not hydrogen using standard esterification conditions analogous to those described for the preparation of compounds of formula (VII) in scheme 5.

Alternatively it will be appreciated by those skilled in the art, that certain compounds of formula (I) where $R^4$ or $R^5$ are not hydrogen, may be converted to compounds of formula (I) with alternative $R^4$ or $R^5$ groups, using standard transesterification conditions.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

Procedures for isolating the desired products will be well-known to those skilled in the art with reference to literature precedents and the Examples and Preparations hereto.

The compounds of the invention can be administered alone but will generally be administered in admixture with a suitable pharmaceutical excipient, diluent or carrier selected with regard to the intended route of administration and standard pharmaceutical practice.

For example, the compounds of the invention can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the invention may also be administered as fast-dispersing or fast-dissolving dosage forms or in the form of a high energy dispersion or as coated particles. Suitable formulations of the compounds of the invention may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinyl pyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

GENERAL EXAMPLE

A formulation of the tablet could typically contain between about 0.01 mg and 500 mg of active compound whilst tablet fill weights may range from 50 mg to 1000 mg. An example of a formulation for a 10 mg tablet is illustrated below:

| Ingredient | % w/w |
|---|---|
| Free acid, Free base or Salt form | 10.000* |
| Lactose | 64.125 |
| Starch | 21.375 |
| Croscarmellose Sodium | 3.000 |
| Magnesium Stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intracavernouslly, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The following dosage levels and other dosage levels herein are for the average human subject having a weight range of about 65 to 70 kg. The skilled person will readily be able to determine the dosage levels required for a subject whose weight falls outside this range, such as children and the elderly.

For oral and parenteral administration to human patients, the daily dosage level of the compounds of the invention will usually be from 0.01 mg/kg to 10 mg/kg (in single or divided doses).

Thus tablets or capsules of the compound of the invention may contain from 1 mg to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the pulmonary, vaginal or rectal routes.

They may also be administered by the ocular route, particularly for treating disorders of the eye. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

For treating cardiovascular disorders, particular hypertension, the compounds of the invention may be combined with one or more active ingredient selected from the list:

a) angiotensin receptor blockers (ARB), such as losartan, valsartan, telmisartan, candesartan, irbesartan, eprosartan and olmesartan;

b) calcium channel blockers (CCB) such as amlodipine;

c) statins, such as atorvastatin;

d) PDE5 inhibitors, such as sildenafil, tadalafil, vardenafil, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one and; the pyrazolo[4,3-d]pyrimidin-4-ones disclosed in WO00/27848 particularly N-[[3-(4,7-dihydro-1-methyl-7-oxo-3-propyl-1H-pyrazolo[4,3-d]-pyrimidin-5-yl)-4-propxyphenyl]sulfonyl]-1-methyl2-pyrrolidinepropanamide [DA-8159 (Example 68 of WO00/27848)];

e) beta blockers, such as atenolol or carvedilol;

f) ACE inhibitors, such as quinapril, enalapril and lisinopril;

g) alpha-blockers such as doxazosin;

h) selective aldosterone receptor antagonists (SARA), such as eplerenone or spironolactone;

i) imidazoline $I_1$ agonists, such as rilmenidine or monoxidine; and j) endothelin receptor antagonists and endothelin converting enzyme inhibitors.

For treating FSAD, the compounds of the invention may be combined with one or more active ingredient selected from the list:

a) PDE5 inhibitors, such as sildenafil, tadalafil, vardenafil, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one and; the pyrazolo[4,3-d]pyrimidin-4-ones disclosed in WO00/27848 particularly N-[[3-(4,7-dihydro-1-methyl-7-oxo-3-propyl-1H-pyrazolo[4,3-d]-pyrimidin-5-yl)-4-propxyphenyl]sulfonyl]-1-methyl2-pyrrolidinepropanamide [DA-8159 (Example 68 of WO00/27848)];

b) dopaminergic agents, preferably apomorphine or a selective $D_2$, $D_3$ or $D_2/D_3$ agonist such as, pramipexole and ropirinol (as claimed in WO-00/23056), PNU95666 (as claimed in WO-00/40226);

c) melanocortin receptor agonists, such as melanotan II; PT-14; PT-141; compounds claimed in WO-99/64002, WO-00/74679, WO-99/55679, WO-01/05401, WO-00/58361, WO-01/14879, WO-01/13112 and WO-99/54358; selective MC4 receptor agonists such as those disclosed by Martin et al [European Journal of Pharmacology, 454 71–79 (2002)] particularly (N-[(3R)-1,2,3,4-tetrahydroisoquinolinium-3-ylcarbonyl]-(1R)-1-(4-chlorobenzyl)-2-[4-cyclohexyl-4-(1H-1,2,4-triazol-1-ylmethyl)piperidin-1-yl]-2-oxoethylamine (THIQ); and selective MC3 receptor agonists d) selective estrogen receptor modulators (SERMs) such as lasofoxifene and raloxifene;

e) tibolone;

f) an androgen such as androsterone, dehydro-androsterone, testosterone, androstanedione and a synthetic androgen; and g) an oestrogen, such as oestradiol, oestrone, oestriol and a synthetic estrogen, such as oestrogen benzoate.

For treating MED, the compounds of the invention may be combined with one or more active ingredient selected from the list:

a) PDE5 inhibitors, such as sildenafil, tadalafil, vardenafil, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one and; the pyrazolo[4,3-d]pyrimidin-4-ones disclosed in WO00/27848 particularly N-[[3-(4,7-dihydro-1-methyl-7-oxo-3-propyl-1H-pyrazolo[4,3-d]-pyrimidin-5-yl)-4-propxyphenyl]sulfonyl]-1-methyl2-pyrrolidinepropanamide [DA-8159 (Example 68 of WO-00/27848)];

b) dopaminergic agents, preferably apomorphine or a selective $D_2$, $D_3$ or $D_2/D_3$ agonist such as, pramipexole and ropirinol (as claimed in WO-00/23056), PNU95666 (as claimed in WO-00/40226); and c) melanocortin receptor agonists, such as melanotan II; PT-14; PT-141; compounds claimed in WO-99/64002, WO-00/74679, WO-99/55679, WO-01/05401, WO-00/58361, WO-01/14879, WO-01/13112 and WO-99/54358; selective MC4 receptor agonists such as those disclosed by Martin et al [European Journal of Pharmacology, 454 71–79 (2002)] particularly (N-[(3R)-1,2,3,4-tetrahydroisoquinolinium-3-ylcarbonyl]-(1R)-1-(4-chlorobenzyl)-2-[4-cyclohexyl-4-(1H-1,2,4-triazol- 1-ylmethyl)piperidin-1-yl]-2-oxoethylamine (THIQ); and selective MC3 receptor agonists.

If a combination of active agents are administered, then they may be administered simultaneously, separately or sequentially.

The invention also includes the following aspects. The preferred embodiments specified hereinabove for the first aspect extend to these aspects.

The invention additionally includes, but is not limited to:
(i) A pharmaceutical composition including a compound of the invention, together with a pharmaceutically acceptable excipient, diluent or carrier.
(ii) A compound of the invention for use as a medicament.
(iii) The use of a compound of the invention as a medicament for treating or preventing a condition for which a beneficial therapeutic response can be obtained by the inhibition of neutral endopeptidase.
(iv) The use of a compound of the invention as a medicament for treating or preventing cardiovascular diseases and conditions, preferably essential hypertension, pulmonary hypertension, secondary hypertension, isolated systolic hypertension, hypertension associated with diabetes, hypertension associated with atherosclerosis, renovascular hypertension, congestive heart failure, angina, stroke, glaucoma, impaired renal function, renal failure, obesity, metabolic diseases (including Metabolic Syndrome), diabetes and impaired glucose tolerance, including complications thereof, such as diabetic retinopathy and diabetic neuropathy.
(v) A method of treating or preventing cardiovascular diseases and conditions (preferably essential hypertension, pulmonary hypertension, secondary hypertension, isolated systolic hypertension, hypertension associated with diabetes, hypertension associated with atherosclerosis, renovascular hypertension, congestive heart failure, angina, stroke, glaucoma, impaired renal function, renal failure, obesity, metabolic diseases (including Metabolic Syndrome), diabetes and impaired glucose tolerance, including complications thereof, such as diabetic retinopathy and diabetic neuropathy) in a mammal including treating said mammal with an effective amount of a compound of the invention.
(vi) A cardiovascular disease treating pharmaceutical composition comprising a compound of the invention together with a pharmaceutically acceptable excipient, diluent or carrier.
(vii) A compound of the invention for use in treating or preventing cardiovascular diseases and conditions.
(viii) The use of a compound of the invention in the manufacture of a medicament for treating or preventing cardiovascular disease and conditions.

The invention is illustrated by the following non-limiting examples in which the following abbreviations and definitions are used:

| | |
|---|---|
| ES+ | electrospray ionisation positive scan |
| ES− | electrospray ionisation negative scan |
| HPLC | high pressure liquid chromatography |
| m/z | mass spectrum peak |
| MS | mass spectrum |
| TS+ | thermospray ionisation positive scan |

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; DMSO, dimethylsulphoxide. The abbreviation psi means pounds per square inch and LRMS means low resolution mass spectrometry. Where thin layer chromatography (TLC) has been used it refers to silica gel TLC using silica gel 60 F$_{254}$ plates, R$_f$ is the distance travelled by a compound divided by the distance travelled by the solvent front on a TLC plate. Melting points were determined using a Perkin Elmer DSC7 at a heating rate of 20° C./minute).

Example 1

(2R)-2-[(1-{[((1S)-2-Carboxy-1-{[(3-fluorobenzyl)oxy]methyl}ethyl)amino]-carbonyl}cyclopentyl)methyl]pentanoic Acid

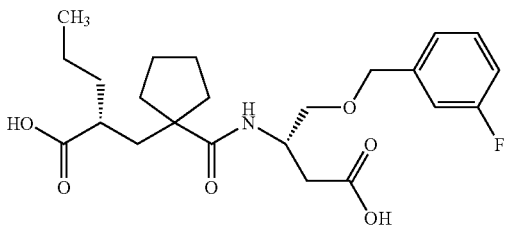

Trifluoroacetic acid (2 ml) was added to a solution of the ester from preparation 11 (80 mg, 0.16 mmol) in dichloromethane (3 ml), and the reaction stirred at room temperature for 90 minutes. The solution was concentrated under reduced pressure and the trifluoroacetic acid removed by azeotrope with toluene, ethyl acetate and dichloromethane to afford the title compound as a colourless oil, 44 mg. $^1$H NMR (CDCl$_3$, 400 MHz) δ:0.87 (t, 3H), 1.22–1.70 (m, 10H), 1.77 (dd, 1H), 1.84 (m, 1H), 1.99 (dd, 1H), 2.17 (m, 1H), 2.38 (m, 1H), 2.71 (d, 2H), 3.59 (m, 2H), 4.50 (m, 3H), 6.58 (d, 1H), 6.95–7.08 (m, 3H), 7.26 (m, 1H). LRMS: m/z (ES$^+$) 438 [MH$^+$].

Examples 2 to 4

The following examples of general formula:

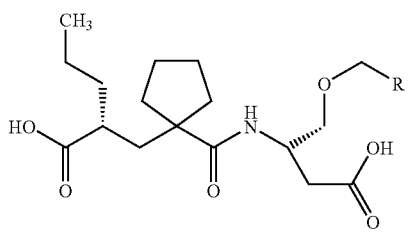

were obtained quantitatively as colourless oils, from the corresponding tert-butyl esters, following a similar procedure to that described in Example 1.

| Ex. No | R² | Data |
|---|---|---|
| 2 | 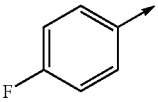 | ¹H NMR(CDCl₃, 400MHz)δ: 0.89(t, 3H), 1.30(m, 2H), 1.38–1.76(m, 8H), 1.84(m, 2H), 1.99(dd, 1H), 2.17(m, 1H), 2.39(m, 1H), 2.75(d, 2H), 3.59(m, 2H), 4.50(m, 3H), 6.62(d, 1H), 7.02(m, 2H), 7.27(d, 2H), LRMS: m/z(ES⁺) 438.3 [MH⁺] |
| 3 | 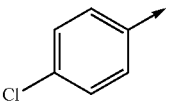 | ¹H NMR(CDCl₃, 400MHz)δ: 0.85(t, 3H), 1.22–1.68(m, 10H), 1.80(m, 2H), 1.98(dd, 1H), 2.16(m, 1H), 2.38(m, 1H), 2.69(d, 2H), 3.58(m, 2H), 4.46(m, 3H), 6.58(d, 1H), 7.20–7.34(m, 4H). LRMS: m/z(ES⁺) 454[MH⁺] Microanalysis found: C, 59.16; H, 6.97; N, 2.95. C₂₃H₃₂ClNO₆; 0.20CH₂Cl₂ requires C, 59.17; H, 6.93; N, 2.97%. |
| 4 | 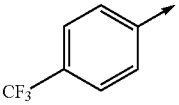 | ¹H NMR(CDCl₃, 400MHz)δ: 0.86(t, 3H), 1.22–1.72(m, 10H), 1.82(m, 2H), 1.98(dd, 1H), 2.17(m, 1H), 2.38(m, 1H), 2.72(d, 2H), 3.60(m, 2H), 4.50(m, 1H), 4.58(s, 2H), 6.60(d, 1H), 7.40(d, 2H), 7.60(d, 2H). LRMS: m/z(ES⁺) 488[MH⁺] |

Example 5

(2R)-2-[(1-{[((1R)-2-Carboxy-1-{[(4-chlorobenzyl)oxy]methyl}ethyl)amino]-carbonyl}cyclopentyl)methyl]pentanoic Acid

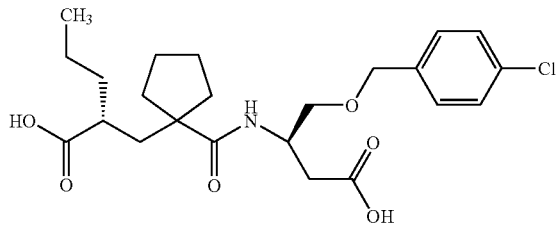

Trifluoroacetic acid (1 ml) was added to a solution of the ester from preparation 15 (125 mg, 0.25 mmol) in dichloromethane (5 ml), and the reaction stirred at room temperature for 18 hours. The solution was concentrated under reduced pressure and the residue azeotroped with dichloromethane (6×). The crude product was purified by column chromatography on silica gel using dichloromethane:methanol:acetic acid (97:3:0.3) as eluant to afford the title compound, 30 mg. ¹H NMR (CDCl₃, 400 MHz) δ: 0.84 (t, 3H), 1.18–1.38 (m, 3H), 1.42–1.52 (m, 7H), 1.79 (dd, 1H), 1.96 (m, 2H), 2.10 (m, 1H), 2.38 (m, 1H), 2.68 (m, 2H), 3.60 (m, 2H), 4.44 (m, 3H), 7.04 (d, 1H), 7.24 (m, 4H). LRMS: m/z (ES⁺) 476 [MNa⁺]; Microanalysis found: C, 58.72; H, 7.05; N, 2.88. C₂₃H₃₂ClNO₆; H₂O requires C, 58.53; H, 7.26; N, 2.97%.

Example 6

(2R)-2-[(1-{[((1R)-2-Carboxy-1-{[(4-fluorobenzyl)oxy]methyl}ethyl)amino]-carbonyl}cyclopentyl)methyl]pentanoic Acid

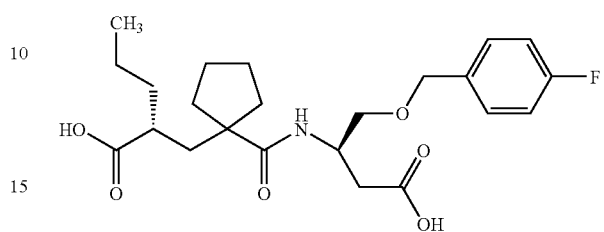

Imidazole (50 mg, 0.73 mmol) and sodium hydride (60% dispersion in mineral oil, 1.24 g, 31 mmol) were added to a cooled (−15° C.) solution of the alcohol from preparation 7 (1.2 g, 3.1 mmol) in tetrahydrofuran (70 ml), and the mixture stirred for 45 minutes. A solution of 4-fluorobenzylbromide (650 mg, 3.4 mmol) was added and the reaction stirred for a further 2 hours a t–15° C., and then allowed to warm to room temperature. Stirring was continued for a further 3 hours, then the flask cooled in an ice-bath. The reaction was quenched by the addition of water, diluted with 1N hydrochloric acid, and the mixture extracted with ethyl acetate. The combined organic solutions were dried (MgSO₄) and evaporated under reduced pressure. The product was purified by column chromatography on silica gel using an elution gradient of dichloromethane:methanol (98:2 to 92:8). This intermediate was dissolved in trifluoroacetic acid (2 ml) and dichloromethane (4 ml), and the reaction stirred at room temperature for 18 hours. The solution was concentrated under reduced pressure and the residue azeotroped with dichloromethane (3×). The crude product was purified by column chromatography on silica gel using dichloromethane:methanol:acetic acid (96:4:0.4) as eluant to afford the title compound, 100 mg. ¹H NMR (CDCl₃, 400 MHz) δ: 0.82 (t, 3H), 1.25 (m, 3H), 1.40–1.81 (m, 8H), 1.96 (m, 2H), 2.15 (m, 1H), 2.38 (m, 1H), 2.58–2.80 (m, 2H), 3.48–3.72 (m, 2H), 4.48 (m, 3H), 6.82 (m, 1H), 7.01 (d, 2H), 7.24 (d, 2H). LRMS: m/z (ES⁻) 436 [M-H]⁻.

Example 7

(2R)-2-[(1-{[((1R)-2-Carboxy-1-{[(3-methoxybenzyl)oxy]methyl}ethyl)amino]-carbonyl}cyclopentyl)methyl]pentanoic Acid

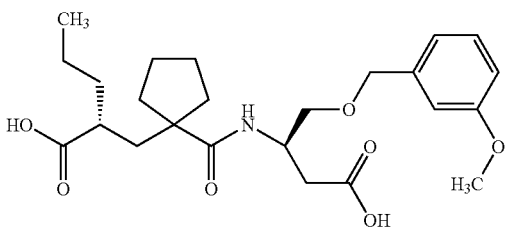

The title compound was obtained in 81% yield from the ester from preparation 16, following the procedure described in Example 5. ¹H NMR (CDCl₃, 400 MHz) δ: 0.84 (t, 3H), 1.20–1.38 (m, 3H), 1.44–1.70 (m, 7H), 1.79 (dd, 1H), 1.90 (m, 1H), 2.02 (m, 2H), 2.38 (m, 1H), 2.70 (m, 2H), 3.60 (m, 2H), 3.80 (s, 3H), 4.44 (m, 3H), 6.84 (m, 2H), 7.02 (d, 1H), 7.24 (m, 2H), 7.82 (br s, 2H). LRMS: m/z (ES$^+$) 472 [MNa$^+$].

Example 8

(2R)-2-[(1-{[((1R)-2-Carboxy-1-{[(4-cyanobenzyl)oxy]methyl}ethyl)amino]-carbonyl}cyclopentyl)methyl]pentanoic Acid

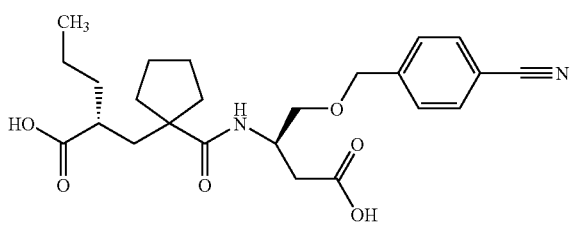

A solution of the ester from preparation 52 (60 mg, 0.13 mmol) and 1M sodium hydroxide (2 ml) in dioxan (6 ml) was stirred at room temperature for 3 hours. The reaction was concentrated under reduced pressure the residue suspended in water (3 ml), the pH adjusted to 1 using 2N hydrochloric acid, and the solution extracted with ethyl acetate (3×3 ml). The combined organic extracts were washed with brine, dried (MgSO$_4$) and evaporated under reduced pressure to afford the title compound as a colourless gum, 55 mg. $^1$H NMR (CDCl$_3$, 400 MHz) δ: 0.82 (t, 3H), 1.18–1.38 (m, 3H), 1.42–1.72 (m, 7H), 1.79 (d, 1H), 1.98 (m, 2H), 2.18 (m, 1H), 2.40 (m, 1H), 2.62 (dd, 1H), 2.79 (dd, 1H), 3.62 (m, 2H), 4.52 (m, 1H), 4.59 (s, 2H), 6.94 (d, 1H), 7.40 (d, 2H), 7.62 (d, 2H). LRMS: m/z (ES$^-$) 443 [M-H]$^-$.

Example 9

Sodium (2R)-2-[(1-{[((1R)-1-{[(5-methyl-2-pyridinyl)methoxy]methyl}-3-oxido-3-oxopropyl)amino]carbonyl}cyclopentyl)methyl]pentanoate

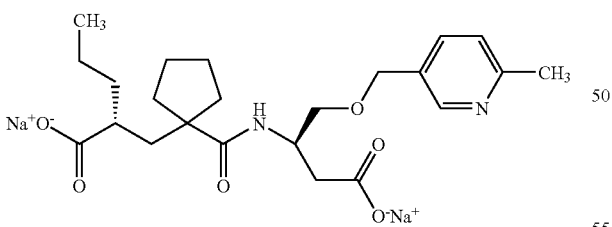

A solution of the ester from preparation 53 (40 mg, 0.07 mmol) and 1N sodium hydroxide solution (210 μl, 0.21 mmol) in dioxan (0.6 ml) was stirred at room temperature for 2 hours. The mixture was evaporated under reduced pressure and the residue azeotroped with toluene to afford the title compound, 40 mg. $^1$H NMR (CD$_3$OD, 400 MHz) δ: 0.82 (t, 3H), 1.25 (m, 3H), 1.42–1.64 (m, 7H), 1.76 (dd, 1H), 1.98 (m, 2H), 2.08 (m, 1H), 2.18 (m, 1H), 2.42 (m, 2H), 2.50 (s, 3H), 3.60 (m, 2H), 4.41 (m, 1H), 4.58 (q, 2H), 7.25 (d, 1H), 7.78 (d, 1H), 8.38 (s, 1H). HRMS: m/z (ES$^+$) 435.2488 [MH$^+$] C$_{23}$H$_{34}$N$_2$O$_6$ requires 435.2490.

Example 10

(2S)-2-[(1-{[((1S)-2-Carboxy-1-{[(3-methoxybenzyl)oxy]methyl}ethyl)amino]-carbonyl}cyclopentyl)methyl]-4-methoxybutanoic Acid

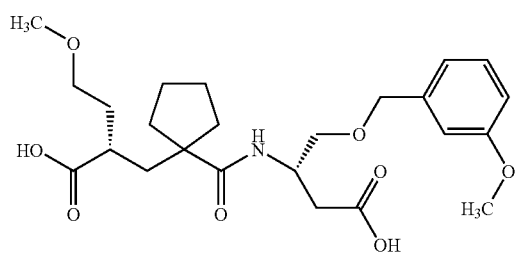

Trifluoroacetic acid (1 ml) was added to a solution of the tert-butyl ester from preparation 17 (26 mg, 0.05 mmol) in dichloromethane (4 ml), and the reaction stirred at room temperature for 18 hours. The solution was concentrated under reduced pressure and the trifluoroacetic acid removed by azeotrope with toluene, ethyl acetate and dichloromethane to afford the title compound as a colourless oil, 17 mg. $^1$H NMR (CDCl$_3$+drop D$_2$O, 400 MHz, rotamers) δ: 1.23–2.15 (m, 12H), 2.48 (m, 1H), 2.63 (m, 2H), 3.30 (2×s, 3H), 3.39 (m, 2H), 3.57 (m, 2H), 3.79 (m, 3H), 4.21 (m, 1H), 4.47 (m, 2H), 6.57, 6.60 (2×d, 1H), 6.82 (m, 3H), 7.22 (m, 1H). HRMS: m/z (ES$^+$) 466.2450 [MH$^+$] C$_{24}$H$_{35}$NO$_8$ requires 466.2436.

Examples 11 to 15

The following examples of general formula:

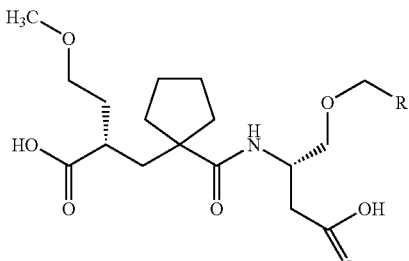

were obtained quantitatively from the corresponding tert-butyl esters, following a similar procedure to that described in Example 10.

| Ex. No | R | Data |
|---|---|---|
| 11 | ![4-chlorophenyl] | $^1$H NMR(CDCl$_3$ + D$_2$O, 400MHz, rotamers)δ: 1.45–1.76(m, 6H), 1.79–2.14(m, 6H), 2.48(m, 1H), 2.63(m, 2H), 3.30(d, 3H), 3.33–3.60(m, 4H), 4.48(m, 3H), 6.45, 6.56(2xd, 1H), 7.23(m, 2H), 7.32(m, 2H). HRMS: m/z(ES) 470.1956[MH$^+$] C$_{23}$H$_{32}$ClNO$_7$ requires 470.1940[MH$^+$] |

| Ex. No | R | Data |
|---|---|---|
| 12 |  | ¹H NMR(CDCl₃ + D₂O, 400MHz)δ: 1.48–1.76(m, 7H), 1.79–1.97(m, 3H), 2.00–2.16(m, 2H), 2.52(m, 1H), 2.75(d, 2H), 3.34(s, 3H), 3.40(m, 2H), 3.62(m, 2H), 4.57(m, 1H), 4.61(s, 2H), 7.22(m, 2H), 7.39(m, 2H). HRMS: m/z(ES) 470.1947[MH⁺] $C_{23}H_{32}ClNO_7$ requires 470.1940[MH⁺] |
| 13 | 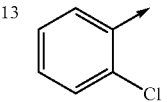 | ¹H NMR(CDCl₃ + D₂O, 400MHz)δ: 1.45–1.77(m, 7H), 1.83(m, 3H), 2.00–2.17(m, 2H), 2.50(m, 1H), 2.68(d, 2H), 3.32(s, 3H), 3.40(m, 2H), 3.58(m, 2H), 4.50(m, 3H), 7.18(m, 1H), 7.26(m, 3H); HRMS: m/z(ES) 470.1944[MH⁺] $C_{23}H_{32}ClNO_7$ requires 470.1940[MH⁺] |
| 14 | 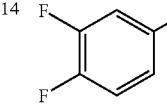 | ¹H NMR(CDCl₃, 400MHz)δ: 1.44–1.74(m, 6H), 1.78–193(m, 4H), 1.99–2.16(m, 2H), 2.48(m, 1H), 2.70(d, 2H), 3.30(s, 3H), 3.40(m, 2H), 3.57(m, 2H), 4.46(m, 3H), 6.62(d, 1H), 6.99(m, 1H), 7.12(m, 2H), 8.36(br, s, 2H). HRMS: m/z(ES) 472.2144[MH⁺] $C_{23}H_{31}F_2NO_7$ requires 472.2142[MH⁺] |
| 15 | 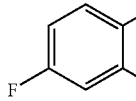 | ¹H NMR(CDCl₃, 400MHz)δ: 1.42–1.76(m, 8H), 1.84(m, 2H), 1.99–2.18(m, 2H), 2.46(m, 1H), 2.62(m, 2H), 3.26(s, 3H), 3.39(m, 2H), 3.57(m, 2H), 4.50(m, 3H), 6.58(d, 1H), 6.76–6.86(m, 2H), 7.30(m, 1H). HRMS: m/z (ES) 472.2143[MH⁺] $C_{23}H_{31}F_2NO_7$ requires 472.2142[MH⁺] |

Example 16

(2S)-2-[(1-{[((1R)-2-Carboxy-1-{[(4-chlorobenzyl)oxy]methyl}ethyl)amino]-carbonyl}cyclopentyl)methyl]-4-methoxybutanoic Acid

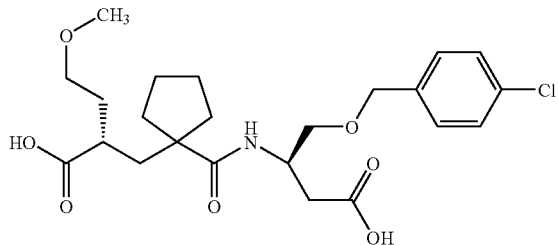

A solution of the ester from preparation 23 (100 mg, 0.19 mmol) and trifluoroacetic acid (1 ml) in dichloromethane (5 ml) was stirred at room temperature for 18 hours. The mixture was concentrated under reduced pressure and azeotroped with toluene. The residue was partitioned between dichloromethane and water, the layers separated, and the organic phase dried (MgSO₄) and evaporated under reduced pressure to afford the title compound as a colourless oil, 73 mg. ¹H NMR (CDCl₃, 400 MHz) δ: 1.45–1.78 (m, 7H), 1.81–2.02 (m, 4H), 2.18 (m, 1H), 2.47–2.75 (m, 3H), 3.38 (m, 4H), 3.57 (m, 3H), 4.46 (s, 2H), 4.73 (m, 1H), 6.40, 6.58 (2×d, 1H), 7.21 (d, 2H), 7.30 (d, 2H).

Example 17

(2R)-2-({1-[({(1S)-1-[(Benzyloxy)methyl]-3-ethoxy-3-oxopropyl}amino)carbonyl]-cyclopentyl}methyl)pentanoic Acid

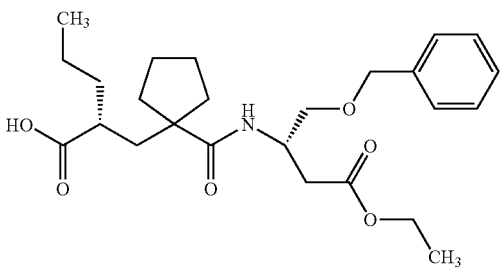

A solution of the ester from preparation 46 (110 mg, 0.22 mmol) in trifluoroacetic acid (0.5 ml) and dichloromethane (5 ml) was stirred at room temperature for 72 hours. The reaction was concentrated under reduced pressure and the residue azeotroped with toluene and dichloromethane to afford the title compound, 95 mg. ¹H NMR (CDCl₃, 400 MHz) δ: 0.90 (t, 3H), 1.20–1.43 (m, 6H), 1.50–1.78 (m, 7H), 2.00 (m, 3H), 2.39 (m, 2H), 2.62 (m, 2H), 3.59 (m, 2H), 4.10 (q, 2H), 4.50 (m, 3H), 6.77 (d, 1H), 7.35 (m, 5H).

LRMS: m/z (ES⁺) 448.5 [MH⁺].

Example 18

(2R)-2-[(1-{[((1S)-3-Ethoxy-1-{[(3-methoxybenzyl)oxy]methyl}-3-oxopropyl)amino]-carbonyl}cyclopentyl)methyl]pentanoic Acid

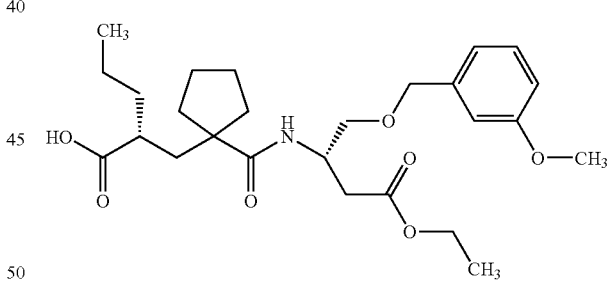

Trifluoroacetic acid (1 ml) was added to a solution of the ester from preparation 24 (280 mg, 0.53 mmol) in dichloromethane (5 ml), and the solution stirred at room temperature for 4 hours. The reaction was concentrated under reduced pressure and the residue azeotroped with ethyl acetate. The crude product was purified by column chromatography on silica gel using dichloromethane:methanol (98:2) to afford the title compound as a colourless oil. ¹H NMR (CDCl₃, 400 MHz) δ: 0.86 (t, 3H), 1.23 (t, 3H), 1.34 (m, 3H), 1.50–1.76 (m, 8H), 2.00 (m, 3H), 2.38 (m, 1H), 2.62 (m, 2H), 3.58 (m, 2H), 3.81 (s, 3H), 4.14 (q, 2H), 4.45 (m, 3H), 6.62 (d, 1H), 6.84 (m, 3H), 7.24 (m, 1H).

$[\alpha]_D$=−2.13° (c=0.3, methanol) Microanalysis found: C, 65.10; H, 8.29; N, 3.01. $C_{26}H_{39}NO_7$ requires C, 65.39; H, 8.23; N, 2.93%.

Example 19

(2R)-2-[(1-{[((1S)-1-{[(4-Chlorobenzyl)oxy]methyl}-3-ethoxy-3-oxopropyl)amino]-carbonyl}cyclopentyl)methyl]pentanoic Acid

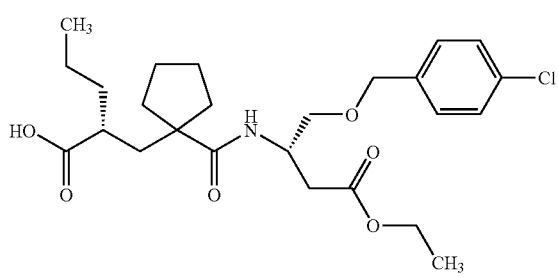

Trifluoroacetic acid (1.2 ml) was added to a solution of the ester from preparation 25 (175 mg, 0.33 mmol) in dichloromethane (10 ml), and the solution stirred at room temperature for 18 hours. The mixture was concentrated under reduced pressure and the residue azeotroped with toluene (3×20 ml), ethyl acetate (20 ml), and dichloromethane (20 ml). The crude product was purified by column chromatography on silica gel using an elution gradient of dichloromethane:methanol (98:2 to 95:5) to give the title compound as a colourless oil. $^{1}$H NMR (CDCl$_3$, 400 MHz) δ: 0.87 (t, 3H), 1.21–1.41 (m, 6H), 1.49–1.78 (m, 8H), 2.00 (m, 3H), 2.38 (m, 1H), 2.62 (m, 2H), 3.57 (m, 2H), 4.14 (q, 2H), 4.45 (m, 3H), 6.60 (d, 1H), 7.23 (m, 2H), 7.35 (d, 2H). HRMS: m/z (ES$^+$) 482.2314 [MH$^+$] C$_{25}$H$_{36}$ClNO$_6$ requires 482.2306; [α]$_D$=–13.2° (c=0.1, methanol).

Examples 20 to 24

The following examples of general formula:

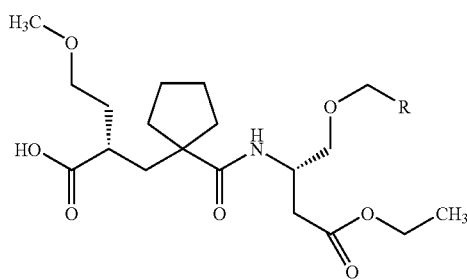

were obtained, from the corresponding tert-butyl esters, following a similar procedure to that described in Example 19.

| Ex. No | R | Data |
|---|---|---|
| 20 | 4-Cl-C$_6$H$_4$ | $^1$H NMR(CDCl$_3$, 400MHz)δ: 1.22(t, 3H), 1.52–1.75(m, 8H), 1.99(m, 3H), 2.10(dd, 1H), 2.56(m, 1H), 2.61(m, 2H), 3.26(s, 3H), 3.38(m, 2H), 3.57(m, 2H), 4.10(q, 2H), 4.45(m, 3H), 6.63(d, 1H), 7.22(d, 2H), 7.32(d, 2H); LRMS: m/z(APCI) 498[MH$^+$] |
| 21 | 3-Cl-C$_6$H$_4$ | $^1$H NMR(CDCl$_3$, 400MHz)δ: 1.22(t, 3H), 1.50–1.75(m, 8H), 1.88–2.10(m, 4H), 2.54(m, 1H), 2.64(m, 2H), 3.26(s, 3H), 3.38(m, 2H), 3.62(m, 2H), 4.09(q, 2H), 4.48(m, 1H), 4.60(s, 2H), 6.74(d, 1H), 7.22(m, 2H), 7.38(d, 1H), 7.40(d, 1H); HRMS: m/z(ES$^+$) 498.2261[MH$^+$] C$_{25}$H$_{36}$ClNO$_7$ requires 498.2253 |
| 22 | 2-Cl-C$_6$H$_4$ | $^1$H NMR(CDCl$_3$, 400MHz)δ: 1.22(t, 3H), 1.54–1.76(m, 8H), 1.88–2.14(m, 4H), 2.52(m, 1H), 2.62(m, 2H), 3.24(s, 3H), 3.38(m, 2H), 3.58(m, 2H), 4.18(q, 2H), 4.44(m, 3H), 6.74(d, 1H), 7.18(m, 1H), 7.25(m, 3H). HRMS: m/z (ES$^+$) 498.2255[MH$^+$] C$_{25}$H$_{36}$ClNO$_7$ requires 498.2253 |
| 23[a] | 2,4-diF-C$_6$H$_3$ | $^1$H NMR(CDCl$_3$, 400MHz)δ: 1.22(t, 3H), 1.52–1.76(m, 8H), 1.98(m, 3H), 2.05(m, 1H), 2.50(m, 1H), 2.60(m, 2H), 326(s, 3H), 3.38(m, 2H), 3.58(m, 2H), 4.07(q, 2H), 4.43(m, 1H), 4.52(s, 2H), 6.68(d, 1H), 6.78–6.90(m, 2H), 7.35(m, 1H); HRMS: m/z(ES$^+$) 500.2451[MH$^+$] C$_{25}$H$_{35}$F$_2$NO$_7$ requires 500.2455 |
| 24 | 3,4-diF-C$_6$H$_3$ | $^1$H NMR (CDCl$_3$, 400MHz)δ: 1.22(t, 3H), 1.50–1.74(m, 8H), 1.98(m, 3H), 2.07(dd, 1H), 2.56(m, 1H), 2.61(m, 2H), 3.26(s, 3H), 3.38(m, 2H), 3.58(m, 2H), 4.12(q, 2H), 4.43(m, 3H), 6.66(d, 1H), 7.00(m, 1H), 7.14(m, 2H); HRMS: m/z(ES$^+$) 500.2458[MH$^+$] C$_{25}$H$_{35}$F$_2$NO$_7$ requires 500.2455 |

[a]isolated without column chromatography

Example 25

(2R)-2-[(1-{[((1R)-1-{[(4-Chlorobenzyl)oxy]methyl}-3-ethoxy-3-oxopropyl)amino]-carbonyl}cyclopentyl)methyl]pentanoic Acid

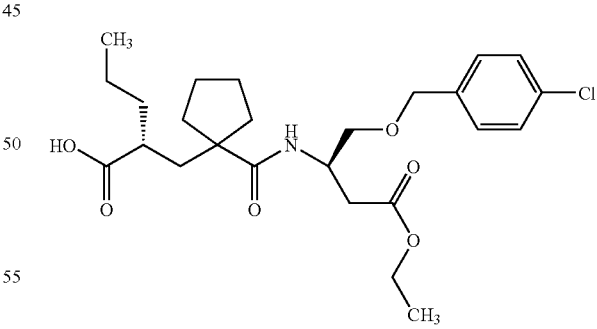

A solution of the ester from preparation 99 (98 mg, 0:18 mmol) and trifluoroacetic acid (2 ml) in dichloromethane (4 ml) was stirred at room temperature for 18 hours. The mixture was concentrated under reduced pressure and the residue azeotroped with dichloromethane to afford the title compound, 73 mg. $^1$H NMR (CDCl$_3$, 400 MHz) δ: 0.87 (t, 3H), 1.21–1.41 (m, 6H), 1.50–1.78 (m, 8H), 1.96 (m, 1H), 2.02 (m, 2H), 2.38 (m, 1H), 2.60 (m, 2H), 3.57 (m, 2H), 4.10

(q, 2H), 4.45 (m, 3H), 6.58 (d, 1H), 7.23 (m, 2H), 7.35 (d, 2H); HRMS: m/z (ES$^+$) 504 [MNa$^+$]; [α]$_D$=+10.00 (c=0.11, methanol).

Example 26

(2R)-2-{[1-({[(1S)-1-[(Benzyloxy)methyl]-3-(2-butoxyethoxy)-3-oxopropyl]amino}-carbonyl)cyclopentyl]methyl}pentanoic Acid

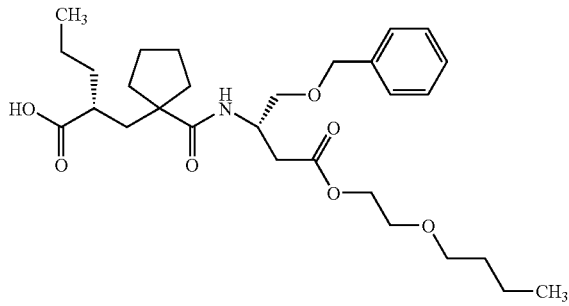

A solution of the ester from preparation 50 (100 mg, 0.17 mmol) in trifluoroacetic acid (0.3 ml) and dichloromethane (3 ml) was stirred at room temperature for 18 hours, and then evaporated under reduced pressure to afford the title compound.

$^1$H NMR (CDCl$_3$, 400 MHz) δ:0.88 (m, 6H), 1.30 (m, 5H), 1.48–1.74 (m, 9H), 1.93 (m, 1H), 1.99–2.16 (m, 2H), 2.38 (m, 1H), 2.68 (d, 2H), 3.45 (m, 3H), 3.58 (m, 2H), 3.61 (m, 2H), 4.17 (m, 1H), 4.23 (m, 1H), 4.50 (m, 3H), 6.59 (d, 1H), 7.22 (m, 5H); LRMS: m/z (ES$^-$) 518 [M-H]$^-$.

Example 27

(2R)-2-({1-[({(1S)-1-[(Benzyloxy)methyl]-3-oxo-3-[2-oxo-2-(1-piperidinyl)ethoxy]-propyl}amino)carbonyl]cyclopentyl}methyl)pentanoic Acid

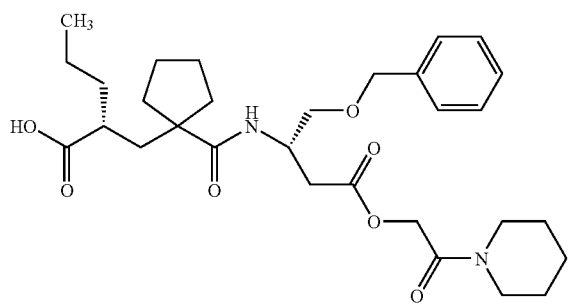

A solution of the ester from preparation 51 (100 mg, 0.16 mmol) in trifluoroacetic acid (0.3 ml) and dichloromethane (3 ml) was stirred at room temperature for 18 hours, and concentrated under reduced pressure. The residue was azeotroped with toluene, and the crude product then purified by column chromatography on silica gel using dichloromethane:methanol (98:2 to 95:5) to afford the title compound, 30 mg. $^1$H NMR (CDCl$_3$, 400 MHz) δ: 0.85 (t, 3H), 1.24–1.78 (m, 17H), 1.90 (m, 1H), 1.99 (dd, 1H), 2.18 (m, 1H), 2.37 (m, 1H), 2.80 (d, 2H), 3.25 (m, 2H), 3.50 (m, 1H), 3.60 (m, 3H), 4.50 (s, 2H), 4.61 (m, 2H), 4.78 (d, 1H), 6.63 (d, 1H), 7.28 (m, 5H); LRMS: m/z (ES$^-$) 543 [M-H]$^-$.

Example 28

(2R)-2-{[1-({[(1R)-3-Ethoxy-3-oxo-1-(2-phenoxyethyl)propyl]amino}carbonyl)-cyclopentyl]methyl}pentanoic Acid

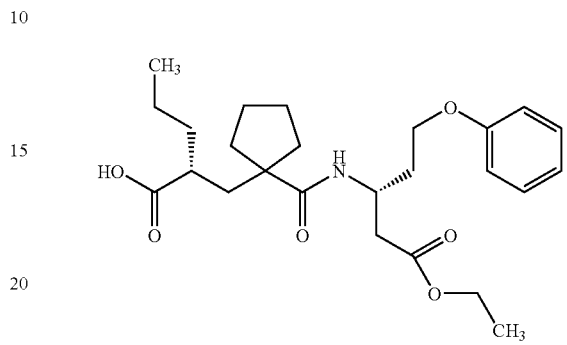

Trifluoroacetic acid (1 ml) was added to a solution of the ester from preparation 67 (60 mg, 0.12 mmol) in dichloromethane (5 ml), and the solution stirred at room temperature for 18 hours. The mixture was concentrated under reduced pressure, the residue dissolved in dichloromethane, washed with water, dried (MgSO$_4$) and evaporated under reduced pressure to afford the title compound, 40 mg. $^1$H-NMR (CDCl$_3$, 400 MHz) δ: 0.83 (t, 3H), 1.26 (m, 8H), 1.55–1.77 (m, 7H), 2.00 (m, 2H), 2.10 (m, 2H), 2.35 (m, 1H), 2.65 (m, 2H), 4.02 (m, 2H), 4.17 (q, 2H), 4.48 (m, 1H), 6.86 (m, 3H), 6.99 (m, 1H), 7.25 (m, 2H).

Examples 29 to 30

The compounds of the following general formula:

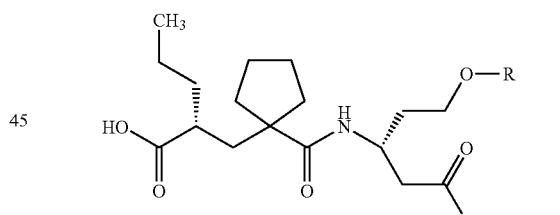

were prepared from the corresponding tert-butyl esters, following a similar procedure to that described in Example 28.

| Ex. No | R | Data |
|---|---|---|
| 29 | 4-F-C$_6$H$_4$-CH$_2$- | $^1$H-NMR(CDCl$_3$, 400MHz)δ: 0.85(t, 3H), 1.26(m, 6H), 1.48–1.75(m, 8H), 1.95–2.22(m, 5H), 2.37(m, 1H), 2.62(m, 2H), 3.99(m, 2H), 4.18(q, 2H), 4.45(m, 1H), 6.77(d, 1H), 6.80(m, 2H), 6.98(dd, 2H). LRMS: m/z(ES$^+$) 488[MNa$^+$] |

-continued

| Ex. No | R | Data |
|---|---|---|
| 30 | 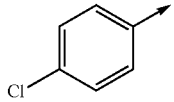 | $^1$H-NMR(CDCl$_3$, 400MHz)δ: 0.85(t, 3H), 1.28(m, 6H), 1.50–1.77(m, 8H), 1.92–2.14(m, 5H), 2.34(m, 1H), 2.64(d, 2H), 4.00(t, 2H), 4.18(q, 2H), 4.42(m, 1H), 6.80(d, 2H), 6.96(d, 1H), 7.22(d, 2H). LRMS: m/z(ES$^+$) 504[MNa$^+$] |

Example 31

(2R)-2-{[1-({[(1S)-2-(Benzyloxy)-1-(carboxymethyl)ethyl]amino}carbonyl)-cyclopentyl]methyl}pentanoic Acid

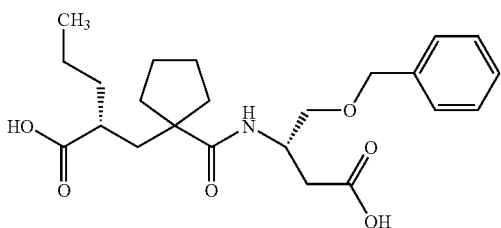

A solution of the ethyl ester from example 17 (70 mg, 0.16 mmol) in sodium hydroxide solution (1 ml, 1N) and methanol (5 ml) was stirred at room temperature for 18 hours. The reaction was concentrated under reduced pressure to remove the methanol, and the residue was partitioned between ethyl acetate (10 ml) and hydrochloric acid (2N, 10 ml). The phases were separated, the aqueous layer extracted with ethyl acetate (4×10 ml), the combined organic solutions washed with brine (10 ml), dried (MgSO$_4$) and evaporated under reduced pressure to afford the title compound, 50 mg; $^1$H NMR (CDCl$_3$, 400 MHz) δ: 0.92 (t, 3H), 1.23–2.39 (m, 15H), 2.74 (d, 2H), 3.60 (m, 2H), 4.52 (m, 3H), 6.66 (d, 1H), 7.35 (m, 5H); HRMS: m/z (ES$^+$) 420.2374 [MH$^+$]; C$_{23}$H$_{33}$NO$_6$ calculated 420.2381.

Example 32

(2R)-2-[(1-{[((1S)-2-Carboxy-1-{[(3-methoxybenzyl)oxy]methyl}ethyl)amino]carbonyl}-cyclopentyl)methyl]pentanoic Acid

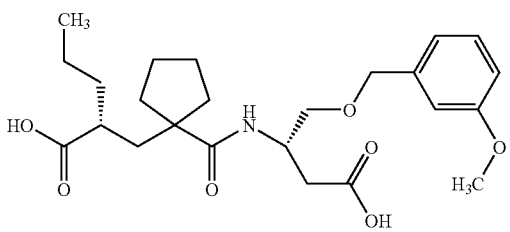

Sodium hydroxide solution (1 ml, 1N, 1 mmol) was added to a solution of the ethyl ester from example 18 (50 mg, 0.11 mmol) in dioxan (3 ml), and the reaction stirred at room temperature for 2 hours. The reaction was concentrated under reduced pressure, the residue dissolved in water, acidified using 2N hydrochloric acid, and extracted into ethyl acetate. The combined organic extracts were dried (MgSO$_4$) and evaporated under reduced pressure to afford the title compound, 30 mg; $^1$H NMR (CDCl$_3$, 400 MHz) δ: 0.86 (t, 3H), 1.23–1.66 (m, 10H), 1.78 (m, 1H), 1.85 (m, 1H), 1.98 (dd, 1H), 2.14 (m, 1H), 2.39 (m, 1H), 2.72 (d, 2H), 3.58 (m, 2H), 3.80 (s, 3H), 4.46 (m, 3H), 6.58 (d, 1H), 6.84 (m, 3H), 7.23 (m, 1H); LRMS: m/z (ES$^-$) 448 [M-H]$^-$.

Examples 33 to 40

The compounds of the following general structure:

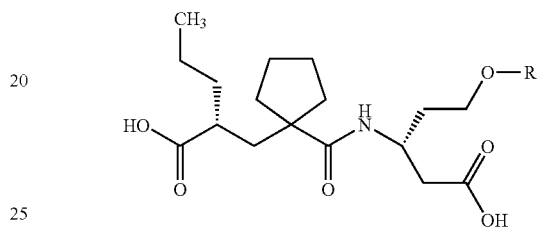

were prepared from the corresponding ethyl esters, following a similar procedure to that described in Example 32.

| Ex. No | R | Data |
|---|---|---|
| 33 | 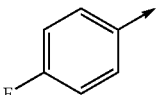 | $^1$H-NMR(CDCl$_3$, 400MHz)δ: 0.84(t, 3H), 1.30–1.74(m, 9H), 1.90(m, 3H), 2.17(m, 4H), 2.37(m, 1H), 2.78(m, 2H), 4.02(m, 2H), 4.56(m, 1H), 6.59(d, 1H), 6.90(m, 2H), 6.99(m, 1H), 7.24(m, 2H). LRMS: m/z(ES$^-$) 418[M-H]$^-$ |
| 34 | 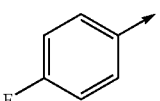 | $^1$H-NMR(CDCl$_3$, 400MHz)δ: 0.84(t, 3H), 1.24–1.70(m, 9H), 1.86(m, 3H), 2.16(m, 4H), 2.34(m, 1H), 2.70(dd, 1H), 2.80(dd, 1H), 3.99(dd, 2H), 4.50(m, 1H), 6.68(d, 1H), 6.81(m, 2H), 6.98(m, 2H). LRMS: m/z(ES$^+$) 460[MNa$^+$] |
| 35 | 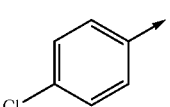 | $^1$H-NMR(CDCl$_3$, 400MHz)δ: 0.86(t, 3H), 1.21–1.74(m, 9H), 1.86(m, 3H), 2.16(m, 4H), 2.27(m, 1H), 2.70(dd, 1H), 2.82(dd, 1H), 3.98(dd, 2H), 4.54(m, 1H), 6.72(d, 1H), 6.81(d, 2H), 7.22(d, 2H). LRMS: m/z(ES$^+$) 454[MH$^+$] |
| 36 | 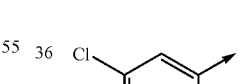 | $^1$H-NMR(CDCl$_3$, 400MHz)δ: 0.85(t, 3H), 1.22–1.77(m, 9H), 1.84(m, 3H), 2.17(m, 4H), 2.29(m, 1H), 2.70(dd, 1H), 2.81(dd, 1H), 4.00(dd, 2H), 4.55(m, 1H), 6.76(m, 2H), 6.86(s, 1H), 6.94(d, 1H), 7.18(dd, 1H). LRMS: m/z(ES$^-$) 452[M-H]$^-$ |
| 37 |  | $^1$H-NMR(CDCl$_3$, 400MHz)δ: 0.84(t, 3H), 1.20–1.99(m, 13H), 2.16(m, 3H), 2.34(m, 1H), 2.74(m, 2H), 3.77(s, 3H), 4.02(m, 2H), 4.40(m, 1H), 6.76(d, 1H), 6.80(s, 4H). |

-continued

| Ex. No | R | Data |
|---|---|---|
| 38 | 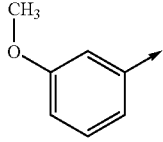 | ¹H-NMR(CDCl₃, 400MHz)δ: 0.85(t, 3H), 1.22–1.74(m, 10H), 1.96(m, 3H), 2.17(m, 3H), 2.32(m, 1H), 2.70(dd, 1H), 2.80(dd, 1H), 3.79(s, 3H), 4.00(m, 2H), 4.50(m, 1H), 6.46(m, 3H), 6.78(d, 1H), 7.18(dd, 1H); HRMS: m/z(ES⁺) 450.2488[MH⁺]; $C_{24}H_{35}NO_7$ gives 450.2487 |
| 39 | 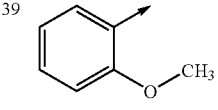 | ¹H-NMR(CDCl₃, 400MHz)δ: 0.83(t, 3H), 1.22–1.39(m, 3H), 1.41–1.65(m, 7H), 1.76(dd, 1H), 1.90–2.21(m, 5H), 2.37(m, 1H), 2.71(dd, 1H), 2.79(dd, 1H), 3.83(s, 3H), 4.08(m, 2H), 4.50(m, 1H), 6.90(m, 4H), 7.02(d, 1H), 8.84(br s, 2H); HRMS: m/z(ES⁺) 450.2490[MH⁺] $C_{24}H_{35}NO_7$ gives 450.2487 |
| 40 | 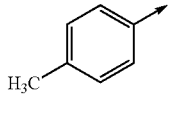 | ¹H-NMR(CDCl₃, 400MHz)δ: 0.83(t, 3H), 1.22–1.72(m, 10H), 1.86(m, 4H), 2.17(m, 4H), 2.30(m, 4H), 2.75(m, 2H), 4.00 4.50(m, 1H), 6.78(m, 3H), 7.05(d, 2H); LRMS: m/z(ES⁺) 456[MNa⁺] |

Example 41

(3S)-3-[({1-[(2R)-2-Carboxypentyl] cyclopentyl}carbonyl)amino]-5-(4-chlorophenoxy) pentanoic Acid

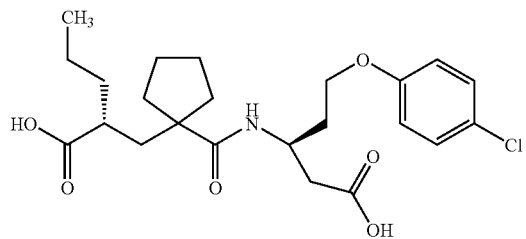

A mixture of the ethyl ester from preparation 86 (180 mg, 0.37 mmol) and sodium hydroxide solution (2N, 2 ml) in dioxan (5 ml) was stirred at 50° C. for 5 hours, then at room temperature for a further 18 hours. The mixture was concentrated under reduced pressure, the residue acidifed using 2N hydrochloric acid, and extracted with ethyl acetate (2×20 ml). The combined organic solutions were dried (MgSO₄), concentrated under reduced pressure and the residue purified by column chromatography on silica gel using an elution gradient of dichloromethane:methanol:acetic acid (95:5:0 to 90:10:0 to 90:10:1) to afford the title compound as a colourless oil, 150 mg. ¹H-NMR (CDCl₃, 400 MHz) δ: 0.84 (t, 3H), 1.26 (m, 3H), 1.40–1.80 (m, 6H), 1.97 (m, 2H), 2.10 (m, 5H), 2.37 (m, 1H), 2.61 (dd, 1H), 2.78 (dd, 1H), 4.00 (m, 2H), 4.42 (m, 1H), 6.80 (d, 2H), 6.98 (d, 2H), 7.20 (d, 2H). LRMS: m/z (ES⁻) 452 [M-H⁻].

Example 42

(3S)-3-[({1-[(2R)-2-Carboxypentyl] cyclopentyl}carbonyl)amino]-5-(4-fluorophenoxy)- pentanoic Acid

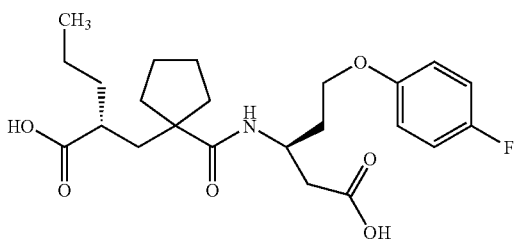

A mixture of the ester from preparation 87 (130 mg, 0.28 mmol) in sodium hydroxide solution (3 ml, 2N) and dioxan (6 ml) was stirred at 50° C. for 3 hours. The reaction mixture was concentrated under reduced pressure, the residue acidified using 2N hydrochloric acid and extracted with ethyl acetate (3×50 ml).

The crude product was purified by column chromatography on silica gel using an elution gradient of methanol: dichloromethane (5:95 to 10:90) to afford the title compound as a colourless oil, 58 mg; ¹H-NMR (CDCl₃+1 drop TFAd, 400 MHz) δ: 0.83 (t, 3H), 1.23 (m, 2H), 1.39 (m, 1H), 1.55–1.78 (m, 8H), 1.82 (m, 1H), 1.98 (m, 1H), 2.16 (m, 3H), 2.38 (m, 1H), 2.79 (m, 2H), 4.05 (t, 2H), 4.58 (m, 1H), 6.82 (m, 2H), 7.00 (m, 2H), 7.18 (d, 1H); LRMS: m/z (ES⁻) 436 [M-H]⁻; Microanalysis found: C, 59.87; H, 7.11; 3.02. $C_{23}H_{32}FNO_6$; $0.4CH_2Cl_2$ requires C, 59.61; H, 7.01; N, 2.97%.

Examples 43 to 45

The following examples of general formula:

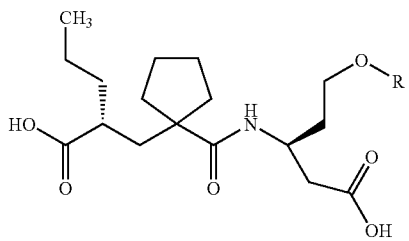

were prepared from the corresponding ethyl esters following a similar procedure to that described in Example 42.

| Ex. No | R | Data |
|---|---|---|
| 43 |  | ¹H-NMR(CDCl₃, 400MHz)δ: 0.82(t, 3H), 1.24(m, 3H), 1.40–1.80(m, 8H), 1.98(m, 2H), 2.16(m, 3H), 2.37(m, 1H), 2.62(m, 1H), 2.79(m, 1H), 4.02(m, 2H), 4.43(m, 1H), 6.62(m, 3H), 7.01(m, 1H), 7.20(m, 1H); LRMS: m/z(ES⁺) 460[MNa]⁺; [α]_D=−17.15(c=0.07, methanol) |

-continued

| Ex. No | R | Data |
|---|---|---|
| 44[a] | 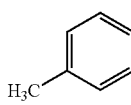 | ¹H-NMR(CDCl₃, 400MHz)δ: 0.84(t, 3H), 1.26(m, 3H), 1.42–1.70(m, 7H), 1.78(dd, 1H), 1.98(m, 2H), 2.16(m, 3H), 2.26(s, 3H), 2.39(m, 1H), 2.60(dd, 1H), 2.80(dd, 1H), 4.02(m, 2H), 4.42(m, 1H), 6.78(d, 2H), 7.04(m, 3H); LRMS: m/z(ES⁻) 432[M–H]⁻ |
| 45[a] | 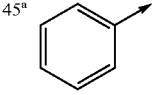 | ¹H-NMR(CDCl₃, 400MHz)δ: 0.84(t, 3H), 1.26(m, 3H), 1.42–1.80(m, 8H), 1.98(m, 3H), 2.18(m, 2H), 2.38(m, 1H), 2.62(dd, 1H), 2.80(dd, 1H), 4.04(m, 2H), 4.42(m, 1H), 6.85(d, 2H), 6.97(m, 1H), 7.04(d, 1H), 7.25(d, 2H); LRMS: m/z(ES⁺) 420[MH⁺]; [α]_D=−19.20 (c=0.10, methanol) |

[a]product purified by reverse phase HPLC using acetonitrile:water:trifluoroacetic acid as eluant Example 46

(3R)-3-[({1-[(2S)-2-Carboxy-4-methoxybutyl]cyclopentyl}carbonyl)amino]-5-(4-chlorophenoxy)pentanoic Acid

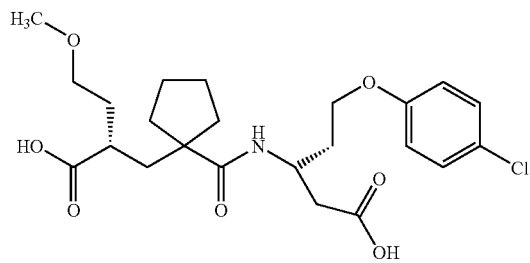

A solution of the ester from preparation 80 (295 mg, 0.51 mmol) in trifluoroacetic acid (1 ml) and dichloromethane (4 ml) was stirred at room temperature for 4 hours. The solution was concentrated under reduced pressure and then azeotroped with toluene. The residue was partitioned between saturated sodium bicarbonate solution and dichloromethane, the layers separated and the aqueous extracted with dichloromethane. The pH of the aqueous solution was adjusted to 1 using hydrochloric acid (2N), and this was then extracted with dichloromethane (3×). These combined organic extracts were dried (MgSO₄) and evaporated under reduced pressure to afford the title compound as a colourless solid, 134 mg; ¹H-NMR (CDCl₃, 400 MHz) δ: 1.40–1.74 (m, 7H), 1.80–1.99 (m, 4H), 2.08 (m, 3H), 2.41 (m, 1H), 2.63 (dd, 1H), 2.78 (dd, 1H), 3.24 (s, 3H), 3.38 (m, 2H), 3.98 (s, 2H), 4.55 (m, 1H), 6.62 (m, 1H), 6.78 (d, 2H), 7.20 (d, 2H); LRMS: m/z (ES⁻) 468 [M-H]⁻; Microanalysis found: C, 57.76; H, 6.88; N, 3.03. C₂₃H₃₂ClNO₇; 0.5H₂O requires C, 57.68; H, 6.94; N, 2.92%.

Example 47

Ethyl (3S)-3-[({1-[(2S)-2-Carboxy-4-methoxybutyl]cyclopentyl}carbonyl)amino]-5-(4-chlorophenoxy)pentanoate

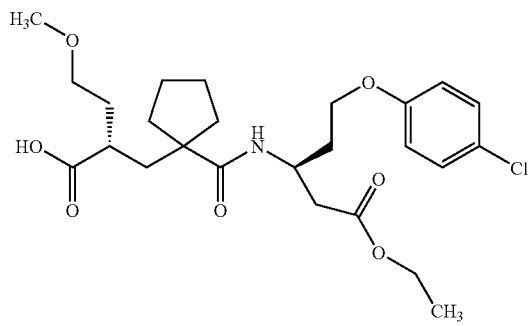

A solution of the ester from preparation 81 (300 mg, 0.54 mmol) and trifluoroacetic acid (5 ml) in dichloromethane (5 ml) was stirred at room temperature for 2 hours. The mixture was concentrated under reduced pressure and the residue azeotroped with toluene. The crude product was purified by column chromatography on reverse phase silica gel using an elution gradient of acetonitrile:water:trifluoroacetic acid (5:95:0.1 to 95:5:0) to afford the title compound as a colourless oil, 109 mg; ¹H NMR (CDCl₃, 400 MHz) δ: 1.28 (t, 3H), 1.54–1.75 (m, 8H), 1.98 (m, 3H), 2.06 (m, 3H), 2.50 (m, 1H), 2.63 (m, 2H), 3.25 (s, 3H), 3.38 (m, 2H), 4.00 (t, 2H), 4.18 (q, 2H), 4.43 (m, 1H), 6.81 (m, 3H), 7.22 (d, 2H); LRMS: m/z (ES⁻) 496 [M-H]⁻.

Example 48

(3S)-3-[({1-[(2S)-2-Carboxy-4-methoxybutyl]cyclopentyl}carbonyl)amino]-5-(4-chlorophenoxy)pentanoic Acid

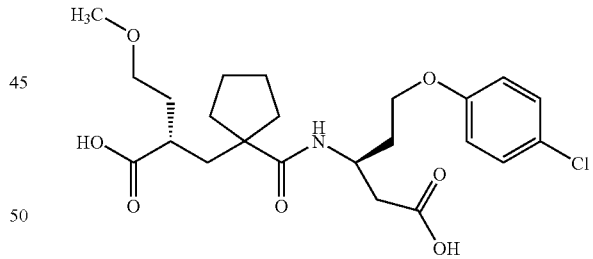

A solution of the ethyl ester from example 47 (100 mg, 0.20 mmol) and 2N sodium hydroxide solution (2 ml) in dioxan (4 ml) was stirred at 50° C. for 3 hours, then concentrated under reduced pressure. The residue was suspended in 2N hydrochloric acid (2 ml), extracted with ethyl acetate (3×20 ml), and the combined organic solutions dried (MgSO₄) and evaporated under reduced pressure. The crude product was purified by column chromatography on silica gel using an elution gradient of ethyl acetate:methanol:acetic acid (90:10:0 to 90:10:1) to afford the title compound as a colourless oil, 50 mg; ¹H NMR (CDCl₃, 400 MHz) δ: 1.45–1.78 (m, 8H), 1.85–2.19 (m, 6H), 2.56 (m, 1H), 2.62 (m, 2H), 3.37 (m, 4H), 3.46 (m, 1H), 4.00 (t, 2H), 4.62 (m, 1H), 6.64 (d, 1H), 6.81 (d, 2H), 7.22 (d, 2H); LRMS: m/z (ES⁻) 468 [M-H]⁻.

Example 49

(2S)-2-({1-[({(1S)-3-Butoxy-1-[2-(4-chlorophenoxy)ethyl]-3-oxopropyl}amino)carbonyl]-cyclopentyl}methyl)-4-methoxybutanoic Acid

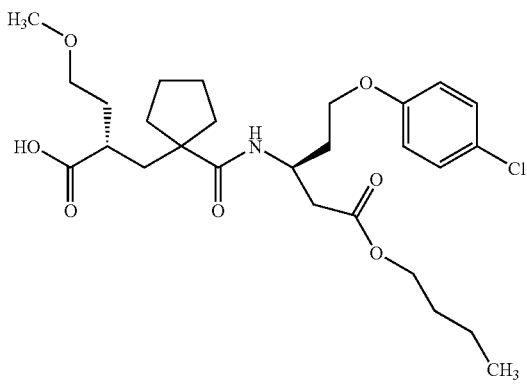

A solution of the ester from preparation 92 (278 mg, 0.48 mmol) and trifluoroacetic acid (3 ml) in dichloromethane (5 ml) was stirred at room temperature for 2 hours. The mixture was concentrated under reduced pressure and the residue azeotroped with toluene. The crude product was purified by column chromatography on silica gel using an elution gradient of ethyl acetate:pentane (30:70 to 50:50) to afford the title compound as a colourless oil, 229 mg; $^1$H NMR (CDCl$_3$, 400 MHz) δ: 0.95 (t, 3H), 1.40 (m, 2H), 1.45–1.75 (m, 10H), 1.95 (m, 3H), 2.05 (m, 3H), 2.50 (m, 1H), 2.65 (m, 2H), 3.25 (s, 3H), 3.35 (m, 2H), 4.00 (t, 2H), 4.05 (t, 2H), 4.45 (m, 1H), 6.80 (m, 3H), 7.20 (d, 2H); Microanalysis found: C, 60.39; H, 7.50; N, 2.49. C$_{27}$H$_{40}$ClNO$_7$; 0.6H$_2$O requires C, 60.40; H, 7.74; N, 2.61%; [α]$_D$=−14.8 (c=0.17, methanol).

Example 50

(3S)-3-[({1-[(2R)-2-(Ethoxycarbonyl)pentyl]cyclopentyl}carbonyl)amino]-4-[(3-methoxybenzyl)oxy]butanoic Acid

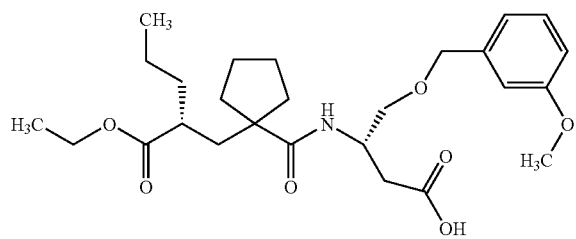

Pyrrolidine (39 μl, 0.46 mmol) and tetrakis(triphenylphosphine)palladium(0) (10 mg) were added to a solution of the allyl ester from preparation 35 (60 mg, 0.116 mmol) in tetrahydrofuran (2 ml), and the reaction stirred at room temperature for 2 hours. The mixture was partitioned between hydrochloric acid (1N) and ethyl acetate, the layers separated, and the organic phase dried (MgSO$_4$) and concentrated under reduced pressure. The residual orange oil was purified by column chromatography on silica gel using an elution gradient of dichloromethane:methanol:acetic acid (99:1:0 to 97:3:0.3) to afford the title compound as a colourless solid, 15 mg; $^1$H NMR (CDCl$_3$, 400 MHz) δ:0.84 (t, 3H), 1.22 (m, 5H), 1.30–1.63 (m, 8H), 1.75 (dd, 1H), 1.84 (m, 1H), 1.96–2.07 (m, 2H), 2.35 (m, 1H), 2.70 (m, 2H), 3.56 (m, 1H), 3.60 (m, 1H), 3.80 (s, 3H), 4.09 (m, 2H), 4.40 (m, 1H), 4.50 (s, 2H), 6.42 (d, 1H), 6.83 (m, 3H), 7.24 (m, 1H); LRMS: m/z (ES$^+$) 500 [MNa$^+$].

Example 51

(3S)-4-[(4-Chlorobenzyl)oxy]-3-[({1-[(2S)-2-(ethoxycarbonyl)-4-methoxybutyl]-cyclopentyl}carbonyl)amino]butanoic Acid

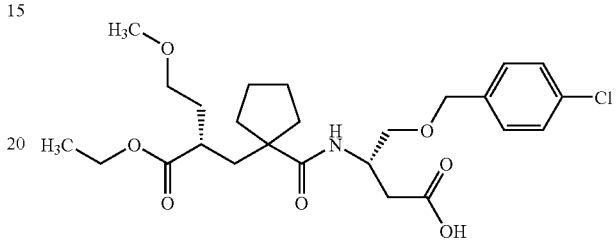

Pyrrolidine (53 mg, 0.74 mmol) and tetrakis(triphenylphosphine)paladium(0) (20 mg) were added to a solution of the allyl ester from preparation 36 (100 mg, 0.186 mmol) in tetrahydrofuran (4 ml), and the reaction stirred at room temperature for 3 hours. The mixture was diluted with hydrochloric acid (1N, 30 ml), the aqueous solution extracted with dichloromethane (3×30 ml), the combined organic solutions washed with water (50 ml), and dried (MgSO$_4$) and concentrated under reduced pressure. The residual yellow oil was purified by column chromatography on silica gel using an elution gradient of dichloromethane:methanol (98:2 to 92:8) to afford the title compound as a colourless oil, 42 mg; $^1$H NMR (CDCl$_3$, 400 MHz) δ: 1.22 (t, 3H), 1.41–1.72 (m, 7H), 1.82 (m, 3H), 1.95–2.05 (m, 2H), 2.46 (m, 1H), 2.64 (m, 2H), 3.28 (m, 4H), 3.38 (m, 1H), 3.46–3.59 (m, 2H), 4.08 (m, 2H), 4.46 (s, 4H), 6.38 (d, 1H), 7.22 (d, 2H), 7.30 (d, 2H); LRMS: m/z (APCI) 498 [MH$^+$].

Example 52

Ethyl (3S)-3-[({1-[(2S)-2-carboxy-4-methoxybutyl]cyclopentyl}carbonyl)amino]-6-(4-chlorophenyl)hexanoate

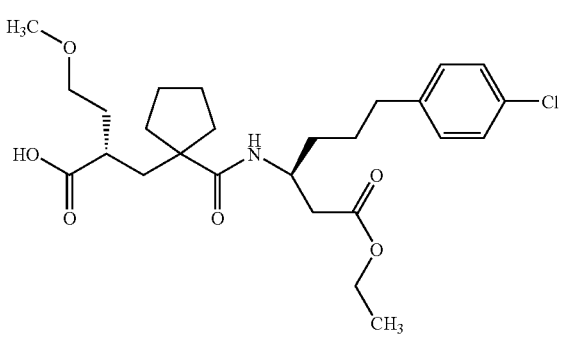

A solution of the diester from preparation 97 (200 mg, 0.36 mmol) in dichloromethane (15 ml) and trifluoroacetic acid (6 ml) was stirred at room temperature for 18 hours. The mixture was concentrated under reduced pressure and the residue partitioned between dichloromethane (75 ml) and water (75 ml). The layers were separated, the organic phase dried (MgSO$_4$) and evaporated under reduced pressure to afford the title compound, as a colourless oil, 180 mg; $^1$H NMR (CDCl$_3$, 400 MHz) δ: 1.22 (t, 3H), 1.44–1.78 (m, 13H), 1.90–2.00 (m, 3H), 2.42–2.62 (m, 5H), 3.22 (s, 3H), 3.37 (m, 2H), 4.15 (q, 2H), 4.26 (m, 1H), 6.80 (d, 1H), 7.08 (d, 2H), 7.22 (d, 2H).

Example 53

(3S)-3-[({1-[(2S)-2-carboxy-4-methoxybutyl]cyclopentyl}carbonyl)amino]-6-(4-chlorophenyl)hexanoic Acid

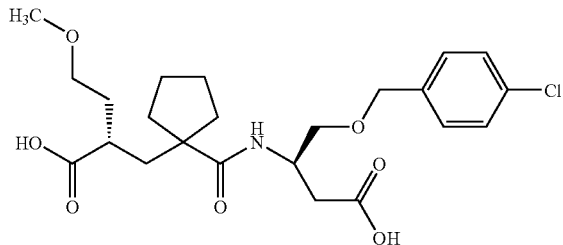

A solution of the ester from example 52 (60 mg, 0.12 mmol) in dioxan (4 ml) and 1N sodium hydroxide (4 ml) was stirred at room temperature for 5 hours. The mixture was concentrated under reduced pressure and the residue partitioned between water (20 ml) and ethyl acetate (20 ml). The layers were separated, the aqueous acidified to pH 1 using hydrochloric acid, and this soluton then re-extracted with ethyl acetate (2×20 ml). These combined organic extracts were dried (MgSO$_4$) and evaporated under reduced pressure to afford the title compound, 49 mg; $^1$H NMR (CDCl$_3$, 400 MHz) δ: 1.42–1.78 (m, 10H), 1.97 (m, 3H), 2.16 (m, 1H), 2.40–2.70 (m, 6H), 3.37 (m, 5H), 3.44 (m, 1H), 4.42 (m, 1H), 6.38 (d, 1H), 7.07 (d, 2H), 7.21 (d, 2H).

Example 54

(3S)-3-[({1-[(2S)-2-carboxy-4-methoxybutyl]cyclopentyl}carbonyl)amino]-6-(4-methoxyphenyl)hexanoic Acid

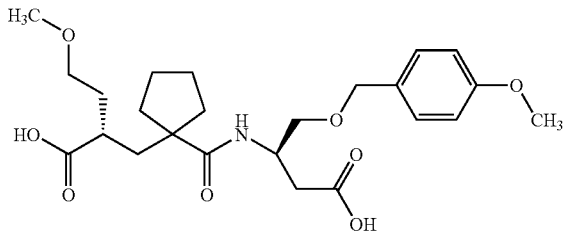

A solution of the ester from preparation 98 (17 mg, 0.03 mmol) in trifluoroacetic acid (0.5 ml) and dichloromethane (2 ml) was stirred at room temperature for 18 hours. The reaction was concentrated under reduced pressure and the residue partitioned between dichloromethane and water, and the layers separated. The organic phase was dried (MgSO$_4$) and evaporated under reduced pressure. The product was purified by Fraction-Lynx® reverse phase HPLC using a Phenomenex Luna C18 column and acetonitrile:water:trifluoroacetic acid (5:95:0.1 to 95.25:4.75:0.005) as eluant to give the title compound; $^1$H NMR (CD$_3$OD, 400 MHz) δ: 1.40–1.86 (m, 12H), 1.97–2.16 (m, 4H), 2.38–2.62 (m, 5H), 3.22 (s, 3H), 3.50 (m, 2H), 3.76 (s, 3H), 4.30 (m, 1H), 6.80 (d, 2H), 7.06 (d, 2H); LRMS: m/z (ES$^-$) 462 [M-H]$^-$.

Preparation 1

1-[(2S)-2-(tert-Butoxycarbonyl)-4-methoxybutyl]cyclopentanecarboxylic Acid

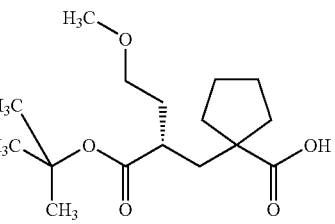

To a solution of 1-[2-(tert-butoxycarbonyl)-4-methoxybutyl]cyclopentane carboxylic acid (WO 0202513) (3.90 kg, 13.0 mol) in heptane (58.5 L, total solution weight 44.0 kg) was added (1S, 2S)-(+)-pseudoephedrine (2.13 kg, 12.9 mol) under an atmosphere of nitrogen at 20° C. The suspension was then heated to 70° C. with stirring until a clear solution was obtained. The solution was then cooled to 40° C. and a sample of authentic crystallised title compound (0.8 g) was added to seed the crystallisation. The temperature of the mixture was maintained at 40° C. for 2 hours and then the slurry was cooled to 20° C. over 6 hours. The product was then collected by filtration and was washed with heptane (2×2.3 L) then dried under vacuum for 22 hours at 50° C. to give (1S, 2S)-1-hydroxy-N-methyl-1-phenyl-2-pr -methoxybutyl]cyclopentane carboxylate (3.20 kg, 6.87 mol, 53% yield as an 86:14 mixture of diastereoisomeric salts as measured by $^1$H NMR). The product (3.20 kg, 6.87 mol) was then suspended in heptane (30 L) and heated to 70° C. until a clear solution was obtained. The resultant solution was then cooled to 58° C. and a sample of authentic crystallised title compound (1.0 g) was added to seed the crystallisation. The solution was then held at 58° C. for 1 hour and was then cooled to 20° C. over 6 hours. The slurry was then granulated at 20° C. for 12 hours. The product was collected by filtration and was washed with heptane (2×(2 L). Drying in a vacuum oven at 50° C. for 22.5 hours gave (1S, 2S)-1-hydroxy-N-methyl- 1-phenyl-2-propanaminium 1-[(2S)-2-(tert-butoxycarbonyl)-4-methoxybutyl]cyclopentane carboxylate as a white crystalline solid (2.35 kg, 5.0 mol, 73% yield). m.p. (heptane); 95° C.; $^1$H-NMR (CDCl$_3$, 300 MHz), □: 1.08 (d, 3H), 1.48 (s, 10H), 1.56–1.74 (m, 4H), 1.74–1.90 (m, 2H), 1.90–2.03 (m, 2H), 2.03–2.27 (m, 2H), 2.4–2.53 (m, 1H), 2.66 (s, 3H), 3.08 (dq, 1H), 3.24 (s, 3H), 3.38 (q, 2H), 4.58 (d, 1H), 7.27–7.45 (m, 5H), 7.70 (s, br, 3H); Anal. found C, 67.06; H, 9.35; N, 3.04; C$_{26}$H$_{43}$NO$_6$ requires C, 67.07; H, 9.31; N, 3.01%. The title compound was obtained by breaking the salt as follows. To a stirred suspension of (1S, 2S)-1-hydroxy-N-methyl-1-phenyl-2-propanaminium 1-[(2S)-2-(tert-butoxycarbonyl)-4-methoxybutyl]cyclopentane carboxylate (210 g, 0.45 mol) in deionised water (1.26 L) and isopropyl acetate (1.47 L) was added aqueous hydrochloric acid (99.5 ml of a 5 M solution, 0.50 mol) until the pH of the aqueous layer was between pH 2 and 3. The layers were then separated, and the aqueous phase was extracted with isopropyl acetate (630 ml). The organic extracts were then combined and washed with saturated brine solution (420 ml). The organic phase was then concentrated by distillation at atmospheric pressure (to remove 1.4 L of isopropyl acetate) to the title compound as a solution in isopropyl acetate which was used directly in the next step. An aliquot can be taken and the solvent removed to give an analytical sample; $^1$H NMR (CDCl$_3$ 300 MHz) δ: 1.44 (s, 9H), 1.48–1.59 (m, 2H), 1.59–1.72 (m, 5H), 1.72–1.93 (m, 2H), 2.03–2.18 (m, 3H), 2.35–2.46 (m, 1H), 3.31 (s, 3H), 3.38 (t, 2H); LRMS (EI): m/z 244 [M-C$_4$H$_8$]$^+$, 227 [M-C$_4$H$_9$O]+, 199 [M-C$_4$H$_9$O$_2$C]$^+$; GC (injector program: initial temp. 0° C., rate 150° C./min, final temp. 230° C.; oven program: initial temp. 100° C., rate 10° C./min, final temp. 230° C., final time 20 min; column, BP-21 25 m×0.25 mm ID×0.25 um FT; detection FID) Retention Time 16.0 min; HPLC (column: ChiralPak AD (25×0.46 cm); mobile phase: hexane/IPA/acetic acid (98/2/0.1 v/v/v); Rinsing mobile phase: hexane/IPA/DEA (80/20/0.5 v/v/v); flow rate: 1.0 ml/min; temperature: ambient; injection volume: 20 μl; detection: ELSD) Run time: 20 mins followed by 10 mins rinse with hexane/IPA/DEA (80/20/0.5 v/v/v), followed by 10 mins rinse with hexane/IPA/acetic acid (98/2/0.1 v/v/v); Retention Time: minor enantiomer 15.5 min (3.3%), major enantiomer 17.5 min (96.7%).

Preparation 2 tert-Butyl (2R)-2-{[1-({[(3S)-5-oxotetrahydro-3-furanyl]amino}carbonyl)-cyclopentyl]methyl}pentanoate

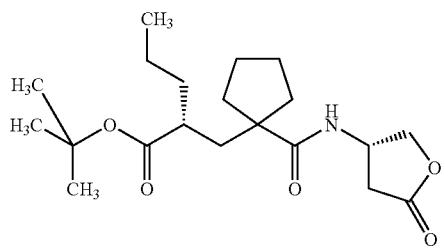

A mixture of 3(S)-amino-γ-butyrolactone hydrobromide (J.A.C.S; 1986; 108(16),
4943) (7 g, 38 mmol), 1-[(2R)-2-(tert-butyoxycarbonyl-pentyl)]-cyclopentanecarboxylic acid (WO 0202513) (11.4 g, 40 mmol), 1-(3-dimethylaminopropyl)-3-ethylcarbodiimide hydrochloride (7.7 g, 40 mmol), 1-hydroxybenzotriazole hydrate (5.4 g, 40 mmol) and 4-methylmorpholine (22 ml, 200 mmol) in dichloromethane (200 ml) was stirred at room temperature for 18 hours. The mixture was washed with water, hydrochloric acid (2N), then dried (MgSO$_4$) and concentrated under reduced pressure. The crude product was purified by column chromatography on silica gel using an elution gradient of dichloromethane:methanol (99:1 to 98:2) to afford the title compound as a colourless oil, 12.6 g; $^1$H NMR (CDCl$_3$, 400 MHz) δ: 0.85 (t, 3H), 1.27 (m, 3H), 1.40–1.68 (m, 17H), 1.88–2.14 (m, 3H), 2.19 (m, 1H), 2.54 (dd, 1H), 2.84 (dd, 1H), 4.19 (dd, 1H), 4.54 (dd, 1H), 4.66 (m, 1H), 6.43 (d, 1H); LRMS: m/z (ES$^+$) 390 [MNa$^+$]; Microanalysis found: C, 62.28; H, 9.26; N, 3.54. C$_{20}$H$_{33}$NO$_5$ requires C, 62.31; H, 9.15; N, 3.63%.

Preparation 3 tert-Butyl (2R)-2-{[1-({[(3R)-5-oxotetrahydro-3-furanyl]amino}carbonyl)cyclopentyl]methyl}pentanoate

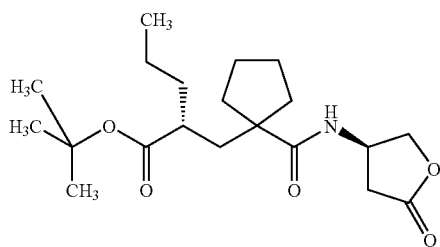

3(R)-Amino-γ-butyrolactone hydrobromide (U.S. Pat. No. 5,252,747, compound 25) (6.2 g, 34 mmol) was added to a solution of 1-[(2R)-2-(tert-butyoxycarbonyl-pentyl)]cyclopentanecarboxylic acid (WO 0202513, preparation 2) (9.9 g, 34.8 mmol), 1-(3-dimethylaminopropyl)-3-ethylcarbodiimide hydrochloride (8.65 g, 44.3 mmol), 1-hydroxybenzotriazole hydrate (6.22 g, 41.8 mmol) and 4-methylmorpholine (14 g, 138 mmol) in dichloromethane (200 ml) and the reaction was stirred at room temperature for 72 hours. The mixture was concentrated under reduced pressure and the residue partitioned between ethyl acetate and brine. The organic phase was dried (MgSO$_4$) and concentrated under reduced pressure. The crude product was purified by column chromatography on silica gel using an elution gradient of dichloromethane:methanol (99:1 to 90:10). The product was triturated with a solution of ether:pentane (20:80) and the resulting precipitate filtered and dried to afford the title compound, 6.3 g.

$^1$H NMR (CDCl$_3$, 400 MHz) δ:0.86 (t, 3H), 1.20–1.39 (m, 3H), 1.40–1.75 (m, 17H), 1.90 (m, 1H), 1.99 (dd, 1H), 2.06 (m, 1H), 2.20 (m, 1H), 2.44 (dd, 1H), 2.84 (dd, 1H), 4.22 (dd, 1H), 4.56 (dd, 1H), 4.66 (m, 1H), 6.22 (d, 1H); LRMS: m/z (ES$^+$) 390 [MNa$^+$]; [α]$_D$=+21.9 (c=0.104, methanol).

Preparation 4 tert-Butyl (2S)-4-methoxy-2-{[1-({[(3S)-5-oxotetrahydro-3-furanyl]amino}carbonyl)-cyclopentyl]methyl}butanoate

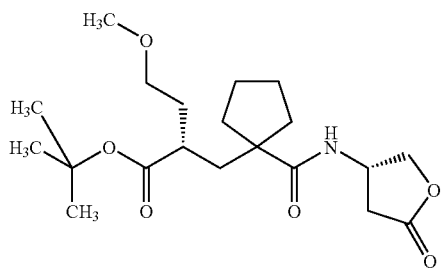

The title compound was obtained as a colourless oil in 82% yield, from the acid from preparation 1 and 3-(S)-amino-γ-butyrolactone hydrobromide (J.A.C.S; 1986; 108 (16), 4943) following a similar procedure to that described in preparation 2; $^1$H-NMR (CDCl$_3$, 400 MHz) δ: 1.41 (m, 11H), 1.50–1.80 (m, 7H), 2.01 (m, 3H), 2.35 (m, 1H), 2.55

(m, 1H), 2.82 (m, 1H), 3.26 (s, 3H), 3.35 (m, 2H), 4.10 (dd, 1H), 4.52 (m, 1H), 4.65 (m, 1H), 6.46 (br d, 1H); LRMS: m/z (APCI) 384 [MH⁺]; Microanalysis found: C, 61.30; H, 8.55; N, 3.60. $C_{20}H_{33}NO_6$; 0.1 $CH_2Cl_2$ requires C, 61.60; H, 8.40; N, 3.57%.

Preparation 5 tert-Butyl (2S)-4-methoxy-2-{[1-({[(3R)-5-oxotetrahydro-3-furanyl]amino}carbonyl)-cyclopentyl]methyl}butanoate

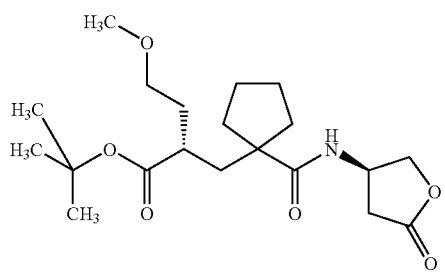

The title compound was obtained as a colourless oil from 3(R)-amino-γ-butyrolactone hydrobromide (U.S. Pat. No. 5,252,747, compound 25) and the acid from preparation 1, following a similar procedure to that described in preparation 4, except the compound was purified by column chromatography on silica gel using an elution gradient of ethyl acetate:pentane (50:50 to 75:25); ¹H-NMR (CDCl₃, 400 MHz) δ: 1.42 (m, 11H), 1.58–1.82 (m, 7H), 1.92–2.08 (m, 3H), 2.35 (m, 1H), 2.46 (m, 1H), 2.82 (dd, 1H), 3.34 (m, 5H), 4.22 (dd, 1H), 4.54 (m, 1H), 4.65 (m, 1H), 6.44 (br d, 1H); LRMS: m/z (ES⁺) 406 [MNa⁺].

Preparation 6

(3S)-3-[({1-[(2R)-2-(tert-Butoxycarbonyl)pentyl]cyclopentyl}carbonyl)amino]-4-hydroxybutanoic Acid

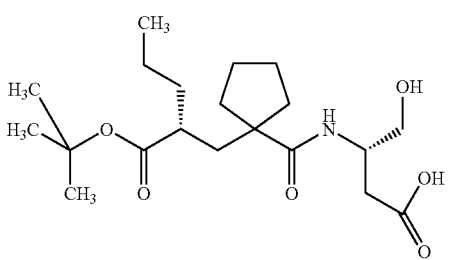

Sodium hydroxide solution (60 ml, 1M, 60 mmol) was added to a solution of the lactone from preparation 2 (12.5 g, 34 mmol) in methanol (200 ml), and the solution stirred at room temperature for 18 hours. The mixture was concentrated under reduced pressure and the residue diluted with water. The aqueous solution was washed with ethyl acetate, acidifed with hydrochloric acid (2N), and this solution extracted with ethyl acetate. The combined organic extracts were dried (MgSO₄), and evaporated under reduced pressure to give a colourless oil. This was triturated with ether, the solid filtered and dried, to afford the title compound as a white solid, 7.55 g; ¹H NMR (CDCl₃, 400 MHz) δ: 0.90 (t, 3H), 1.23–1.40 (m, 3H), 1.42–1.76 (m, 16H), 1.92–2.16 (m, 4H), 2.24 (m, 1H), 2.75 (m, 2H), 3.78 (d, 2H), 4.21 (m, 1H), 6.62 (d, 1H); LRMS: m/z (ES⁺) 386 [MH⁺].

Preparation 7

(3R)-3-[({1-[(2R)-2-(tert-Butoxycarbonyl)pentyl]cyclopentyl}carbonyl)amino]-4-hydroxybutanoic Acid

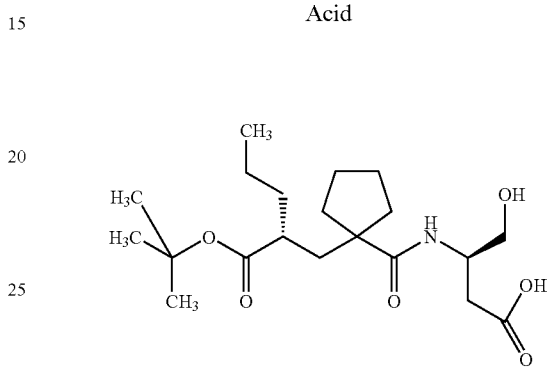

The title compound was obtained from the lactone from preparation 3, following a similar procedure to that described in preparation 6; ¹H NMR (CDCl₃, 400 MHz) δ: 0.86 (t, 3H), 1.20–1.38 (m, 3H), 1.40–1.79 (m, 16H), 1.90 (m, 2H), 2.14 (m, 2H), 2.21 (m, 1H), 2.62 (d, 2H), 3.68 (dd, 1H), 3.79 (dd, 1H), 4.32 (m, 1H), 6.60 (d, 1H).

Preparation 8

(3S)-3-[({1-[(2S)-2-(tert-Butoxycarbonyl)-4-methoxybutyl]cyclopentyl}carbonyl)amino]-4-hydroxybutanoic Acid

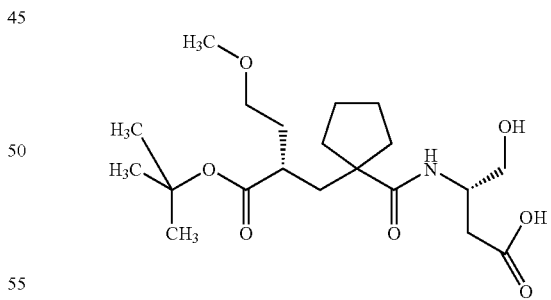

The title compound was obtained from the compound from preparation 4, following a similar procedure to that described in preparation 6; ¹H-NMR (CDCl₃, 400 MHz) δ: 1.44 (m, 11H), 1.58–1.82 (m, 7H), 2.00 (m, 3H), 2.38 (m, 1H), 2.65 (m, 2H), 3.34 (s, 3H), 3.42 (m, 2H), 3.72 (m, 2H), 4.26 (m, 1H), 6.60 (br d, 1H); LRMS: m/z (APCI) 402 [MH⁺].

Microanalysis found: C, 59.71; H, 8.81; N, 3.47. $C_{20}H_{35}NO_7$ requires C, 59.85; H, 8.73; N, 3.49%.

Preparation 9

(3S)-3-[({1-[(2R)-2-(tert-Butoxycarbonyl)-4-methoxybutyl]cyclopentyl}carbonyl)amino]-4-hydroxybutanoic Acid

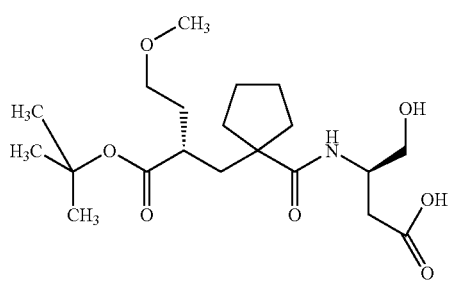

The title compound was obtained as a colourless oil in 64% yield from the lactone from preparation 5, following a similar procedure to that described in preparation 6; $^1$H-NMR (CDCl$_3$, 400 MHz) δ: 1.42 (m, 11H), 1.58–1.82 (m, 7H), 1.92–2.03 (m, 3H), 2.38 (m, 1H), 2.62 (m, 2H), 3.30 (m, 4H), 3.42 (m, 1H), 3.64 (dd, 1H), 3.78 (dd, 1H), 4.38 (m, 1H), 6.54 (d, 1H); LRMS: m/z (ES$^+$) 424 [MNa$^+$].

Preparation 10

(3S)-3-[({1-[(2R)-2-(tert-Butoxycarbonyl)pentyl]cyclopentyl}carbonyl)amino]-4-[(3-methoxybenzyl)oxy]butanoic Acid

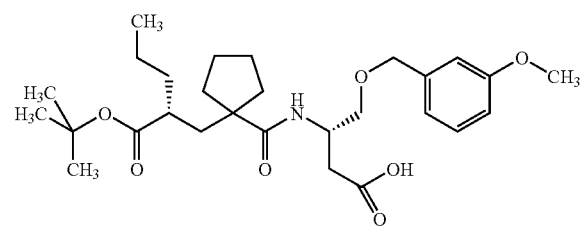

Sodium hydride (60% dispersion in mineral oil, 935 mg, 24 mmol) was added to a cooled (−15° C.) solution of the alcohol from preparation 6 (1 g, 2.6 mmol) in tetrahydrofuran (20 ml), and the mixture stirred for 1 hour. 3-Methoxybenzyl bromide (862 mg, 4.29 mmol) and imidazole (52 mg, 0.79 mmol) were added and the reaction stirred for a further hour a t−15° C., and then allowed to warm to room temperature, and stirred for a further 3 hours. The reaction was quenched by the addition of water, tetrahydrofuran was removed in vacuo and the residue acidified with 1N hydrochloric acid. This aqueous mixture was extracted with ethyl acetate (3×), the combined organic solutions were dried (MgSO$_4$) and evaporated under reduced pressure. The crude product was purified by column chromatography on silica gel using an elution gradient of dichloromethane:methanol (99:1 to 96:4) to afford the title compound as a clear oil; $^1$H NMR (CDCl$_3$, 400 MHz) δ: 0.84 (t, 3H), 1.20–1.37 (m, 3H), 1.44 (m, 12H), 1.56–1.75 (m, 5H), 1.85–2.03 (m, 3H), 2.20 (m, 1H), 2.70 (m, 2H), 3.54 (m, 1H), 3.60 (m, 1H), 3.80 (m, 3H), 4.42 (m, 1H), 4.48 (d, 2H), 6.42 (bd, 1H), 6.64 (m, 3H), 7.23 (m, 1H); LRMS: m/z (ES$^+$) 528 [MNa$^+$].

Preparations 11 to 14

The following preparations of general formula:

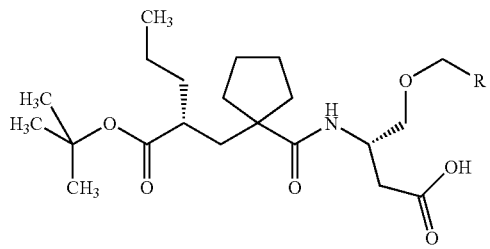

were prepared from the alcohol from preparation 6 and the corresponding benzyl bromides, following a similar procedure to that described in preparation 10.

| Prep. No | R | Data |
|---|---|---|
| 11 | 3-F-C$_6$H$_4$– | $^1$H NMR(CDCl$_3$, 400MHz)δ: 0.81(t, 3H), 1.18–1.70(m, 20H), 1.88(m, 2H), 2.00 (m, 1H), 2.19(m, 1H), 2.65(m, 2H), 3.52(dd, 1H), 3.59(dd, 1H), 4.40(m, 1H), 4.45(s, 2H), 6.40(d, 1H), 6.74–7.04(m, 3H), 7.24(m, 1H). LRMS: m/z(ES$^+$) 494[MH$^+$] |
| 12 | 4-F-C$_6$H$_4$– | $^1$H NMR(CDCl$_3$, 400MHz)δ: 0.84(t, 3H), 1.20–1.77(m, 20H), 1.98(m, 3H), 2.21 (m, 1H), 2.65(m, 2H), 3.58(m, 2H), 4.46(m, 3H), 6.43(d, 1H), 7.02(d, 2H), 7.24(d, 2H). LRMS: m/z(ES$^+$) 494.57[MH$^+$] |
| 13[a] | 4-Cl-C$_6$H$_4$– | $^1$H NMR(CDCl$_3$, 400MHz)δ: 0.82(t, 3H), 1.18–1.70(m, 19H), 1.82–2.02(m, 3H), 2.18(m, 1H), 2.64(d, 2H), 3.55(m, 3H), 4.42(m, 3H), 6.40(d, 1H), 7.24(m, 4H); LRMS: m/z(ES$^+$) 532[MNa$^+$]; [α]$_D$=−17.8(c=0.1, methanol) |
| 14 | 4-CF$_3$-C$_6$H$_4$– | $^1$H NMR(CDCl$_3$, 400MHz)δ: 0.83(t, 3H), 1.18–174(m, 20H), 1.84–2.03(m, 3H), 2.20(m, 1H), 2.70(d, 2H), 3.58(m, 1H), 3.62(m, 1H), 4.44(m, 1H), 4.58(s, 2H), 6.46(d, 1H), 7.41(d, 2H), 7.60(d, 2H). LRMS: m/z(ES$^+$) 566 [MNa$^+$] |

[a]= no imidazole was added to the reaction

Preparation 15

(3R)-3-[({1-[(2R)-2-(tert-Butoxycarbonyl)pentyl]cyclopentyl}carbonyl)amino]-4-[(4-chlorobenzyl)oxy]butanoic Acid

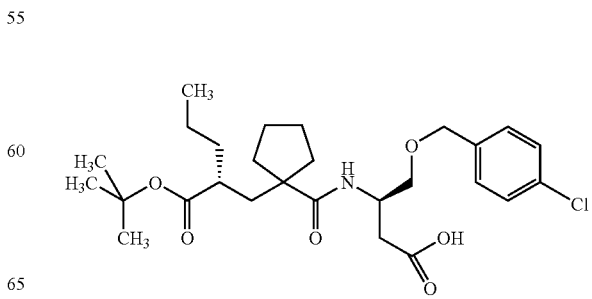

The title compound was obtained in 13% yield from the alcohol from preparation 7 and 4-chlorobenzyl bromide, following a similar procedure to that described in preparation 10; ¹H NMR (CDCl₃, 400 MHz) δ: 0.83 (t, 3H), 1.20–1.38 (m, 3H), 1.40–1.75 (m, 17H), 1.84–2.02 (m, 3H), 2.20 (m, 1H), 2.64 (m, 2H), 3.58 (m, 2H), 4.40–4.56 (m, 3H), 6.45 (d, 1H), 7.23 (d, 2H), 7.30 (d, 2H); LRMS: m/z (ES⁺) 532 [MNa⁺].

Preparation 16

(3R)-3-[({1-[(2R)-2-(tert-Butoxycarbonyl)pentyl]cyclopentyl}carbonyl)amino]-4-[(3-methoxybenzyl)oxy]butanoic Acid

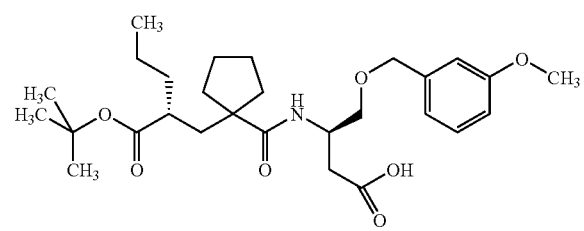

The title compound was obtained in 10% yield from the alcohol from preparation 7 and 3-methoxybenzyl bromide, following a similar procedure to that described in preparation 10; ¹H NMR (CDCl₃, 400 MHz) δ: 0.83 (t, 3H), 1.20–1.36 (m, 3H), 1.40–1.74 (m, 17H), 1.88–2.02 (m, 3H), 2.20 (m, 1H), 2.70 (m, 2H), 3.59 (m, 2H), 3.80 (s, 3H), 4.40 (m, 1H), 4.50 (s, 2H), 6.45 (d, 1H), 6.84 (m, 3H), 7.24 (m, 1H); LRMS: m/z (ES⁺) 528 [MNa⁺].

Preparation 17

(3S)-3-[({1-[(2S)-2-(tert-Butoxycarbonyl)-4-methoxybutyl]cyclopentyl}carbonyl)amino]-4-[(3-methoxybenzyl)oxy]butanoic Acid

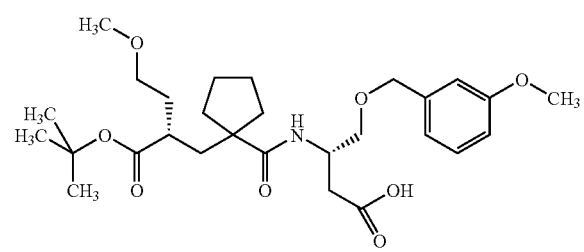

Imidazole (13 mg, 0.19 mmol) and sodium hydride (60% dispersion in mineral oil, 400 mg, 10 mmol) were added to a cooled (−15° C.) solution of the alcohol from preparation 8 (400 mg, 1.0 mmol) in tetrahydrofuran (20 ml), and the mixture stirred for 45 minutes. A solution of 3-methoxybenzyl bromide (221 mg, 1.1 mmol) was added and the reaction stirred for a further 2 hours a t−15° C., and then allowed to warm to room temperature. Stirring was continued for a further 3 hours, then the flask cooled in an ice-bath. The reaction was quenched by the addition of water, diluted with 1N hydrochloric acid, and the mixture extracted with ethyl acetate. The combined organic solutions were dried (MgSO₄) and evaporated under reduced pressure. The crude product was purified by column chromatography on silica gel using an elution gradient of dichloromethane:methanol (98:2 to 92:8) to afford the title compound as a colourless oil, 66 mg; ¹H NMR (CDCl₃, 400 MHz, rotamers) δ: 1.40 (s, 9H), 1.45–2.05 (m, 13H), 2.35 (m, 1H), 2.62 (m, 2H), 3.30 (s, 3H), 3.32–3.60 (m, 3H), 3.78 (s, 3H), 4.45 (s, 2H), 4.47 (m, 1H), 6.20, 6.40 (2×d, 1H), 6.83 (m, 3H), 7.22 (d, 1H); LRMS: m/z (APCI) 522 [MH⁺].

Preparations 18 to 22

The following preparations of general formula:

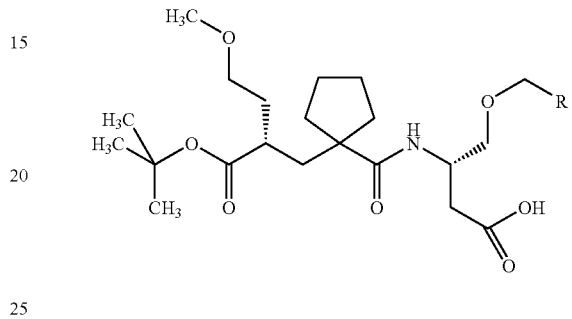

were prepared from the alcohol from preparation 8 and the corresponding benzyl bromides, following a similar procedure to that described in preparation 17.

| Prep. No | R | Data |
|---|---|---|
| 18 | 4-Cl-C₆H₄ | ¹H NMR(CDCl₃, 400MHz, rotamers)δ: 1.37–1.90(m, 20H), 2.00(m, 1H), 2.38(m, 1H), 2.62(m, 2H), 3.32(m, 4H), 3.40–3.59(m, 3H), 4.48(s, 2H), 4.58(m, 1H), 6.02, 6.26(2×d, 1H), 7.22(d, 2H), 7.32(d, 2H); LRMS: m/z(APCI) 526[MH⁺] |
| 19 | 3-Cl-C₆H₄ | ¹H NMR(CDCl₃, 400MHz)δ: 1.41(s, 9H), 1.43–1.80(m, 8H), 1.86(m, 3H), 2.01(m, 1H), 2.38(m, 1H), 2.70(d, 2H), 3.35(m, 4H), 3.40(m, 1H), 3.61(m, 2H), 4.59(m, 3H), 6.36(d, 1H), 7.23(m, 2H), 7.37(m, 1H), 7.40(m, 1H); LRMS: m/z(APCI) 526[MH⁺] |
| 20 | 2-Cl-C₆H₄ | ¹H NMR(CDCl₃, 400MHz)δ: 1.42(s, 9H), 1.43–1.78(m, 8H), 1.83(m, 3H), 2.00(m, 1H), 2.38(m, 1H), 2.64(d, 2H), 3.30(m, 4H), 3.40(m, 1H), 3.54(m, 2H), 4.46(d, 2H), 4.56(m, 1H), 6.24(d, 1H), 7.17(m, 1H), 7.23(m, 3H); LRMS: m/z(APCI) 526[MH⁺] |
| 21 | 3,4-F₂-C₆H₃ | ¹H NMR(CDCl₃, 400MHz)δ: 1.42(s, 9H), 1.45–1.80(m, 9H), 1.85(m, 3H), 2.01(m, 1H), 2.39(m, 1H), 2.65(d, 2H), 3.35(s, 3H), 3.40(m, 1H), 3.57(m, 2H), 4.45(s, 2H), 4.57(m, 1H), 6.28(d, 1H), 7.00(m, 1H), 7.15(m, 2H); LRMS: m/z(ES⁻) 526[M−H]⁻ |
| 22 | 2,4-F₂-C₆H₃ | ¹H NMR(CDCl₃, 400MHz, rotamers)δ: 1.41–1.88(m, 21H), 2.00(m, 1H), 2.38(m, 1H), 2.62(d, 2H), 3.34, 3.40(2×m, 4H), 3.56(m, 2H), 4.56(m, 3H), 6.00, 6.23(2×d, 1H), 6.81(m, 2H), 7.32(m, 1H); LRMS: m/z(ES⁻) 526[M−H]⁻ |

Preparation 23

(3R)-3-[({1-[(2S)-2-(tert-Butoxycarbonyl)-4-methoxybutyl]cyclopentyl}carbonyl)amino]-4-[(4-chlorobenzyl)oxy]butanoic Acid

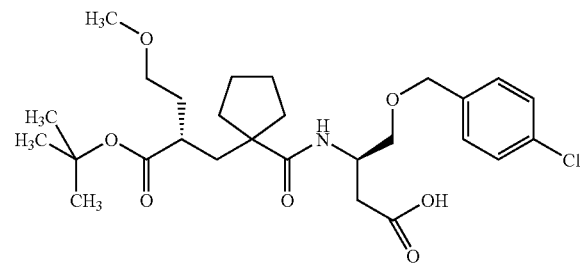

The title compound was obtained as a colourless oil in 30% yield from the alcohol from preparation 9 and 4-chlorobenzyl bromide, following the procedure described in preparation 17; $^1$H NMR (CDCl$_3$, 400 MHz) (rotamers) δ: 1.36 (m, 1H), 1.41–1.88 (m, 18H), 2.01 (m, 1H), 2.18 (m, 1H), 2.40 (m, 1H), 2.62 (m, 2H), 3.34 (m, 4H), 3.50 (m, 3H), 4.47 (s, 2H), 4.59 (m, 1H), 6.00, 6.24 (2×d, 1H), 7.22 (d, 2H), 7.30 (d, 2H); LRMS: m/z (ES$^+$) 548 [MNa$^+$].

Preparation 24 tert-Butyl (2R)-2-[(1-{[((1S)-3-ethoxy-1-{[(3-methoxybenzyl)oxy]methyl}-3-oxopropyl)-amino]carbonyl}cyclopentyl)methyl]pentanoate

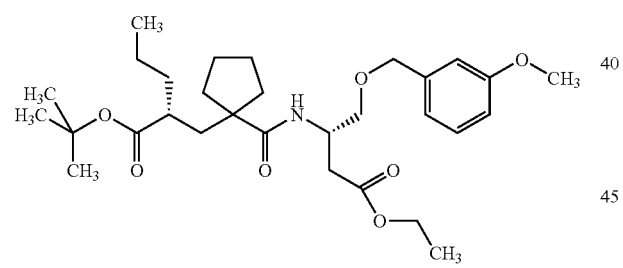

Potassium carbonate (61 mg, 0.45 mmol) and iodoethane (40 μl, 0.49 mmol) were added to a solution of the acid from preparation 10 (275 mg, 0.45 mmol) in N,N-dimethylformamide (5 ml), and the reaction stirred at room temperature for 18 hours. The mixture was diluted with ethyl acetate (20 ml), washed with water (×4) and brine, then dried (MgSO$_4$) and concentrated under reduced pressure. The residue was purified by column chromatography on silica gel using an elution gradient of dichloromethane:methanol (100:0 to 99:1). The residue was azeotroped with xylene, ethyl acetate and dichloromethane to afford the title compound as a colourless oil, 250 mg; $^1$H NMR (CDCl$_3$, 400 MHz) δ: 0.84 (t, 3H), 1.20–1.27 (m, 6H), 1.44 (m, 11H), 1.57–1.76 (m, 6H), 1.97 (m, 3H), 2.21 (m, 1H), 2.63 (m, 2H), 3.48 (m, 1H), 3.59 (m, 1H), 3.80 (s, 3H), 4.10 (q, 2H), 4.44 (m, 3H), 6.56 (br d, 1H), 6.84 (m, 3H), 7.24 (m, 1H);

LRMS: m/z (ES$^+$) 556 [MNa$^+$].

Preparation 25 tert-Butyl (2R)-2-[(1-{[((1S)-1-{[(4-chlorobenzyl)oxy]methyl}-3-ethoxy-3-oxopropyl)amino]-carbonyl}cyclopentyl)methyl]pentanoate

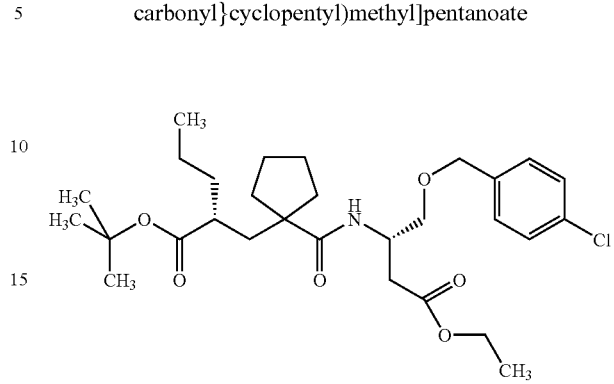

A mixture of the acid from preparation 13 (190 mg, 0.37 mmol), iodoethane (13 mg, 0.84 mmol) and potassium carbonate (158.5 mg, 1.15 mmol) in N,N-dimethylformamide (3 ml) was stirred at room temperature for 72 hours. The mixture was poured into water (100 ml), and extracted with ethyl acetate (3×100 ml). The combined organic extracts were washed with brine (3×100 ml), dried (MgSO$_4$) and evaporated under reduced pressure to afford the title compound as a pale yellow oil, 190 mg; $^1$H NMR (CDCl$_3$, 400 MHz) δ: 0.82 (t, 3H), 1.18–1.78 (m, 23H), 1.98 (m, 3H), 2.20 (m, 1H), 2.61 (m, 2H), 3.50 (dd, 1H), 3.58 (dd, 1H), 4.10 (q, 2H), 4.42 (m, 3H), 6.54 (d, 1H), 7.24 (d, 2H), 7.30 (d, 2H); HRMS: m/z 538.2942 [MH$^+$] C$_{29}$H$_{44}$ClNO$_6$ requires 538.2930; [α]$_D$=−15.8 (c=0.1, methanol).

Preparation 26 tert-Butyl (2R)-2-[(1-{[((1S)-3-(allyloxy)-1-{[(3-methoxybenzyl)oxy]methyl}-3-oxopropyl)amino]carbonyl}cyclopentyl)methyl]pentanoate

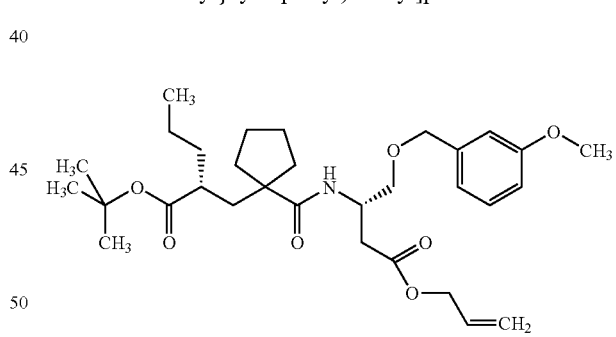

Potassium carbonate (38 mg, 0.27 mmol) and allyl bromide (27 μl, 0.28 mmol) were added to a solution of the acid from preparation 10 (140 mg, 0.28 mmol) in N,N-dimethylformamide (3 ml), and the reaction stirred at room temperature for 18 hours. The mixture was partitioned between ethyl acetate and water, the layers separated, and the organic phase washed with water, dried (MgSO$_4$) and evaporated under reduced pressure to afford the title compound as a colourless oil, 120 mg; $^1$H NMR (CDCl$_3$, 400 MHz) δ:0.83 (t, 3H), 1.20–1.37 (m, 3H), 1.44 (m, 11H), 1.58–1.75 (m, 6H), 1.96 (m, 3H), 2.20 (m, 1H), 2.68 (m, 2H), 3.50 (m, 1H), 3.59 (m, 1H), 3.80 (s, 3H), 4.45 (m, 3H), 4.56 (m, 2H), 5.20–5.34 (m, 2H), 5.87 (m, 1H), 6.52 (m, 1H), 6.83 (m, 3H), 7.24 (m, 1H);

LRMS: m/z (ES$^+$) 568 [MNa$^+$].

Preparation 27 tert-Butyl (2S)-2-[(1-{[(((1S)-1-{[(4-chlorobenzyl)oxy]methyl}-3-ethoxy-3-oxopropyl)amino]-carbonyl}cyclopentyl)methyl]-4-methoxybutanoate

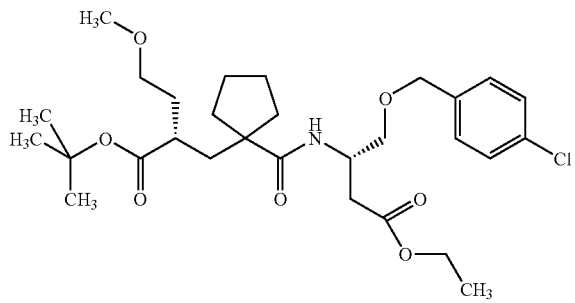

A mixture of the acid from preparation 18 (30 mg, 0.06 mmol), iodoethane (19 mg, 0.12 mmol) and potassium carbonate (24 mg, 0.17 mmol) in N,N-dimethylformamide (2 ml) was stirred at room temperature for 18 hours. TLC showed starting material remaining, so additional iodoethane (19 mg, 0.12 mmol) was added and the reaction stirred at room temperature for a further 3 hours. The reaction was poured into water (30 ml), potassium carbonate (50 mg) added, and this mixture extracted with ethyl acetate (3×20 ml). The combined organic extracts were washed with brine (20 ml), dried (MgSO$_4$) and evaporated under reduced pressure to afford the title compound as a pale yellow oil, 31 mg; $^1$H NMR (CDCl$_3$, 400 MHz) δ: 1.22 (t, 3H), 1.40–1.82 (m, 18H), 1.97 (m, 3H), 2.38 (m, 1H), 2.61 (m, 2H), 3.26 (m, 5H), 3.54 (m, 2H), 4.08 (m, 2H), 4.43 (m, 3H), 6.57 (m, 1H), 7.21 (d, 2H), 7.29 (d, 2H); HRMS: m/z (ESI) 554.2887 [MH$^+$]; C$_{29}$H$_{44}$ClNO$_7$ requires 554.2879 [MH$^+$].

Preparation 28 tert-Butyl (2S)-2-[(1-{[(((1S)-1-{[(3-chlorobenzyl)oxy]methyl}-3-ethoxy-3-oxopropyl)amino]-carbonyl}cyclopentyl)methyl]-4-methoxybutanoate

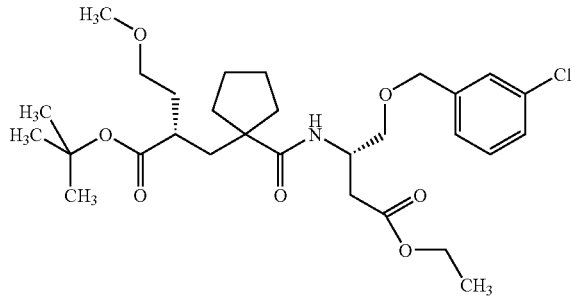

The title compound was obtained as a pale yellow oil, from the acid from preparation 19 and iodoethane, following the procedure described in preparation 27; $^1$H NMR (CDCl$_3$, 400 MHz, rotamers) δ: 1.22 (t, 3H), 1.40–1.80 (m, 18H), 1.97 (m, 3H), 2.38, 2.54 (2×m, 1H), 2.63 (m, 2H), 3.30 (m, 5H), 3.62 (m, 2H), 4.10 (m, 2H), 4.48 (m, 1H), 4.60 (m, 2H), 6.60, 6.70 (2×m, 1H), 7.21 (m, 2H), 7.36 (m, 1H), 7.40 (m, 1H); LRMS: m/z (APCI) 554 [MH$^+$].

Preparation 29 tert-Butyl (2S)-2-[(1-{[(((1S)-1-{[(2-chlorobenzyl)oxy]methyl}-3-ethoxy-3-oxopropyl)amino]-carbonyl}cyclopentyl)methyl]-4-methoxybutanoate

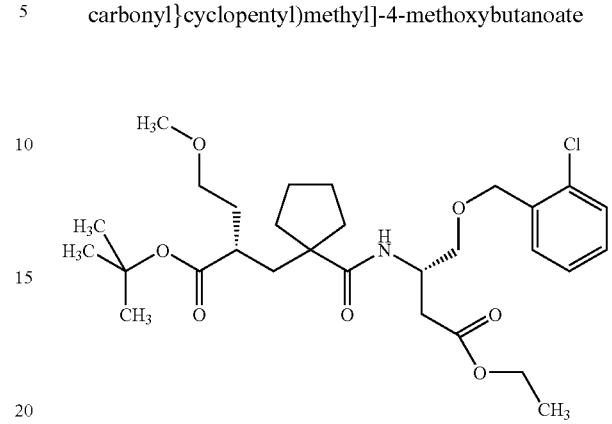

The title compound was obtained as a pale yellow oil, from the acid from preparation 20 and iodoethane, following the procedure described in preparation 27; $^1$H NMR (CDCl$_3$, 400 MHz) δ: 1.22 (t, 3H), 1.40 (m, 10H), 1.60 (m, 5H), 1.78 (m, 3H), 1.98 (m, 3H), 2.37 (m, 1H), 2.63 (m, 2H), 3.30 (m, 5H), 3.58 (m, 2H), 4.10 (q, 2H), 4.44 (m, 3H), 6.58 (d, 1H), 7.17–7.39 (m, 4H); HRMS: m/z (ESI) 554.2888 [MH$^+$] C$_{29}$H$_{44}$ClNO$_7$ requires 554.2879 [MH$^+$].

Preparation 30 tert-Butyl (2S)-2-[(1-{[(((1S)-1-{[(3,4-difluorobenzyl)oxy]methyl}-3-ethoxy-3-oxopropyl)-amino]carbonyl}cyclopentyl)methyl]-4-methoxybutanoate

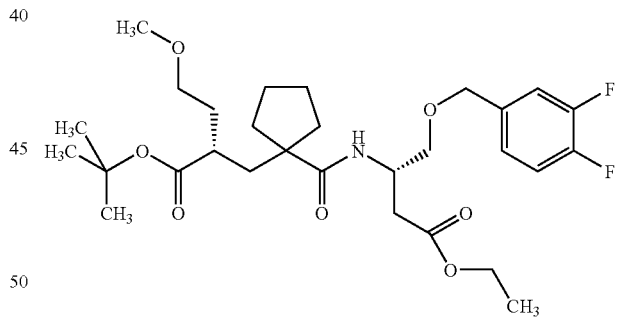

A mixture of the acid from preparation 21 (58 mg, 0.11 mmol), iodoethane (21 mg, 0.13 mmol) and potassium carbonate (36 mg, 0.26 mmol) in N,N-dimethylformamide (2 ml) was stirred at room temperature for 18 hours. The mixture was diluted with water and extracted with ethyl acetate (3×). The combined organic extracts were washed with brine, dried (MgSO$_4$) and evaporated under reduced pressure to afford the title compound, 39 mg; $^1$H NMR (CDCl$_3$, 400 MHz) δ: 1.23 (t, 3H), 1.40–1.82 (m, 18H), 1.98 (m, 3H), 2.37 (m, 1H), 2.63 (m, 2H), 3.24 (s, 3H), 3.32 (m, 2H), 3.50 (m, 1H), 3.58 (m, 1H), 4.10 (q, 2H), 4.42 (m, 3H), 6.58 (d, 1H), 7.00 (m, 1H), 7.13 (m, 2H); LRMS: m/z (APCI) 578 [MNa$^+$].

Preparation 31 tert-Butyl (2S)-2-[(1-{[((1S)-1-{[(2,4-difluorobenzyl)oxy]methyl}-3-ethoxy-3-oxopropyl)-amino]carbonyl}cyclopentyl)methyl]-4-methoxybutanoate

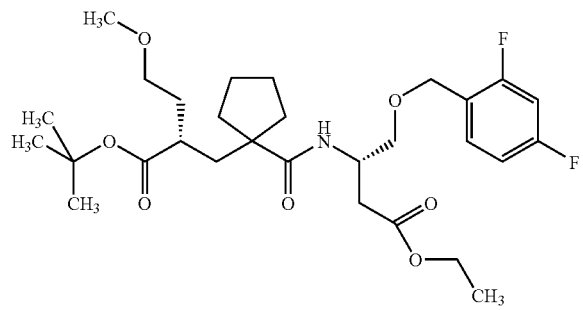

A mixture of the acid from preparation 22 (53 mg, 0.1 mmol), iodoethane (24 mg, 0.15 mmol) and potassium carbonate (28 mg, 0.2 mmol) in N,N-dimethylformamide (2 ml) was stirred at room temperature for 18 hours. The reaction was diluted with water and extracted with dichloromethane. The combined organic solutions were dried (MgSO$_4$) and concentrated under reduced pressure. The residue was purified by column chromatography on silica gel using dichloromethane:methanol (99:1 to 97.5:2.5) to afford the title compound as a colourless oil, 42 mg; $^1$H NMR (CDCl$_3$, 400 MHz) δ: 1.22 (t, 3H), 1.40–1.80 (m, 18H), 1.98 (m, 3H), 2.35 (m, 1H), 2.63 (m, 2H), 3.26 (s, 3H), 3.32 (m, 2H), 3.50 (m, 1H), 3.60 (m, 1H), 4.08 (q, 2H), 4.43 (m, 1H), 4.52 (s, 2H), 6.58 (d, 1H), 6.78–6.88 (m, 2H), 7.36 (m, 1H); LRMS: m/z (ES$^+$) 578 [MNa$^+$].

Preparation 32 tert-Butyl (2S)-2-[(1-{[((1S)-3-(allyloxy)-1-{[(4-chlorobenzyl)oxy]methyl}-3-oxopropyl)-amino]carbonyl}cyclopentyl)methyl]-4-methoxybutanoate

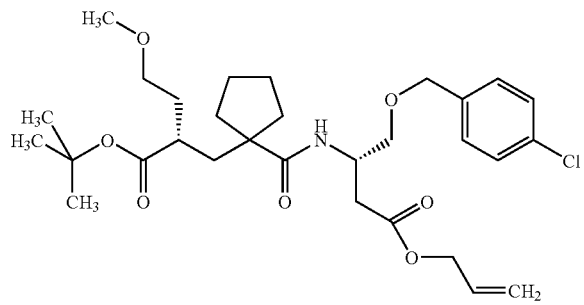

The title compound was obtained as a pale yellow oil in 86% yield, from the acid from preparation 18 and allyl bromide, following the procedure described in preparation 26.

$^1$H NMR (CDCl$_3$, 400 MHz) δ: 1.40–1.82 (m, 18H), 1.98 (m, 3H), 2.38 (m, 1H), 2.68 (m, 2H), 3.27 (m, 5H), 3.50 (m, 1H), 3.58 (m, 1H), 4.44 (s, 3H), 4.57 (d, 2H), 5.22 (d, 1H), 5.30 (d, 1H), 5.85 (m, 1H), 6.58 (d, 1H), 7.22 (d, 2H), 7.30 (d, 2H); LRMS: m/z (APCI) 566 [MH$^+$]; [α]$_D$=−18.8 (c=0.1, methanol); Microanalysis found: C, 63.44; H, 7.91; N, 2.43. C$_{30}$H$_{44}$ClNO$_7$ requires C, 63.70; H, 7.78; N, 2.47%.

Preparation 33

(2R)-2-[(1-{[((1S)-3-(Allyloxy)-1-{[(3-methoxybenzyl)oxy]methyl}-3-oxopropyl)amino]-carbonyl}cyclopentyl)methyl]pentanoic Acid

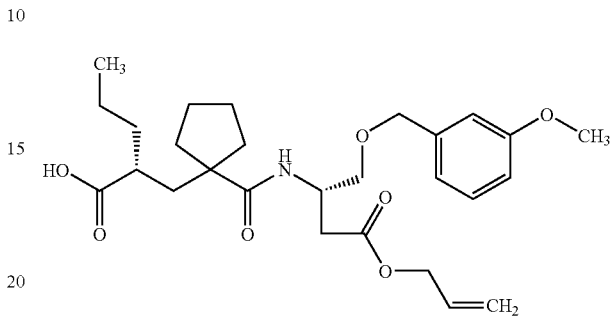

Trifluoroacetic acid (1 ml) was added to a solution of the ester from preparation 26 (120 mg, 0.20 mmol) in dichloromethane (5 ml) and the reaction stirred at room temperature for 3 hours. The mixture was concentrated under reduced pressure and the residue azeotroped with dichloromethane and ethyl acetate to afford the title compound, 110 mg; $^1$H NMR (CDCl$_3$, 400 MHz) δ: 0.85 (t, 3H), 1.50 (m, 4H), 1.50–1.76 (m, 7H), 1.92–2.04 (m, 3H), 2.38 (m, 1H), 2.64 (m, 2H), 3.58 (m, 2H), 3.80 (s, 3H), 4.45 (m, 3H), 4.57 (d, 2H), 5.22 (d, 1H), 5.30 (d, 1H), 5.86 (m, 1H), 6.75 (d, 1H), 6.84 (m, 3H), 7.26 (m, 1H); LRMS: m/z (ES$^+$) 490 [MH$^+$].

Preparation 34

(2S)-2-[(1-{[((1S)-3-(Allyloxy)-1-{[(4-chlorobenzyl)oxy]methyl}-3-oxopropyl)amino]-carbonyl}cyclopentyl)methyl]-4-methoxybutanoic Acid

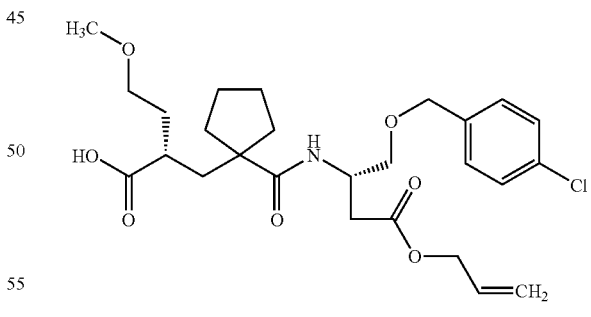

The title compound was obtained as an orange oil, from the ester from preparation 32, following the procedure described in preparation 33; $^1$H NMR (CDCl$_3$, 400 MHz) δ: 1.55–1.74 (m, 8H), 1.97 (m, 3H), 2.10 (m, 1H), 2.56 (m, 1H), 2.62 (m, 2H), 3.26 (s, 3H), 3.38 (m, 2H), 3.57 (m, 2H), 4.43 (m, 3H), 4.56 (m, 2H), 5.21 (d, 1H) 5.27 (d, 1H), 5.84 (m, 1H), 6.64 (d, 1H), 7.21 (m, 2H), 7.30 (d, 2H); LRMS: m/z (ES$^+$) 510 [MH$^+$]; [α]$_D$=−16.670 (c=0.06, methanol); Microanalysis found: C, 59.06; H, 6.96; N, 2.56. C$_{26}$H$_{36}$ClNO$_7$; H$_2$O requires C, 59.20; H, 7.21; N, 2.65%.

Preparation 35

Ethyl (2R)-2-[(1-{[((1S)-3-(allyloxy)-1-{[(3-methoxybenzyl)oxy]methyl}-3-oxopropyl)-amino]carbonyl}cyclopentyl)methyl]pentanoate

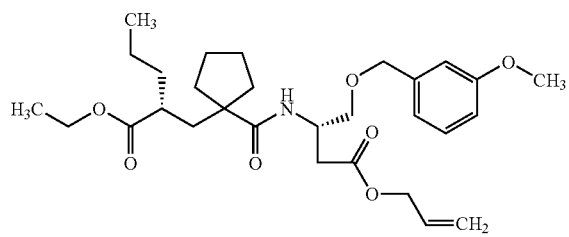

The title compound was obtained as a pale yellow solid, from the acid from preparation 33 and iodoethane, following the procedure described in preparation 26; $^1$H NMR (CDCl$_3$, 400 MHz) δ: 0.82 (t, 3H), 1.21 (m, 6H), 1.30–1.65 (m, 7H), 1.78 (dd, 1H), 1.84–2.04 (m, 3H), 2.35 (m, 1H), 2.66 (m, 2H), 3.50 (m, 1H), 3.59 (m, 1H), 3.79 (s, 3H), 4.08 (m, 2H), 4.44 (m, 3H), 4.56 (d, 2H), 5.21 (d, 1H), 5.32 (d, 1H), 5.87 (m, 1H), 6.50 (d, 1H), 6.82 (m, 3H), 7.22 (m, 1H); LRMS: m/z (ES$^+$) 540 [MNa$^+$].

Preparation 36

Ethyl (2S)-2-[(1-{[((1S)-3-(allyloxy)-1-{[(4-chlorobenzyl)oxy]methyl}-3-oxopropyl)amino]-carbonyl}cyclopentyl)methyl]-4-methoxybutanoate

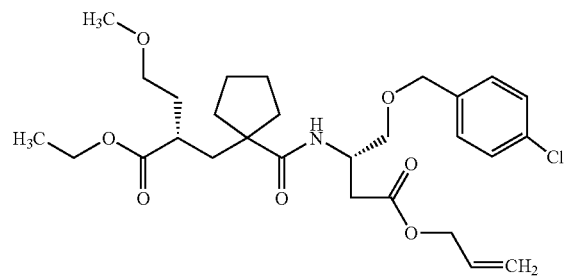

A mixture of the acid from preparation 34 (280 mg, 0.55 mmol), iodoethane (200 mg, 1.29 mmol) and potassium carbonate (228 mg, 1.65 mmol) in N,N-dimethylformamide (3 ml) was stirred at room temperature for 18 hours. The reaction was diluted with water (50 ml) and extracted with ethyl acetate (3×50 ml). The combined organic solutions were washed with brine (2×50 ml), dried (MgSO$_4$) and evaporated under reduced pressure, to afford the title compound as a pale yellow oil, 241 mg; $^1$H NMR (CDCl$_3$, 400 MHz) δ: 1.22 (t, 3H), 1.40–1.70 (m, 7H), 1.78–1.95 (m, 3H), 2.00 (m, 2H), 2.44 (m, 1H), 2.68 (m, 2H), 3.28 (m, 5H), 3.50 (dd, 1H), 3.59 (dd, 1H), 4.10 (m, 2H), 4.44 (s, 3H), 4.56 (d, 2H), 5.22 (d, 1H), 5.30 (d, 1H), 5.88 (m, 1H), 6.57 (d, 1H), 7.22 (d, 2H), 7.31 (d, 2H); Microanalysis found: C, 62.12; H, 7.58; N, 2.68. C$_{28}$H$_{40}$ClNO$_7$ requires C, 62.45; H, 7.43; N, 2.60%.

Preparation 37

Sodium (3R)-3-[(tert-butoxycarbonyl)amino]-4-hydroxybutanoate

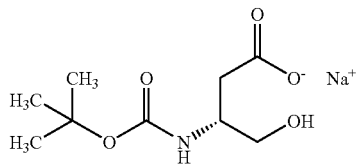

A solution of N$^α$-(tert-butyloxycarbonyl)-D-aspartic anhydride (J. Med. Chem. 1996; 3842) (19 g, 88 mmol) in tetrahydrofuran (150 ml) was added dropwise to an ice-cooled suspension of sodium borohydride (3.4 g, 88 mmol) in tetrahydrofuran (75 ml), and once addition was complete, the mixture was stirred for a further 2 hours. Acetic acid (30 ml) was added dropwise and the mixture then evaporated under reduced pressure. The residue was partitioned between water (150 ml) and ether (150 ml) and 2N hydrochloric acid (20 ml) carefully added. The layers were separated, the aqueous phase further extracted with ether (2×150 ml), and the combined organic solutions dried (MgSO$_4$) and evaporated under reduced pressure. The product was dissolved in 2N sodium hydroxide (50 ml), and the solution stirred for 1 hour. The mixture was washed with ether (2×50 ml), acidified with 2N hydrochloric acid (50 ml) and extracted with dichloromethane (4×100 ml). The combined dichloromethane extracts were dried (MgSO$_4$) and evaporated under reduced pressure. The acid product (7.8 g, 35.6 mmol) was dissolved in methanol (100 ml) sodium hydroxide (1.42 g, 35.6 mmol) added, and the reaction stirred at room temperature for 1 hour. The mixture was evaporated under reduced pressure the residue azeotroped with toluene and then triturated with diisopropyl ether to afford the title compound as a white solid, 8.6 g; $^1$H NMR (DMSOd$_6$, 400 MHz) δ: 1.38 (s, 9H), 2.17 (m, 2H), 3.21–3.50 (m, 3H), 6.74 (d, 1H).

Preparation 38

Ethyl (3S)-4-(benzyloxy)-3-[(tert-butoxycarbonyl)amino]butanoate

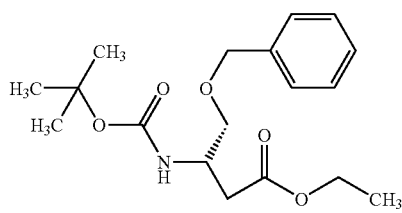

A solution of cesium carbonate (3.53 g, 10.9 mmol) in water (22 ml) was added to an ice-cooled solution of (3S)-4-(benzyloxy)-3-[(tert-butoxycarbonyl)amino]butanoic acid (3.36 g, 10.9 mmol) in methanol (70 ml) and water (7 ml), and the reaction stirred for 20 minutes. The mixture was concentrated under reduced pressure and azeotroped with N,N-dimethylformamide and dichloromethane. The residual oil was dissolved in N,N-dimethylformamide (70 ml), ethyl iodide (1.64 g, 10.9 mmol) added, and the reaction stirred at room temperature for 18 hours. The mixture was concentrated under reduced pressure, suspended in ethyl acetate (300 ml), washed with water (4×), brine, then dried (MgSO₄) and evaporated under reduced pressure. The residual oil was purified by column chromatography on silica gel using hexane:ethyl acetate (85:15) to afford the title compound as a pale yellow oil, 2.86 g; $^1$H NMR (CDCl₃, 400 MHz) δ: 1.26 (t, 3H), 1.45 (s, 9H), 2.65 (d, 2H), 3.58 (m, 2H), 4.17 (m, 3H), 4.55 (s, 2H), 5.20 (bs, 1H), 7.36 (m, 5H).

Preparation 39

(3R)-3-[(tert-Butoxycarbonyl)amino]-4-[(4-cyanobenzyl)oxy]butanoic Acid

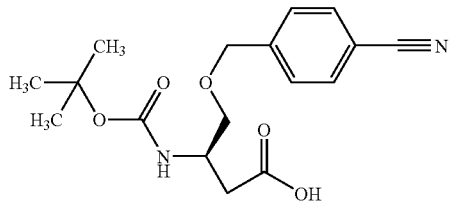

Sodium hydride (650 mg, 60% in mineral oil, 16.25 mmol), followed by imidazole (34 mg, 0.49 mmol) were added portionwise to a cooled (−15° C.) suspension of the acid from preparation 37 (600 mg, 2.49 mmol) in tetrahydrofuran (20 ml), and the mixture then stirred for a further hour. 4-Cyanobenzyl bromide (540 mg, 2.74 mmol) was added, the mixture stirred a t−15° C. for 2 hours and then allowed to warm to room temperature and stirred for a further 18 hours. The reaction mixture was cooled in an ice-bath, water added carefully, followed by 1M hydrochloric acid, and the mixture extracted with ethyl acetate (3×100 ml). The combined organic extracts were washed with brine (150 ml), dried (MgSO₄) and evaporated under reduced pressure. The residual oil was purified by column chromatography on silica gel using dichloromethane:methanol (94:6) as eluant to afford the title compound as a yellow oil, 442 mg; $^1$H NMR (CDCl₃, 400 MHz) δ: 1.42 (s, 9H), 2.68 (d, 2H), 3.59 (m, 2H), 4.18 (m, 1H), 4.59 (s, 2H), 5.17 (m, 1H), 7.41 (d, 2H), 7.62 (d, 2H); HRMS: m/z (ESI⁺) 357.1414 [MNa⁺] $C_{17}H_{22}N_2O_5$ requires C, 357.1421.

Preparation 40

5-(Bromomethyl)-2-methylpyridine Hydrobromide

A solution of (6-methylpyridin-3-yl)methanol (J. Med. Chem. 43; 18; 2000; 3386) (492 mg, 4 mmol) and thionyl bromide (4.16 g, 20 mmol) in dichloromethane (20 ml) was stirred at room temperature for 3 hours. The reaction was concentrated under reduced pressure and the residue azeotroped with dichloromethane. The residual red oil was triturated well with ether to afford the title compound as an orange powder, 1.39 g; $^1$H NMR (DMSOd₆, 400 MHz) δ: 2.64 (s, 3H), 4.81 (s, 2H), 7.81 (d, 1H), 8.42 (d, 1H), 8.84 (s, 1H).

Preparation 41

Ethyl (3R)-3-[(tert-butoxycarbonyl)amino]-4-[(4-cyanobenzyl)oxy]butanoate

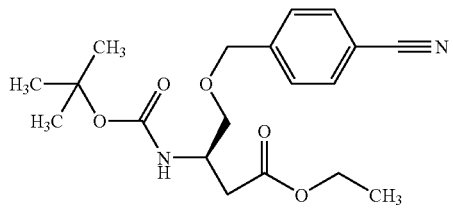

A mixture of the acid from preparation 39 (410 mg, 1.13 mmol), potassium carbonate (468 mg, 3.40 mmol) and iodoethane (529 mg, 3.40 mmol) in N,N-dimethylformamide (5 ml) was stirred at room temperature for 6 hours. The mixture was evaporated under reduced pressure, the residue suspended in brine (100 ml) and extracted with ethyl acetate (3×80 ml). The combined organic extracts were washed with brine (150 ml), dried (MgSO₄) and evaporated under reduced pressure to afford the title compound as a yellow oil, 385 mg; $^1$H NMR (CDCl₃, 400 MHz) δ: 1.22 (t, 3H), 1.42 (s, 9H), 2.62 (d, 2H), 3.58 (m, 2H), 4.05–4.22 (m, 3H), 4.58 (m, 2H), 5.18 (m, 1H), 7.40 (d, 2H), 7.62 (d, 2H).

HRMS: m/z (ESI⁺) 385.1726 [MNa⁺] $C_{19}H_{26}N_2O_5$ requires 385.1726.

Preparation 42

(3R)-3-[(tert-Butoxycarbonyl)amino]-4-[(6-methylpyridin-3-yl)methoxy]butanoic Acid

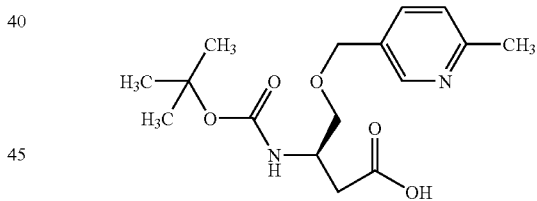

Sodium hydride (800 mg, 60% dispersion in mineral oil, 20 mmol) and imidazole (54 mg, 0.8 mmol) were added portionwise to a cooled (−15° C.) solution of the acid from preparation 37 (960 mg, 4 mmol) in tetrahydrofuran (40 ml) and the solution stirred for 1 hour. A suspension of the bromide from preparation 40 (1.28 g, 4.8 mmol) and N-methyl morpholine (535 mg, 5.3 mmol) in tetrahydrofuran (10 ml) was added so as to maintain the temperature below −15° C., and the reaction then stirred for a further 2 hours. The reaction was allowed to warm to room temperature and stirred for a further 18 hours. The mixture was then basified to pH 11, washed with ethyl acetate, carefully acidifed to pH 5 and extracted with ethyl acetate. These combined organic solutions were washed with brine, dried (MgSO₄) and evaporated under reduced pressure. The crude product was purified by column chromatography on silica gel using dichloromethane:methanol (94:6) as eluant, and the product triturated with ether to afford the title compound, 177 mg; $^1$H NMR (CDCl₃, 400 MHz) δ: 1.42 (s, 9H), 2.62–2.80 (m, 5H), 3.64 (m, 2H), 4.18 (m, 1H), 4.60 (s, 2H), 5.50 (d, 1H), 7.40 (d, 1H), 7.83 (d, 1H), 8.62 (s, 1H); LRMS: m/z (ES⁻) 323 [M-H]⁻.

Preparation 43

Ethyl (3S)-3-amino-4-(benzyloxy)butanoate Hydrochloride

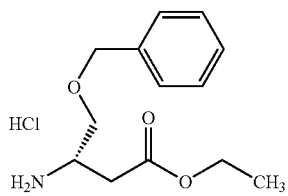

Hydrogen chloride was bubbled through an ice-cooled solution of the protected amine from preparation 38 (2.8 g, 8.3 mmol) in ethyl acetate (40 ml) for 15 minutes. The solution was evaporated under reduced pressure and azeotroped with diethyl ether to afford the title compound as an oil, 2.0 g; ¹H NMR (CDCl₃, 400 MHz) δ: 1.20 (t, 3H), 2.84 (dd, 1H), 3.00 (dd, 1H), 3.58 (m, 2H), 3.90 (m, 1H), 4.10 (q, 2H), 4.58 (s, 2H), 7.30 (m, 5H), 8.60 (bs, 2H).

Preparation 44

Ethyl (3R)-3-amino-4-(4-cyanobenzyloxy)butanoate

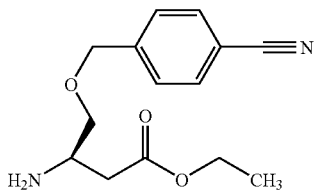

A solution of the protected amine from preparation 41 (375 mg, 1 mmol) and trifluoroacetic acid (2 ml) in dichloromethane (8 ml) was stirred at room temperature for 3 hours. The reaction was concentrated under reduced pressure and the residue azeotroped with dichloromethane. The product was partitioned between ethyl acetate and saturated sodium bicarbonate solution, the layers separated, and the organic phase washed with brine, dried (MgSO₄) and evaporated under reduced pressure to give a yellow oil, 260 mg. The crude product was purified by column chromatography on silica gel using dichloromethane:methanol (97.5:2.5) to afford the title compound as a colourless oil, 180 mg; ¹H NMR (CDCl₃, 400 MHz) δ: 1.22 (t, 3H), 2.65 (d, 2H), 3.57–3.70 (m, 3H), 4.16 (m, 2H), 4.60 (m, 2H), 7.43 (d, 2H), 7.63 (d, 2H); LRMS: m/z (ESI⁺) 285 [MNa⁺].

Preparation 45

Ethyl (3R)-3-amino-4-[(6-methylpyridin-3-yl)methoxy]butanoate Dihydrochloride

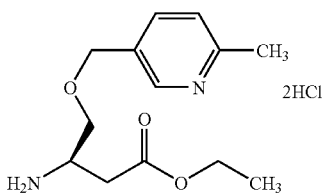

A solution of the protected amine from preparation 42 (175 mg, mmol) in ethanolic hydrogen chloride (6 ml) was heated under reflux for 2 hours. The solution was concentrated under reduced pressure, the residue azeotroped with toluene and dried in vacuo to give the title compound as a colourless gum, 176 mg; ¹H NMR (CD₃OD, 400 MHz) δ: 1.27 (t, 3H), 2.80 (m, 5H), 3.79 (m, 1H), 3.86 (m, 2H), 4.20 (q, 2H), 4.82 (s, 2H), 7.97 (d, 1H), 8.54 (d, 1H), 8.78 (s, 1H); LRMS: m/z (ES⁺) 275 [MNa⁺].

Preparation 46 tert-Butyl (2R)-2-({1-[({(1S)-1-[(benzyloxy)methyl]-3-ethoxy-3-oxopropyl}amino)carbonyl]-cyclopentyl}methyl)pentanoate

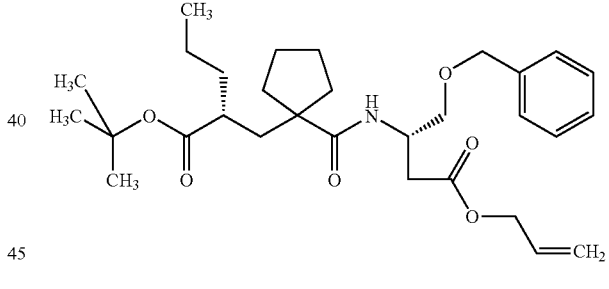

A solution of 1-[(2R)-2-(tert-butyoxycarbonyl-pentyl)] cyclopentanecarboxylic acid (WO 0202513, preparation 2) (156 mg, 0.55 mmol) in dichloromethane (1 ml) was added to a solution of the amine from preparation 43 (150 mg, 0.55 mmol), 1-hydroxybenzotriazole hydrate (74 mg, 0.55 mmol), 1-(3-dimethylaminopropyl)-3-ethylcarbodiimide hydrochloride (105 mg, 0.55 mmol) and N-methyl morpholine (120 μl, 1.1 mmol) in dichloromethane (5 ml), and the reaction stirred at room temperature for 20 hours. The mixture was diluted with dichloromethane (20 ml), washed with 1N hydrochloric acid (10 ml), then water (10 ml), dried (MgSO₄) and evaporated under reduced pressure. The crude product was purified by column chromatography on silica gel using dichloromethane:methanol (100:0 to 95:5) to afford the title compound, 110 mg; ¹H NMR (CDCl₃, 300 MHz) δ: 0.86 (t, 3H), 1.20–1.78 (m, 22H), 1.96–2.30 (m, 5H), 2.63 (m, 2H), 3.56 (dd, 1H), 3.60 (dd, 1H), 4.10 (q, 2H), 4.50 (m, 3H), 6.58 (d, 1H), 7.37 (m, 5H); LRMS: m/z (ES⁺) 526 [MNa⁺].

Preparation 47 tert-Butyl (2R)-2-[(1-{[((1R)-1-{[(4-cyanobenzyl)oxy]methyl}-3-ethoxy-3-oxopropyl)amino]-carbonyl}cyclopentyl)methyl]pentanoate

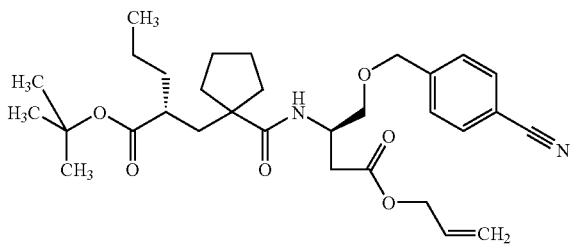

The amine from preparation 44 (160 mg, 0.61 mmol), was added to a solution of 1-[(2R)-2-(tert-butyoxycarbonyl-pentyl)]-cyclopentanecarboxylic acid (WO 0202513, preparation 2) (191 mg, 0.67 mmol), 1-hydroxybenzotriazole hydrate (108 mg, 0.80 mmol), 1-(3-dimethylaminopropyl)-3-ethylcarbodiimide hydrochloride (141 mg, 0.74 mmol) and N-methyl morpholine (169 mg, 1.7 mmol) in dichloromethane (6 ml), and the reaction stirred at room temperature for 18 hours. The reaction was diluted with ethyl acetate, washed with water (2×), then brine, dried (MgSO$_4$) and evaporated under reduced pressure. The residual gum was purified by column chromatography on silica gel using an elution gradient of dichloromethane:methanol (100:0 to 99:1) to afford the title compound as a viscous oil, 240 mg; $^1$H NMR (CDCl$_3$, 400 MHz) δ:0.83 (t, 3H), 1.22 (m, 6H), 1.40–1.77 (m, 17H), 1.97 (m, 3H), 2.20 (m, 1H), 2.62 (m, 2H), 3.60 (m, 2H), 4.10 (q, 2H), 4.50 (m, 1H), 4.60 (s, 2H), 6.59 (d, 1H), 7.41 (d, 2H), 7.62 (d, 2H); LRMS: m/z (ES$^+$) 551 [MNa$^+$].

Preparation 48 tert-Butyl (2R)-2-[(1-{[((1R)-3-ethoxy-1-{[(6-methyl-3-pyridinyl)methoxy]methyl}-3-oxopropyl)amino]carbonyl}cyclopentyl)methyl]pentanoate

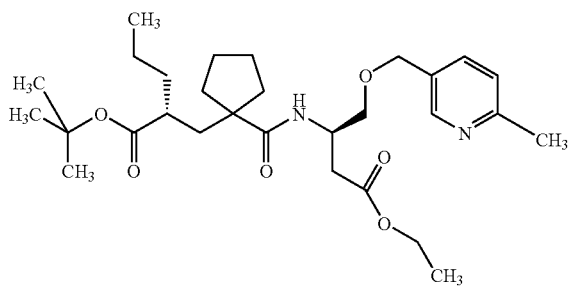

The title compound was obtained as a colourless oil in 67% yield from 1-[(2R)-2-(tert-butyoxycarbonyl-pentyl)]-cyclopentanecarboxylic acid (WO 0202513, preparation 2) and the amine from preparation 45, following the procedure described in preparation 47.

$^1$H NMR (CDCl$_3$, 400 MHz) δ:0.83 (t, 3H), 1.24 (m, 6H), 1.40–1.78 (m, 17H), 1.98 (m, 3H), 2.21 (m, 1H), 2.60 (m, 5H), 3.55 (m, 1H), 3.61 (m, 1H), 4.08 (q, 2H), 4.50 (m, 3H), 6.55 (d, 1H), 7.19 (d, 1H), 7.62 (d, 1H), 8.83 (s, 1H); LRMS: m/z (ES$^+$) 519 [MH$^+$].

Preparation 49

(3S)-4-(Benzyloxy)-3-[({1-[(2R)-2-(tert-butoxycarbonyl)pentyl]cyclopentyl}-carbonyl)amino]butanoic Acid

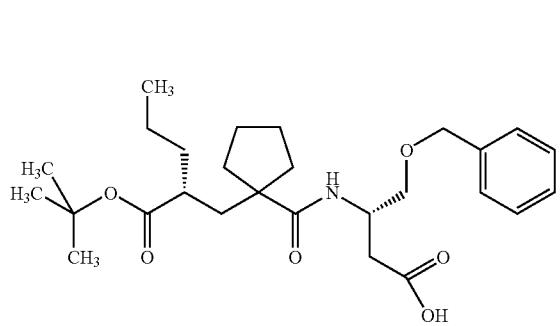

The title compound was prepared, from the alcohol from preparation 6 and benzyl bromide, following the procedure described for preparation 10; $^1$H NMR (CDCl$_3$, 400 MHz) δ: 0.83 (t, 3H), 1.22–1.74 (m, 20H), 1.90–2.02 (m, 3H), 2.21 (m, 1H), 2.67 (m, 2H), 3.56 (dd, 1H), 3.60 (dd, 1H), 4.40–4.58 (m, 3H), 6.48 (d, 1H), 7.17–7.40 (m, 5H);

LRMS: m/z (ES$^-$) 474 [M-H$^-$].

Preparation 50 tert-Butyl (2R)-2-{[1-({[(1S)-1-[(benzyloxy)methyl]-3-(2-butoxyethoxy)-3-oxopropyl]amino}carbonyl)cyclopentyl]methyl}pentanoate

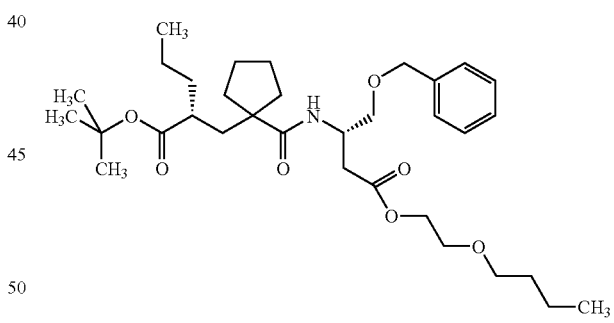

4-Dimethylaminopyridine (30 mg) and 1-(3-dimethylaminopropyl)-3-ethylcarbodiimide hydrochloride (48 mg, 0.25 mmol) were added to a solution of the acid from preparation 49 (120 mg, 0.25 mmol) and 2-butoxyethanol (30 mg, 0.25 mmol) in dichloromethane (5 ml), and the reaction stirred at room temperature for 18 hours. The mixture was evaporated under reduced pressure and the residue purified by column chromatography on silica gel using an elution gradient of dichloromethane:methanol (100:0 to 98:2) to afford the title compound, 100 mg; $^1$H NMR (CDCl$_3$, 400 MHz) δ:0.82 (t, 3H), 0.94 (t, 3H), 1.21–1.76 (m, 24H), 1.98 (m, 3H), 2.20 (m, 1H), 2.68 (m, 2H), 3.41 (d, 2H), 3.52 (m, 1H), 3.60 (m, 3H), 4.19 (m, 2H), 4.44 (m, 3H), 6.50 (d, 1H), 7.30 (m, 5H).

Preparation 51 tert-Butyl (2R)-2-({1-[({(1S)-1-[(benzyloxy)methyl]-3-oxo-3-[2-oxo-2-(1-piperidinyl)ethoxy]propyl}amino)carbonyl]cyclopentyl}methyl)pentanoate

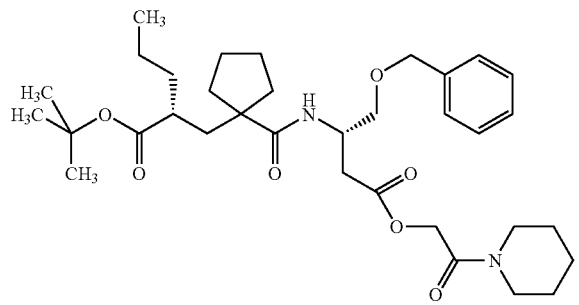

1-(Bromoacetyl)piperidine (EP 580402) (58 mg, 0.28 mmol) was added to a suspension of the acid from preparation 49 (120 mg, 0.25 mmol) and potassium carbonate (35 mg, 0.25 mmol) in N,N-dimethylformamide (3 ml), and the reaction stirred at room temperature for 18 hours. The mixture was concentrated under reduced pressure and the residue purified by column chromatography on silica gel using an elution gradient of dichloromethane:methanol (100:0 to 98.5:1.5) to afford the title compound, 100 mg; $^1$H NMR (CDCl$_3$, 400 MHz) δ: 0.82 (t, 3H), 1.20–1.68 (m, 25H), 1.78 (m, 1H), 2.00 (m, 3H), 2.22 (m, 1H), 2.78 (dd, 2H), 3.25 (m, 2H), 3.56 (m, 2H), 3.60 (m, 2H), 4.58 (m, 3H), 4.62 (d, 1H), 4.78 (d, 1H), 6.98 (d, 1H), 7.26 (m, 5H); LRMS: m/z (ES$^+$) 623 [MNa$^+$].

Preparation 52

(2R)-2-[(1-{[((1R)-1-{[(4-Cyanobenzyl)oxy]methyl}-3-ethoxy-3-oxopropyl)amino]carbonyl}-cyclopentyl)methyl]pentanoic Acid

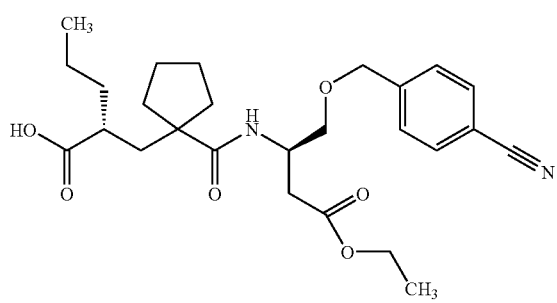

A solution of the ester from preparation 47 (220 mg, 0.42 mmol) and trifluoroacetic acid (2 ml) in dichloromethane (8 ml) was stirred at room temperature for 3 hours. The mixture was concentrated under reduced pressure and the residue azeotroped with dichloromethane. The product was suspended in ethyl acetate, washed with water and brine, then dried (MgSO$_4$) and evaporated under reduced pressure to afford the title compound as a colourless gum, 189 mg; $^1$H NMR (CDCl$_3$, 400 MHz) δ: 0.84 (t, 3H), 1.26 (m, 6H), 1.46–1.78 (m, 8H), 1.98 (m, 1H), 2.02 (m, 2H), 2.38 (m, 1H), 2.62 (m, 2H), 3.60 (m, 2H), 4.10 (q, 2H), 4.44–4.62 (m, 3H), 6.70 (d, 1H), 7.41 (d, 2H), 7.62 (d, 2H); LRMS: m/z (ES$^+$) 495 [MNa$^+$].

Preparation 53

(2R)-2-[(1-{[((1R)-3-Ethoxy-1-{[(6-methyl-3-pyridinyl)methoxy]methyl}-3-oxopropyl)-amino]carbonyl}cyclopentyl)methyl]pentanoic Acid

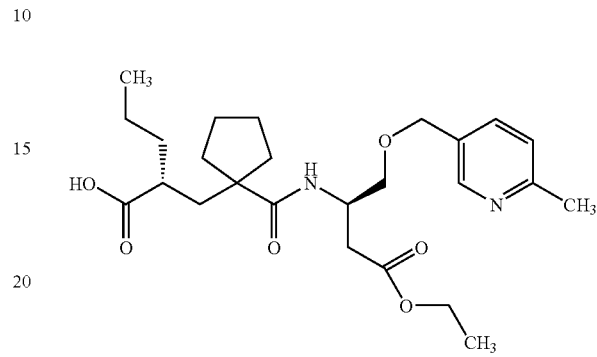

A solution of the ester from preparation 48 (94 mg, 0.18 mmol) and trifluoroacetic acid (1 ml) in dichloromethane (4 ml) was stirred at room temperature for 18 hours. The mixture was concentrated under reduced pressure and the residue azeotroped with dichloromethane. The product was dissolved in water, the pH adjusted to 6 and the mixture extracted with ethyl acetate. The combined organic extracts were dried (MgSO$_4$) and evaporated under reduced pressure. The crude product was purified by column chromatography on silica gel using dichloromethane:methanol (90:10) as eluant to afford the title compound as a colourless gum, 63 mg; HRMS: m/z (ES$^+$) 463.2801 [MH$^+$] C$_{25}$H$_{38}$N$_2$O$_6$ requires 463.2803.

Preparation 54

Ethyl 5-{[tert-butyl(dimethyl)silyl]oxy}-2-pentenoate

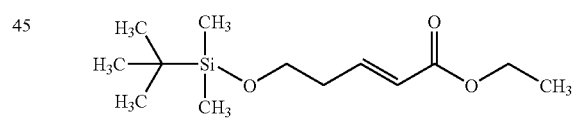

Methyl sulphoxide (1.9 ml, 26.8 mmol) was added to a cooled (−78° C.) solution of oxalyl chloride (2.16 ml, 24.7 mmol) in dichloromethane (100 ml), and after 10 minutes, a solution of 3-(tert-butyl-dimethyl-silanyloxy)-propan-1-ol (3 g, 15.8 mmol) in dichloromethane (25 ml) was added dropwise. Once addition was complete, the solution was stirred for a further 15 minutes. Triethylamine (8 ml, 57.5 mmol) was added, followed by dropwise addition of a solution of (ethoxycarbonylmethylene)triphenylphosphorane (10 g, 29.9 mmol) in dichloromethane (50 ml), and the reaction mixture allowed to warm to room temperature. The mixture was washed with water (4×), dried (MgSO$_4$) and concentrated under reduced pressure. The residue was preadsorbed onto silica gel and purified by column chromatography using diethyl ether:pentane (2.5:97.5) as eluant to afford the title compound, 1.3 g; $^1$H NMR (CDCl$_3$, 400 MHz) δ: 0.02 (s, 6H), 0.87 (s, 9H), 1.26 (t, 3H), 2.40 (m, 2H), 3.74 (t, 2H), 4.18 (q, 2H), 5.84 (d, 1H), 6.95 (m, 1H).

Preparation 55

Ethyl (3R)-3-{(benzyl[(1R)-1-phenylethyl]amino}-5-{[tert-butyl(dimethyl)silyl]oxy}-pentanoate

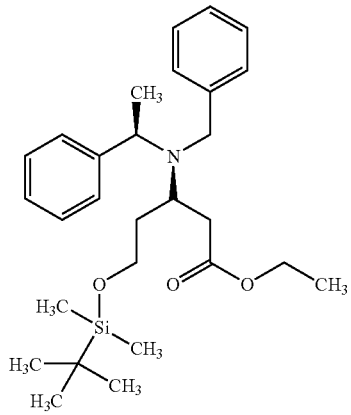

n-Butyl lithium (21.4 ml, 53.5 mmol) was added to a cooled (−78° C.) solution of (R)-(+)—N-benzyl-α-methylbenzylamine (12.0 g, 57.06 mmol) in tetrahydrofuran (100 ml), and the solution stirred for 1 hour. A solution of the compound from preparation 54 (9.2 g, 35.7 mmol) in tetrahydrofuran (50 ml) was added, and the reaction stirred for a further 2 hours a t−78° C. Saturated ammonium chloride solution (40 ml) was added, and the mixture then allowed to warm to room temperature. The mixture was concentrated under reduced pressure, the residue partitioned between ether and water and the layers separated. The organic phase was dried (MgSO$_4$) and evaporated under reduced pressure. The residual yellow oil was purified by column chromatography on silica gel using diethyl ether:pentane (1.5:98.5) as eluant to afford the title compound as a pale yellow oil, 8.6 g; $^1$H NMR (CDCl$_3$, 400 MHz) δ: 0.07 (s, 6H), 0.88 (s, 9H), 1.18 (t, 3H), 1.38 (d, 3H), 1.55 (m, 1H), 1.80 (m, 1H), 2.02 (m, 2H), 3.58 (m, 1H), 3.76 (m, 3H), 3.83 (m, 1H), 3.94–4.06 (m, 2H), 7.20–7.42 (m, 10H); LRMS: m/z (ES$^+$) 470 [MH$^+$].

Preparation 56

Ethyl (3S)-3-{benzyl[(1S)-1-phenylethyl]amino}-5-{[(tert-butyl(dimethyl)silyl]oxy}-pentanoate

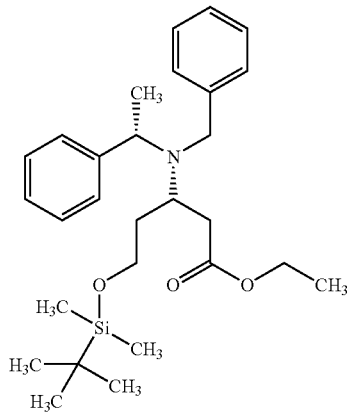

The title compound was obtained as a colourless oil in 56% yield from (S)-(−)—N-benzyl-α-methylbenzylamine and the compound from preparation 54, following the procedure described in preparation 55; $^1$H NMR (CDCl$_3$, 400 MHz) δ: 0.05 (s, 6H), 0.88 (s, 9H), 1.18 (t, 3H), 1.38 (d, 3H), 1.55 (m, 1H), 1.80 (m, 1H), 2.02 (m, 2H), 3.58 (m, 2H), 3.70–3.88 (m, 4H), 3.99 (m, 2H), 7.19–7.37 (m, 8H), 7.40 (d, 2H); [α]$_D$=−4.6 (c=0.096 in methanol).

Preparation 57

Ethyl (3R)-3-amino-5-{[tert-butyl(dimethyl)silyl]oxy}pentanoate

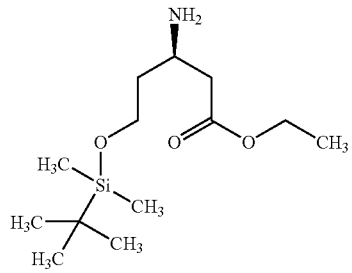

A mixture of the compound from preparation 55 (8.6 g, 18.34 mmol), and 10% palladium on charcoal (2.5 g) in acetic acid (100 ml) was hydrogenated at 6 atm and room temperature for 72 hours. The mixture was filtered through Arbocel® and the filtrate evaporated under reduced pressure. The residue was purified by column chromatography on silica gel using an elution gradient of dichloromethane:methanol:0.88 ammonia (98:2:0.2 to 95:5:0.5) to give an orange oil. The product was dissolved in ethyl acetate, the solution washed with sodium carbonate solution, dried (MgSO$_4$) and evaporated under reduced pressure. The residual oil was further purified by column chromatography on silica gel using an elution gradient of dichloromethane:methanol:0.88 ammonia (99:1:0.1 to 97:3:0.3) to afford the title compound, 3 g; $^1$H NMR (CDCl$_3$, 400 MHz) δ: 0.05 (s, 6H), 0.88 (s, 9H), 1.25 (t, 3H), 1.56–1.68 (m, 2H), 2.34 (dd, 1H), 2.50 (dd, 1H), 3.39 (m, 1H), 3.77 (m, 2H), 4.15 (q, 2H).

Preparation 58

Ethyl (3S)-3-amino-5-{[tert-butyl(dimethyl)silyl]oxy}pentanoate

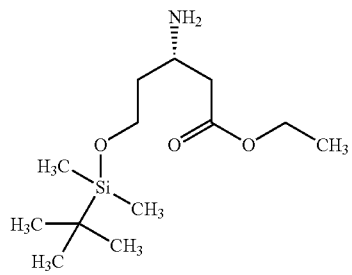

A mixture of the compound from preparation 56 (10.0 g, 21.3 mmol), and 10% palladium on charcoal (2.9 g) in acetic acid (150 ml) was hydrogenated at 6 atm and room temperature for 42 hours. The mixture was filtered through Arbocel®, and the filtrate concentrated under reduced pressure. The residue was partitioned between ethyl acetate and saturated aqueous sodium bicarbonate solution and the layers separated. The aqueous phase was further extracted with ethyl acetate (200 ml), and the combined organic solutions dried (MgSO$_4$) and evaporated under reduced pressure. The crude product was purified by column chromatography on silica gel using an elution gradient of dichloromethane:methanol:0.88 ammonia (95:5:0.5 to 90:10:1) to afford the title compound as a yellow oil, 4.27 g; ¹H NMR (CDCl₃, 400 MHz) δ: 0.05 (s, 6H), 0.88 (s, 9H), 1.25 (t, 3H), 1.64 (m, 2H), 2.40 (dd, 1H), 2.56 (m, 1H), 3.42 (m, 1H), 3.77 (m, 2H), 4.15 (q, 2H); LRMS: m/z (ES⁺) 275.6 [MH⁺].

Preparation 59

Ethyl (3R)-3-[({1-[(2R)-2-(tert-butoxycarbonyl)pentyl]cyclopentyl}carbonyl)amino]-5-{[tert-butyl(dimethyl)silyl]oxy}pentanoate

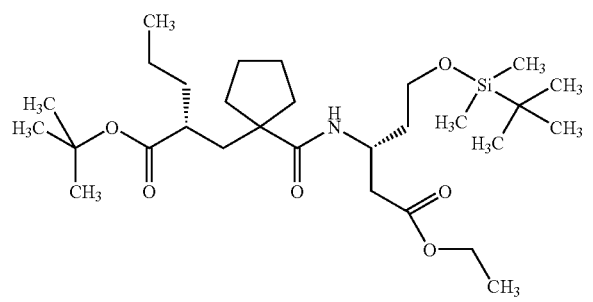

A mixture of the amine from preparation 57 (1.5 g, 5.45 mmol), 1-[(2S)-2-(tert-butyoxycarbonyl-pentyl)]-cyclopentanecarboxylic acid (WO 0202513, preparation 2) (1.7 g, 6.0 mmol), 1-(3-dimethylaminopropyl)-3-ethylcarbodiimide hydrochloride (1.15 g, 6.00 mmol), 1-hydroxybenzotriazole hydrate (811 mg, 6.0 mmol) and N-methylmorpholine (1.15 ml, 10.45 mmol) in dichloromethane (30 ml) was stirred at room temperature for 18 hours. The reaction was washed with water, dried (MgSO₄) and concentrated under reduced pressure. The residual yellow oil was purified by column chromatography on silica gel using dichloromethane:methanol:0.88 ammonia (99.5:0.5:0.05) as eluant to afford the title compound as a colourless oil, 2.3 g; ¹H NMR (CDCl₃, 400 MHz) δ: 0.05 (s, 6H), 0.90 (m, 15H), 1.24–1.55 (m, 15H), 1.58–1.74 (m, 6H), 1.80 (m, 2H), 1.98 (m, 3H), 2.21 (m, 1H), 2.57 (dd, 1H), 2.70 (dd, 1H), 3.70 (m, 1H), 4.16 (q, 2H), 4.37 (m, 1H), 6.65 (d, 1H); LRMS: m/z (ES⁺) 542 [MH⁺].

Preparation 60

Ethyl (3S)-3-[({1-[(2R)-2-(tert-butoxycarbonyl)pentyl]cyclopentyl}carbonyl)amino]-5-{[tert-butyl(dimethyl)silyl]oxy}pentanoate

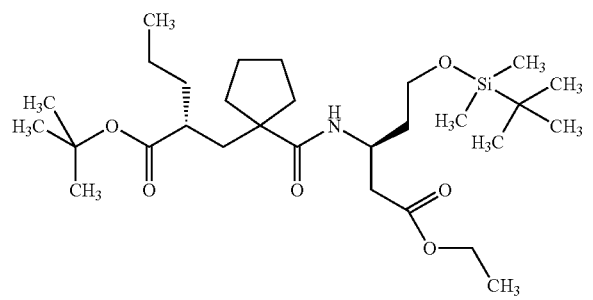

The title compound was obtained as a colourless oil in 56% yield from 1-[(2S)-2-(tert-butyoxycarbonyl-pentyl)]-cyclopentanecarboxylic acid (WO 0202513, preparation 2) and the amine from preparation 58, following a similar procedure to that described in preparation 59, except the compound was purified by column chromatography on silica gel using pentane:ethyl acetate (90:10) and re-columned using an elution gradient of toluene:ethyl acetate (94:4 to 88:12); ¹H NMR (CDCl₃, 400 MHz) δ: 0.05 (s, 6H), 0.86 (m, 12H), 1.26 (t, 3H), 1.43 (m, 13H), 1.59–1.85 (m, 8H), 1.98 (m, 3H), 2.20 (m, 1H), 2.56 (dd, 1H), 2.63 (dd, 1H), 3.70 (m, 1H), 4.14 (q, 2H), 4.37 (m, 1H), 6.60 (d, 1H).
LRMS: m/z (ES⁺) 542 [MH⁺]; [α]_D=−19.88 (c=0.156 in methanol).

Preparation 61 tert-Butyl (3R)-3-[({1-[(2S)-2-(tert-butoxycarbonyl)-4-methoxybutyl]cyclopentyl}carbonyl)-amino]-5-{[tert-butyl(dimethyl)silyl]oxy}pentanoate

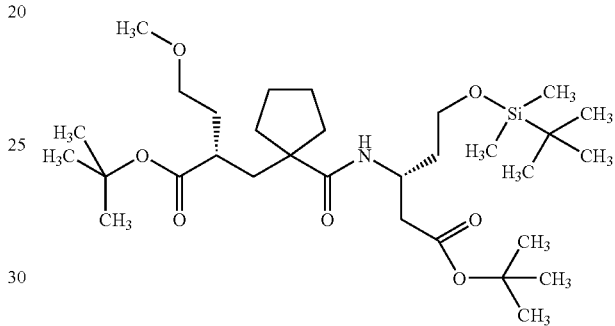

The title compound was obtained as a viscous oil in 84% yield, from (R) tert-butyl-3-amino-5-(tert-butyl-dimethylsilyloxy)-pentanoate (J. Org. Chem. 57(7); 1992; 2120) and the acid from preparation 1, following the procedure described in preparation 59; ¹H NMR (CDCl₃, 400 MHz) δ: 0.03 (s, 6H), 0.90 (s, 9H), 1.42 (2×s, 18H), 1.61 (m, 7H), 1.80 (m, 4H), 1.98 (m, 3H), 2.35 (m, 1H), 2.44 (dd, 1H), 2.60 (dd, 1H), 3.26 (s, 3H), 3.36 (m, 2H), 3.68 (m, 2H), 4.26 (m, 1H), 6.65 (d, 1H); LRMS: m/z (ES⁺) 608 [MNa⁺]; Microanalysis found: C, 63.55; H, 10.15; N, 2.39. C₃₁H₅₉NO₇Si requires C, 63.36; H, 10.05; N, 2.57%.

Preparation 62

Ethyl (3S)-3-[({1-[(2S)-2-(tert-butoxycarbonyl)-4-methoxybutyl]cyclopentyl}carbonyl)-amino]-5-{[tert-butyl(dimethyl)silyl]oxy}pentanoate

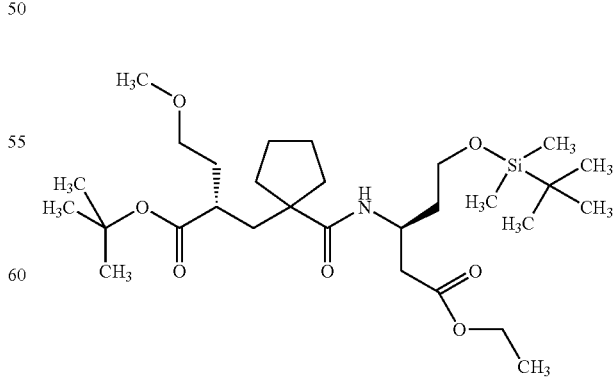

The title compound was obtained as a colourless oil in 87% yield from the acid from preparation 1 and the amine from preparation 58, following a similar procedure to that described in preparation 59, except the compound was purified by column chromatography on silica gel using pentane:ethyl acetate (90:10 to 75:25); ¹H NMR (CDCl₃, 400 MHz) δ: 0.05 (s, 6H), 0.90 (s, 9H), 1.25 (t, 3H), 1.40 (s, 9H), 1.45 (m, 1H), 1.66 (m, 6H), 1.80 (m, 4H), 1.95 (m, 3H), 2.20 (m, 1H), 2.55 (m, 1H), 2.65 (m, 1H), 3.25 (s, 3H), 3.30 (m, 2H), 3.70 (m, 2H), 4.10 (q, 2H), 4.35 (m, 1H), 6.60 (d, 1H);

Preparation 63

Ethyl (3R)-3-[({1-[(2R)-2-(tert-butoxycarbonyl)pentyl]cyclopentyl}carbonyl)amino]-5-hydroxypentanoate

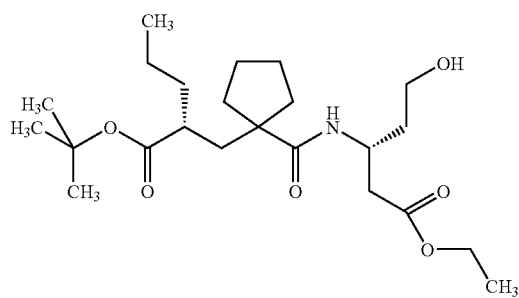

A mixture of the protected alcohol from preparation 59 (1 g, 1.85 mmol), and acetic acid (10 ml) in water (5 ml) and tetrahydrofuran (5 ml) was stirred at room temperature for 2 hours. The reaction was concentrated under reduced pressure, the residue dissolved in ethyl acetate, washed with saturated sodium carbonate solution, dried (MgSO₄) and concentrated under reduced pressure. The residue was purified by column chromatography on silica gel using dichloromethane:methanol:0.88 ammonia (99:1:0.1) to afford the title compound as a colourless oil, 550 mg; LRMS: m/z (ES⁺) 450 [MNa⁺].

Preparation 64

Ethyl (3S)-3-[({1-[(2R)-2-(tert-butoxycarbonyl)pentyl]cyclopentyl}carbonyl)amino]-5-hydroxypentanoate

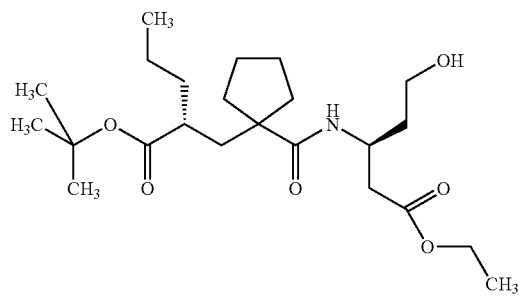

The title compound was obtained in 91% yield from the compound from preparation 60, following a similar procedure to that described in preparation 63; ¹H NMR (CDCl₃, 400 MHz) δ: 0.87 (m, 3H), 1.28 (m, 5H), 1.40–1.84 (m, 19H), 1.98 (m, 3H), 2.22 (m, 1H), 2.59 (m, 2H), 2.98 (m, 1H), 3.60 (m, 2H), 4.18 (m, 2H), 4.40 (m, 1H), 6.94 (d, 1H); LRMS: m/z (ES⁺) 450 [MNa⁺].

Preparation 65 tert-Butyl (3R)-3-[({1-[(2S)-2-(tert-butoxycarbonyl)-4-methoxybutyl]cyclopentyl}carbonyl)amino]-5-hydroxypentanoate

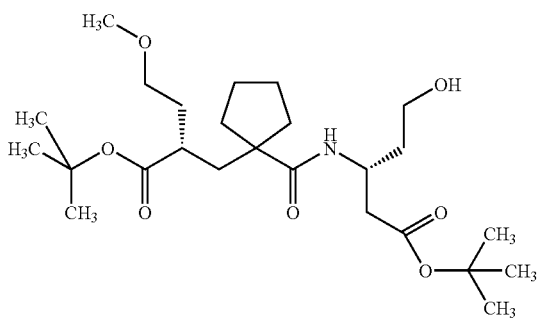

The title compound was obtained as a viscous oil, from the compound from preparation 61, following a similar procedure to that described in preparation 63, but without chromatography; ¹H NMR (CDCl₃, 400 MHz) δ: 1.43 (2×s, 18H), 1.46–1.83 (m, 9H), 1.95–2.08 (m, 3H), 2.38 (m, 1H), 2.44 (dd, 1H), 2.62 (dd, 1H), 2.72 (m, 2H), 3.28 (s, 3H), 3.35 (q, 2H), 3.50 (m, 1H), 3.60 (m, 1H), 4.36 (m, 1H), 7.15 (d, 1H).

Preparation 66

Ethyl-(3S)-3-[({1-[(2S)-2-(tert-butoxycarbonyl)-4-methoxybutyl]cyclopentyl}-carbonyl)amino]-5-hydroxypentanoate

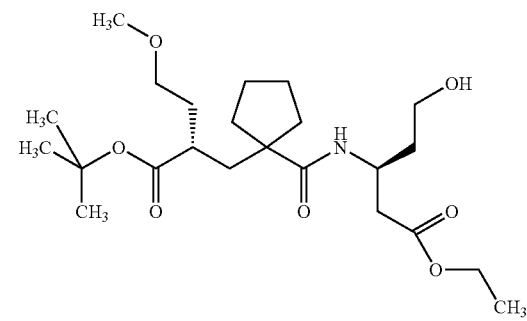

The title compound was obtained as a colourless oil, from the compound from preparation 62, following a similar procedure to that described in preparation 63, but without chromatography; ¹H NMR (CDCl₃, 400 MHz) δ: 1.25 (t, 3H), 1.42 (s, 9H), 1.50–2.01 (m, 14H), 2.38 (m, 1H), 2.56 (dd, 1H), 2.62 (dd, 1H), 3.30 (s, 3H), 3.37 (m, 2H), 3.62 (m, 2H), 4.15 (q, 2H), 4.41 (m, 1H), 6.96 (d, 1H); LRMS: m/z (ES⁺) 466 [MNa⁺].

Preparation 67

Ethyl (3R)-3-[({1-[(2R)-2-(tert-butoxycarbonyl)pentyl]cyclopentyl}carbonyl)amino]-5-phenoxypentanoate

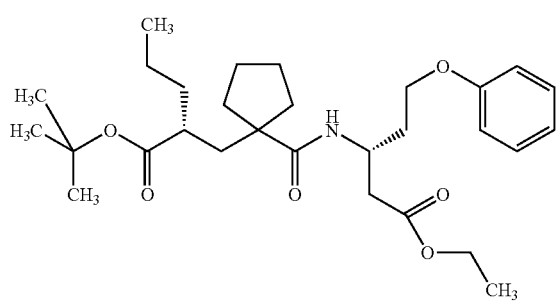

Diisopropyl azodicarboxylate (60 μl. 0.30 mmol) was added to a solution of triphenylphosphine (79 mg, 0.30 mmol), phenyl (28 mg, 0.30 mmol) and the alcohol from preparation 63 (100 mg, 0.23 mmol) in tetrahydrofuran (5 ml), and the mixture stirred at room temperature for 18 hours. The mixture was concentrated under reduced pressure, the residue dissolved in dichloromethane and washed with saturated sodium carbonate solution. The organic solution was then dried (MgSO$_4$) and concentrated under reduced pressure. The residue was purified by column chromatography on silica gel using an elution gradient of ethyl acetate:pentane (87.5:12.5 to 80:20) to afford the title compound as a colourless residue, 60 mg; $^1$H NMR (CDCl$_3$, 400 MHz) δ: 0.84 (t, 3H), 1.24 (m, 6H), 1.40–1.78 (m, 17H), 1.99 (m, 3H), 2.14 (m, 2H), 2.22 (m, 1H), 2.62 (dd, 1H), 2.78 (dd, 1H), 4.02 (m, 2H), 4.19 (q, 2H), 4.44 (m, 1H), 6.78 (d, 1H), 6.90 (d, 2H), 6.98 (m, 1H), 7.25 (m, 2H); LRMS: m/z (ES$^+$) 526 [MNa$^+$].

Preparations 68 to 74

The following compounds of general formula:

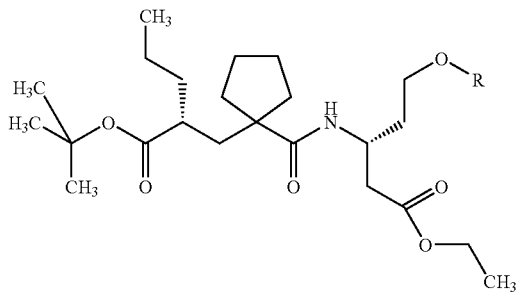

were prepared from the alcohol from preparation 63 and the corresponding alcohols, following a similar procedure to that described in preparation 67.

| Prep. No | R | Data |
|---|---|---|
| 68 | 4-F-C$_6$H$_4$-CH$_2$- | $^1$H NMR(CDCl$_3$, 400MHz)δ: 0.83(t, 3H), 1.25(m, 7H), 1.40–1.77(m, 15H), 1.98(m, 3H), 2.05(m, 3H), 2.21(m, 1H), 2.60(dd, 1H), 2.72(dd, 1H), 3.99(m, 2H), 4.16(q, 2H), 4.43(m, 1H), 6.68(d, 1H), 6.82(m, 2H), 6.97(m 2H); LRMS: m/z (ES$^+$) 544[MNa$^+$] |
| 69 | 4-Cl-C$_6$H$_4$-CH$_2$- | $^1$H NMR(CDCl$_3$, 400MHz)δ: 0.83(t, 3H), 1.25(m, 7H), 1.40–1.75(m, 16H), 1.98(m, 3H), 2.05(m, 2H), 2.20(m, 1H), 2.60(dd, 1H), 2.68(dd, 1H), 4.00(m, 2H), 4.16(q, 2H), 4.43(m, 1H), 6.68(d, 1H), 6.80(d, 2H), 7.20(d, 2H); LRMS: m/z (ES$^+$) 560[MNa$^+$]; Microanalysis found: C 64.49; H, 8.22; N, 2.57. C$_{29}$H$_{44}$ClNO$_6$ requires C, 64.73; H, 8.24; N, 2.60%. |
| 70 | 3-Cl-C$_6$H$_4$-CH$_2$- | $^1$H NMR(CDCl$_3$, 400MHz)δ: 0.83(t, 3H), 1.18–2.10(m, 28H), 2.22(m, 1H), 2.57(dd, 1H), 2.70(dd, 1H), 3.46(m, 1H), 3.60(m, 1H), 4.18(q, 2H), 4.38(m, 1H), 7.03(d, 1H), 7.40–7.74(m, 4H); LRMS: m/z (ES$^+$) 538.4[MH$^+$] |
| 71$^a$ | 4-CH$_3$O-C$_6$H$_4$-CH$_2$- | $^1$H NMR(CDCl$_3$, 400MHz)δ: 0.84(t, 3H), 1.23(m, 7H), 1.40–1.77(m, 16H), 1.98(m, 3H), 2.04(m, 2H), 2.20(m, 1H), 2.58(dd, 1H), 2.72(dd, 1H), 3.77(s, 3H), 4.00(m, 2H), 4.17(q, 2H), 4.42(m, 1H), 6.68(d, 1H), 6.81(s, 4H). |
| 72 | 3-CH$_3$O-C$_6$H$_4$-CH$_2$- | $^1$H NMR(CDCl$_3$, 400MHz)δ: 0.82(t, 3H), 1.20–1.78(m, 23H), 1.98(m, 3H), 2.05(m, 2H), 2.20(m, 1H), 2.60(dd, 1H), 2.74(dd, 1H), 3.79(s, 3H), 4.00(m, 2H), 4.16(q, 2H), 4.42(m, 1H), 6.43(m, 3H), 6.72(d, 1H), 7.18(dd, 1H); LRMS: m/z (APCl$^+$) 534[MH$^+$] |
| 73 | 2-CH$_3$O-C$_6$H$_4$-CH$_2$- | $^1$H NMR(CDCl$_3$, 400MHz)δ: 0.81(t, 3H), 1.22–1.62(m, 22H), 1.75(dd, 1H), 1.90–2.02(m, 3H), 2.10–2.24(m, 3H), 2.59(dd, 1H), 2.77(dd, 1H), 3.84(s, 3H), 4.01–4.18(m, 4H), 4.50(m, 1H), 6.79(d, 1H), 6.84–6.98(m, 4H); LRMS: m/z (ES$^+$) 556[MNa$^+$] |
| 74 | 4-CH$_3$-C$_6$H$_4$-CH$_2$- | LRMS: m/z(ES$^+$) 540[MNa$^+$] |

$^a$= the product was further triturated with pentane to remove impurities

Preparations 75 to 79

The following compounds of general formula:

were prepared from the alcohol from preparation 64 and the corresponding alcohols, following a similar procedure to that described in preparation 67.

| Prep. No | R | Data |
|---|---|---|
| 75 | 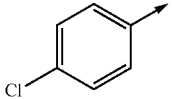 | $^1$H-NMR(CDCl$_3$, 400MHz)δ: 0.81(t, 3H), 1.15–1.34(m, 7H), 1.40–1.78(m, 15H), 1.84–2.20(m, 7H), 2.60(m, 2H), 4.00(m, 2H), 4.16(q, 2H), 4.43(m, 1H), 6.62(d, 1H), 6.80(d, 2H), 7.20(d, 2H); HRMS: m/z(ES$^+$) 538.2924[MH$^+$] |
| 76 | 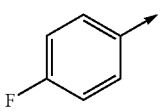 | $^1$H-NMR(CDCl$_3$, 400MHz)δ: 0.81(t, 3H), 1.18–1.38(m, 7H), 1.40–1.78(m, 17H), 1.86–2.14(m, 4H), 2.20(m, 1H), 2.60(m, 2H), 4.00(t, 2H), 4.18(q, 2H), 4.45(m, 1H), 6.60(d, 1H), 6.80(dd, 2H), 7.20(dd, 2H). LRMS: m/z (ES$^+$) 544[MNa$^+$] |
| 77$^a$ | 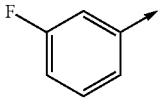 | $^1$H-NMR(CDCl$_3$, 400MHz)δ: 0.80(t, 3H), 1.15–1.30(m, 7H), 1.38–1.78(m, 17H), 1.82–2.20(m, 5H), 2.60(m, 2H), 4.00(t, 2H), 4.16(q, 2H), 4.42(m, 1H), 6.60(m, 4H), 7.18(m, 1H). LRMS: m/z(ES$^+$) 544[MNa$^+$] |
| 78$^a$ | 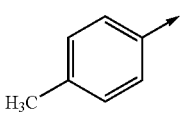 | $^1$H-NMR(CDCl$_3$, 400MHz)δ: 0.82(t, 3H), 1.22(m, 6H), 1.40–1.68(m, 16H), 1.74(dd, 1H), 1.86–2.00(m, 3H), 2.08(m, 2H), 2.19(m, 1H), 2.24(s, 3H), 2.58(dd, 1H), 2.64(dd, 1H), 4.00(t, 2H), 4.16(q, 2H), 4.44(m, 1H), 6.64(d, 1H), 6.78(d, 2H), 7.03(d, 2H). LRMS: m/z(ES$^+$) 540[MNa$^+$] |
| 79$^a$ | 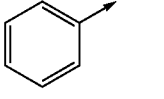 | $^1$H-NMR(CDCl$_3$, 400MHz)δ: 0.82(t, 3H), 1.16–1.36(m, 6H), 1.40–1.68(m, 16H), 1.75(dd, 1H), 1.86–2.21(m, 6H), 2.59(dd, 1H), 2.65(dd, 1H), 4.00(t, 2H), 4.16(q, 2H), 4.46(m, 1H), 6.68(m, 1H), LRMS: m/z(ES$^+$) 526[MNa$^+$] |

$^a$= dichloromethane was used instead of ethyl acetate in the work-up

Preparation 80 tert-Butyl (3R)-3-[({1-[(2S)-2-(tert-butoxycarbonyl)-4-methoxybutyl]cyclopentyl}-carbonyl)amino]-5-(4-chlorophenoxy)pentanoate

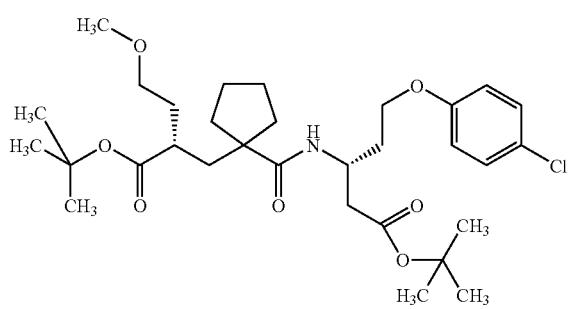

The title compound was obtained as an oil from the alcohol from preparation 65 and p-chlorophenyl, following the procedure described in preparation 67; $^1$H-NMR (CDCl$_3$, 400 MHz) δ: 1.24 (2×s, 18H), 1.55–1.80 (m, 9H), 1.98 (m, 3H), 2.03 (m, 2H), 2.37 (m, 1H), 2.53 (dd, 1H), 2.60 (dd, 1H), 3.26 (m, 5H), 4.00 (m, 2H), 4.39 (m, 1H), 6.70 (d, 1H), 6.80 (d, 2H), 7.20 (d, 2H); LRMS: m/z (ES$^+$) 604 [MNa$^+$].

Preparation 81

Ethyl (3S)-3-[({1-[(2S)-2-(tert-butoxycarbonyl)-4-methoxybutyl]cyclopentyl}carbonyl)amino]-5-(4-chlorophenoxy)pentanoate

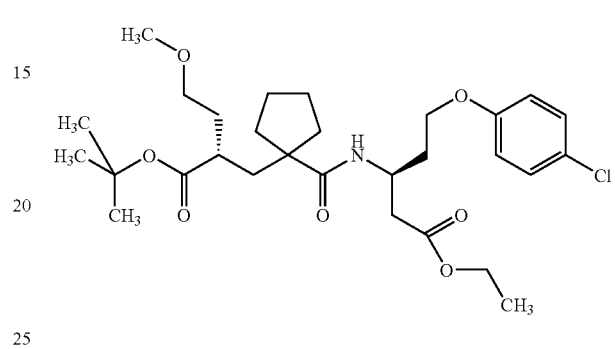

The title compound was obtained as an oil from the alcohol from preparation 66 and p-chlorophenyl, following the procedure described in preparation 67, except the crude product was purified by column chromatography on silica gel using an elution gradient of toluene:methanol (99:1 to 98:2) and re-columned using an elution gradient of ether:pentane (25:75 to 80:20); $^1$H-NMR (CDCl$_3$, 400 MHz) δ: 1.25 (t, 3H), 1.40–1.70 (m, 16H), 1.80 (m, 2H), 1.98 (m, 3H), 2.08 (m, 2H), 2.30 (m, 1H), 2.62 (m, 2H), 3.25 (m, 5H), 4.01 (m, 2H), 4.18 (q, 2H), 4.44 (m, 1H), 6.63 (d, 1H), 6.82 (d, 2H), 7.20 (d, 2H); LRMS: m/z (APCI$^+$) 554 [MH$^+$]; [α]$_D$=−9.67 (c=0.12, methanol).

Preparation 82

(2R)-2-({1-[({(1R)-1-[2-(3-Chlorophenoxy)ethyl]-3-ethoxy-3-oxopropyl}amino)carbonyl]-cyclopentyl}methyl)pentanoic Acid

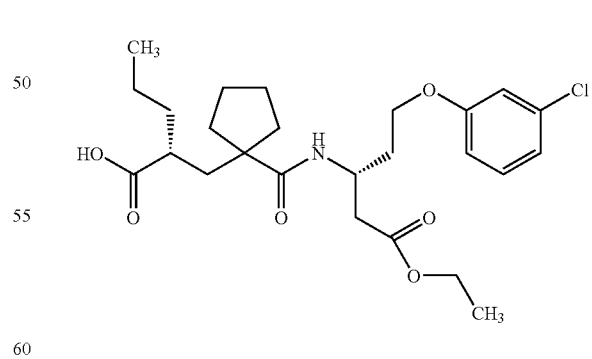

A solution of the ester from preparation 69 (45 mg, 0.08 mmol) and trifluoroacetic acid (0.5 ml) in dichloromethane (2 ml) was stirred at room temperature for 18 hours. The reaction was concentrated under reduced pressure, and the residue azeotroped with toluene to afford the title compound, 40 mg; LRMS: m/z (ES$^+$) 482 [MH]$^+$.

Preparations 83 to 85

The following compounds of general formula:

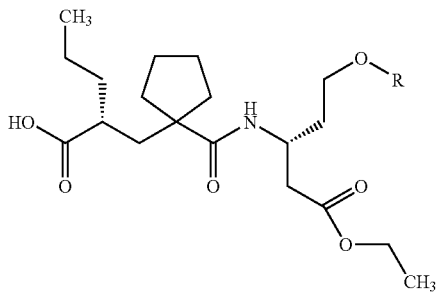

were prepared as colourless oils, from the corresponding tert-butyl esters following a similar procedure to that described in preparation 82.

| Prep. no | R | Data |
|---|---|---|
| 83 | ![3-methoxyphenyl] | LRMS: m/z(ES⁻) 476[M−H]⁻ |
| 84 | ![2-methoxyphenyl] | LRMS: m/z(ES⁺) 476[M−H]⁻ |
| 85[a] | ![4-methylphenyl] | |

[a] = The product was additionally dissolved in ethyl acetate, washed with water, dried ($MgSO_4$) and evaporated under reduced pressure.

Preparation 86

(2R)-2-({1-[({(1S)-1-[2-(4-Chlorophenoxy)ethyl]-3-ethoxy-3-oxopropyl}amino)carbonyl]-cyclopentyl}methyl)pentanoic Acid

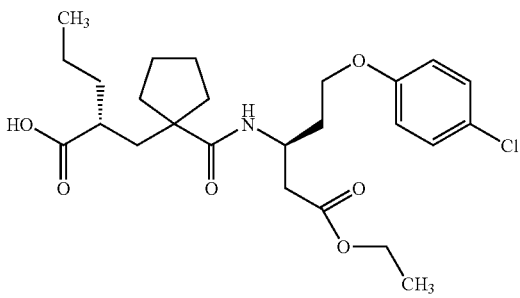

A solution of the ester from preparation 81 (390 mg, 0.72 mmol) in dichloromethane (4 ml) and trifluoroacetic acid (2 ml) was stirred at room temperature for 3 hours. The mixture was concentrated under reduced pressure and the residue purified by column chromatography on silica gel using an elution gradient of dichloromethane:methanol (99:1 to 95:5) to afford the title compound as a colourless oil, 249 mg; $^1$H NMR ($CDCl_3$, 400 MHz) δ: 0.84 (t, 3H), 1.19–1.39 (m, 6H), 1.44–1.80 (m, 7H), 1.93–2.14 (m, 6H), 2.30 (m, 1H), 2.62 (m, 2H), 3.99 (t, 2H), 4.16 (q, 2H), 4.44 (m, 1H), 6.76 (d, 1H), 6.80 (d, 2H), 7.20 (d, 2H); LRMS: m/z (ES⁺) 482 [MH⁺].

Preparations 87 to 90

The following compounds of general formula:

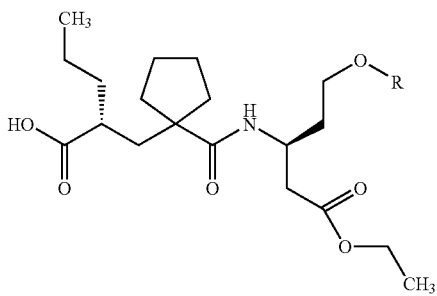

were prepared from the corresponding esters, following the procedure described in preparation 86.

| Prep. no | R | Data |
|---|---|---|
| 87 | ![4-fluorophenyl] | $^1$H NMR($CDCl_3$, 400MHz)δ: 0.82(t, 3H), 1.22–1.39(m, 7H), 1.46–1.70(m, 6H), 1.78(dd, 1H), 1.96–2.12(m, 5H), 2.32(m, 1H), 2.62(m, 2H), 4.00(t, 2H), 4.16(q, 2H), 4.44(m, 1H), 6.76(d, 1H), 6.80(dd, 2H), 6.97(dd, 1H); LRMS: m/z(ES⁺) 488[MNa⁺] |
| 88 | ![3-fluorophenyl] | $^1$H NMR($CDCl_3$, 400MHz)δ: 0.82(t, 3H), 1.20–1.39(m, 7H), 1.43–1.70(m, 6H), 1.78(dd, 1H), 1.96–2.12(m, 5H), 2.30(m, 1H), 2.62(m, 2H), 4.00(t, 2H), 4.16(q, 2H), 4.44(m, 1H), 6.00(m, 3H), 6.74(d, 1H), 7.19(dd, 1H); LRMS: m/z(ES⁺) 488[MNa⁺]; [α$_D$]=−19.27(c=0.136, methanol) |
| 89 | ![4-methylphenyl] | $^1$H NMR($CDCl_3$, 400MHz)δ: 0.84(t, 3H), 1.28(m, 7H), 1.48–1.78(m, 7H), 1.96–2.12(m, 5H), 2.26(s, 3H), 2.36(m, 1H), 2.62(m, 2H), 4.00(t, 2H), 4.16(q, 2H), 4.44(m, 1H), 6.79(m, 3H), 7.04(d, 2H). LRMS: m/z(ES⁻) 460[M−H]⁻ |
| 90[a] | ![phenyl] | $^1$H NMR($CDCl_3$, 400MHz)δ: 0.82(t, 3H), 1.25(m, 6H), 1.43–1.80(m, 8H), 1.96–2.10(m, 5H), 2.37(m, 1H), 2.63(m, 2H), 4.02(t, 2H), 4.16(q, 2H), 4.44(m, 1H), 6.78(d, 1H), 6.85(d, 2H), 6.95(dd, 1H), 7.25(m, 2H); LRMS: m/z(ES⁻) 446[M−H]⁻ |

[a] =the product was additionally purified by reverse phase HPLC using acetonitrile:water:trifluoroacetic acid as gradient eluant.

Preparation 91

(3S)-3-[({1-[(2S)-2-(tert-Butoxycarbonyl)-4-methoxybutyl]cyclopentyl}carbonyl)amino]-5-(4-chlorophenoxy)pentanoic Acid

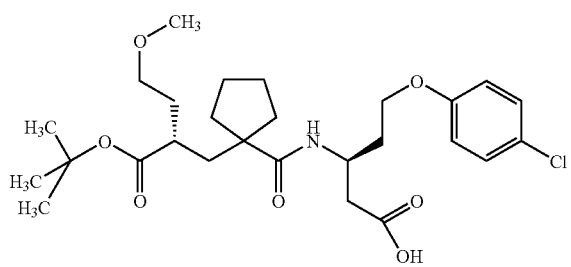

Sodium hydroxide solution (3 ml, 2N) was added to a solution of the ester from preparation 81 (500 mg, 0.90 mmol) in tetrahydrofuran (3 ml) and the reaction stirred under reflux for 5 hours. The cooled mixture was partitioned between ethyl acetate (30 ml) and 2M hydrochloric acid (10 ml), and the layers separated. The aqueous phase was extracted with further ethyl acetate (30 ml), and the combined organic solutions washed with brine (20 ml), dried (MgSO$_4$) and evaporated under reduced pressure. The crude product was purified by column chromatography on silica gel using an elution gradient of dichloromethane:methanol (96:4 to 90:10) to afford the title compound as a colourless oil, 298 mg; $^1$H NMR (CDCl$_3$, 400 MHz) δ: 1.30–1.65 (m, 15H), 1.75 (m, 2H), 1.88 (m, 1H), 2.00–2.16 (m, 5H), 2.40 (m, 1H), 2.58 (dd, 1H), 2.75 (dd, 1H), 3.30 (m, 1H), 3.38 (s, 3H), 3.45 (m, 1H), 4.00 (m, 2H), 4.58 (m, 1H), 6.08 (d, 1H), 6.80 (d, 2H), 7.20 (d, 2H); LRMS: m/z (APCI$^+$) 526 [MH$^+$].

Preparation 92

Butyl (3S)-3-[({1-[(2S)-2-(tert-butoxycarbonyl)-4-methoxybutyl]cyclopentyl}-carbonyl)amino]-5-(4-chlorophenoxy)pentanoate

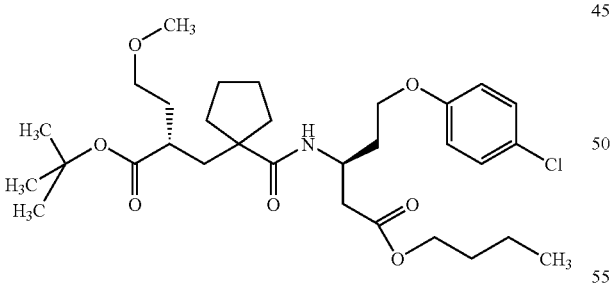

A mixture of the acid from preparation 91 (280 mg, 0.53 mmol), potassium carbonate (74 mg, 0.53 mmol) and n-butyl iodide (67 μl, 0.59 mmol) in N,N-dimethylformamide (2 ml) was stirred at room temperature for 18 hours. The mixture was concentrated under reduced pressure and the residue partitioned between ether (50 ml) and water (25 ml) and the layers separated. The organic phase was washed with 2N sodium hydroxide solution (15 ml), then brine (20 ml), dried (MgSO$_4$) and evaporated under reduced pressure. The residual orange oil was dissolved in a minimum volume of dichloromethane and the solution filtered through silica gel washing through with dichloromethane:methanol solution (25 ml, 97.5:2.5), and the filtrate evaporated under reduced pressure to afford the title compound as a colourless oil, 289 mg; $^1$H NMR (CDCl$_3$, 400 MHz) δ: 0.94 (t, 3H), 1.36–1.58 (m, 19H), 1.61 (m, 4H), 1.79 (m, 1H), 1.96–2.03 (m, 2H), 2.08 (m, 1H), 2.30 (m, 1H), 2.62 (m, 2H), 3.23 (m, 5H), 4.01 (t, 2H), 4.09 (t, 2H), 4.45 (m, 1H), 6.66 (d, 1H), 6.81 (d, 2H), 7.20 (d, 2H); LRMS: m/z (ES$^+$) 604 [MNa$^+$].

Preparation 93 tert-Butyl (3S)-6-(4-chlorophenyl)-3-[(benzyloxycarbonyl)amino]hexanoate

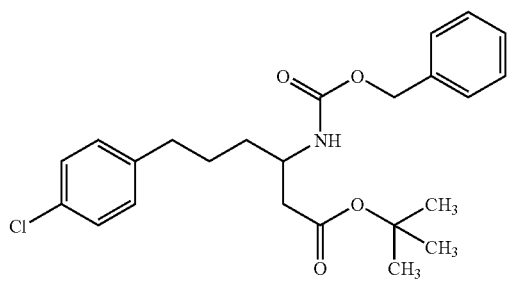

Triethylamine (1.2 ml, 8.9 mmol) followed by diphenylphosphoryl azide (1.6 ml, 7.4 mmol) was added to a solution of 4-tert-butyl hydrogen 2-(4-chlorophenylpropyl)succinate (WO 9504033 intermediate 2f) (2.4 g, 7.4 mmol) in toluene (250 ml), and the solution stirred at room temperature for 30 minutes, then under reflux for a further 3 hours. The mixture was cooled to 50° C., benzyl alcohol (2.3 ml, 22.3 mmol) added, and the reaction heated under reflux for 18 hours. The cooled mixture was concentrated under reduced pressure and the residue dissolved in ethyl acetate (125 ml). This solution was washed with saturated ammonium chloride solution (100 ml), brine (100 ml) and water (100 ml), then dried (MgSO$_4$) and concentrated under reduced pressure. The product was purified by column chromatography on silica gel using ethyl acetate:pentane (6:94) as eluant to afford the title compound as a colourless oil 1.59 g; $^1$H NMR (CDCl$_3$, 400 MHz) δ: 1.41 (s, 9H), 1.46–1.70 (m, 4H), 2.40 (m, 2H), 2.58 (m, 2H), 3.98 (m, 1H), 5.10 (s, 2H), 5.20 (d, 1H), 7.05 (d, 2H), 7.22 (m, 3H), 7.32 (m, 4H); LRMS: m/z (ES$^+$) 454 [MNa$^+$].

Preparation 94

(3S)-3-Amino-6-(4-chlorophenyl)hexanoic Acid Hydrobromide

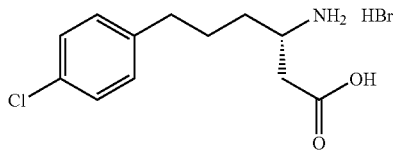

Hydrogen bromide in acetic acid (30 wt. %, 50 ml) was added to a solution of the protected amino acid from preparation 93 (1.5 g, 3.47 mmol) in acetic acid (100 ml), and the reaction stirred at room temperature for 5 hours. The mixture was concentrated under reduced pressure and the residue azeotroped with dichloromethane to afford the title compound as an orange powder, 1.13 g; $^1$H NMR (CD$_3$OD, 400 MHz) δ: 1.68 (m, 4H), 2.55–2.78 (m, 4H), 3.57 (m, 1H), 7.18 (d, 2H), 7.25 (d, 2H); LRMS: m/z (ES$^+$) 242 [MH$^+$].

Preparation 95 tert-Butyl (3S)-3-amino-5-(4-methoxyphenyl)hexanoate

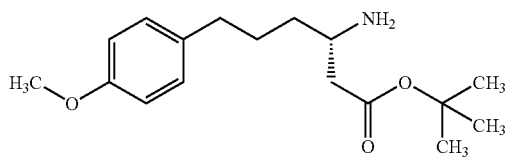

tert-Butyl (3S)-3-{[(benzyloxy)carbonyl]amino}-5-(4-methoxyphenyl)hexanoate was prepared as a colourless oil in 32% yield from 4-tert-butyl hydrogen 2-(4-methoxyphenylpropyl)succinate (WO 9504033 intermediate 4), following the procedure described in preparation 93. A mixture of this compound (110 mg, 0.26 mmol), 10% palladium on charcoal (20 mg) and ethanol (10 ml) was hydrogenated at room temperature for 18 hours. The reaction was filtered, and the filtrate concentrated under reduced pressure. The residue was purified by column chromatography on silica gel twice using dichloromethane:methanol:0.88 ammonia (98:2:0.2) to afford the title compound; $^1$H NMR (CDCl$_3$, 400 MHz) δ: 1.42 (s, 9H), 1.60–1.80 (m, 4H), 2.20 (dd, 1H), 2.39 (dd, 1H), 2.58 (t, 2H), 3.18 (m, 1H), 3.79 (s, 3H), 6.82 (d, 2H), 7.07 (d, 2H); LRMS: m/z (ES$^+$) 294 [MH$^+$].

Preparation 96

Ethyl (3S)-3-amino-6-(4-chlorophenyl)hexanoate Hydrochloride

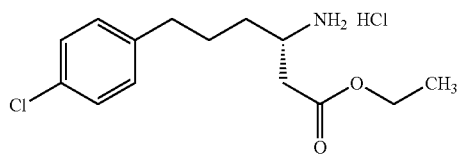

Ethanolic hydrogen chloride (45 ml) was added to a solution of the acid from preparation 94 (1.06 g, 3.29 mmol) in ethanol (45 ml), and the reaction stirred at room temperature for 6 hours. The mixture was evaporated under reduced pressure to afford the title compound as an orange oil, 1.1 g; $^1$H NMR (CD$_3$OD, 400 MHz) δ: 1.24 (t, 3H), 1.68 (m, 4H), 2.58–2.80 (m, 4H), 3.58 (m, 1H), 4.19 (q, 2H), 7.20 (d, 2H), 7.25 (d, 2H).

Preparation 97

Ethyl (3S)-3-[({1-[(2S)-2-(tert-butoxycarbonyl)-4-methoxybutyl]cyclopentyl}carbonyl)amino]-6-(4-chlorophenyl)hexanoate

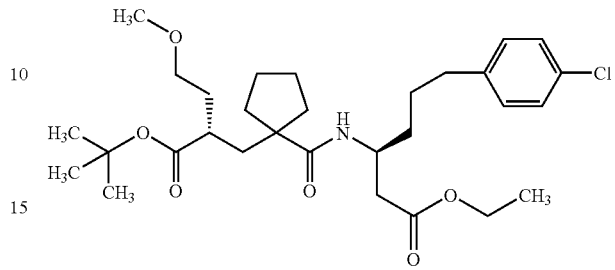

1-Hydroxybenzotriazole hydrate (486 mg, 3.60 mmol), 1-(3-dimethylaminopropyl)$_3$-ethylcarbodiimide hydrochloride (690 mg, 3.60 mmol) and N-methyl morpholine (1.32 g, 13.08 mmol) were added to a solution of the amine from preparation 96 (1.0 g, 3.27 mmol), and the acid from preparation 1 (980 mg, 3.27 mmol) in dichloromethane (50 ml), and the reaction stirred at room temperature for 18 hours. The reaction was diluted with dichloromethane (100 ml), washed with brine (100 ml), dried (MgSO$_4$) and evaporated under reduced pressure. The residual gum was purified by column chromatography on silica gel using pentane:ethyl acetate (85:15) to give the title compound, 1.31 g; $^1$H NMR (CDCl$_3$, 400 MHz) δ: 1.24 (t, 3H), 1.44–1.70 (m, 21H), 1.79 (m, 2H), 1.98 (m, 3H), 2.36 (m, 2H), 2.60 (m, 2H), 3.24 (m, 5H), 4.12 (q, 2H), 4.26 (m, 1H), 6.42 (d, 1H), 7.10 (d, 2H), 7.21 (d, 2H).

Preparation 98 tert-butyl (3S)-3-[({1-[(2S)-2-(tert-butoxycarbonyl)-4-methoxybutyl]cyclopentyl}carbonyl)amino]-6-(4-methoxyphenyl)hexanoate

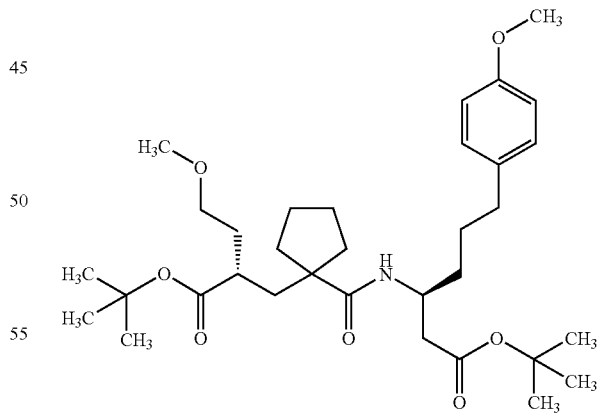

The title compound was obtained in 67% yield from the amine from preparation 95 and the acid from preparation 1, following the procedure described in preparation 97; $^1$H NMR (CDCl$_3$, 400 MHz) δ: 1.42 (2×s, 18H), 1.44–1.70 (m, 12H), 1.80 (m, 2H), 1.98 (m, 2H), 2.37 (m, 1H), 2.40 (m, 2H), 2.58 (m, 2H), 3.22 (s, 3H), 3.27 (m, 2H), 3.78 (s, 3H), 4.23 (m, 1H), 6.44 (d, 1H), 6.80 (d, 2H), 7.08 (d, 2H); LRMS: m/z (ES$^+$) 598 [MNa$^+$].

Preparation 99 tert-Butyl (2R)-2-[(1-{[((1R)-1-{[(4-chlorobenzyl)oxy]methyl}-3-ethoxy-3-oxopropyl)-amino]carbonyl}cyclopentyl)methyl]pentanoate

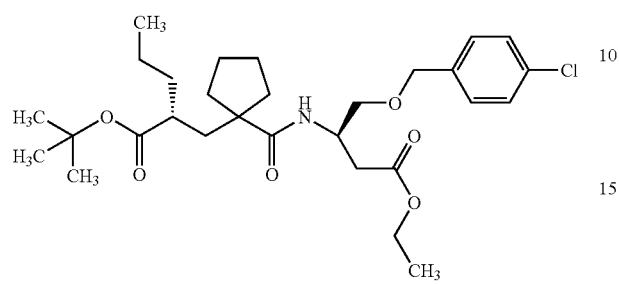

The title compound was prepared as a colourless oil in 77% yield, from the acid from preparation 15 and ethyl iodide, following the procedure described in preparation 24.

$^1$H NMR (CDCl$_3$, 400 MHz) δ: 0.83 (t, 3H), 1.19–1.78 (m, 23H), 2.98 (m, 3H), 2.21 (m, 1H), 2.61 (m, 2H), 3.58 (m, 2H), 4.06 (t, 2H), 4.45 (s, 3H), 6.50 (m, 1H), 7.25 (m, 4H).

LRMS: m/z (ES$^+$) 560 [MNa$^+$].

Biological Assays

IC$_{50}$ values of the compounds of the invention against NEP and ACE were determined using methods described in published patent application EP1097719-A1, paragraphs [0368] to [0376]. The IC$_{50}$ values presented below were determined using NEP (EC.3.4.24.11) from human kidney.

The compounds of the invention are potent inhibitors of NEP and are selective against ACE.

The title compounds of all diacid examples showed an IC$_{50}$% against NEP of less than 250 nM.

The title compounds of Examples 1–5, 7, 10–16, 31–42, 44, 46, 48, 53 and 54 showed an IC$_{50}$ against NEP of less than or equal to 50 nM and a selectivity over ACE of greater than 300 fold.

In particular, the title compound of Example 16 showed an IC$_{50}$ against NEP of 8.2 nM; the title compound of Example 41 showed an IC$_{50}$ against NEP of 6.3 nM; the title compound of Example 48 showed an IC$_{50}$ against NEP of 2.4 nM; the title compound of Example 53 showed an IC$_{50}$ against NEP of 0.7 nM; and the title compound of Example 54 showed an IC$_{50}$ against NEP of 4.7 nM. The title compounds of all these Examples were greater than 300 fold selective against ACE.

What is claimed is:

1. A compound of formula (I), a pharmaceutically acceptable salt or solvate thereof

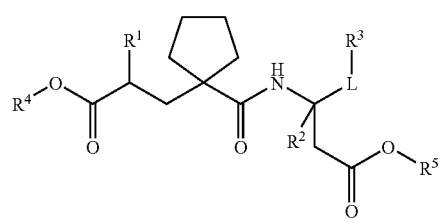

(I)

wherein
R$^1$ is C$_1$–C$_6$alkyl, C$_1$–C$_6$alkoxyC$_1$–C$_3$alkyl or C$_1$–C$_6$alkoxyC$_1$–C$_6$alkoxyC$_1$–C$_3$alkyl;

R$^2$ is hydrogen or C$_1$–C$_6$alkyl;

L is a three atom linkage selected from —CH$_2$—X—CH$_2$— and —CH$_2$—CH$_2$—X— where the right hand side of the linkage is attached to R$^3$ and where X is oxygen or methylene;

R$^3$ is phenyl which may be independently substituted by one or more groups selected from: C$_1$–C$_6$alkyl, halo, haloC$_1$–C$_6$alkyl, C$_1$–C$_6$alkoxy, haloC$_1$–C$_6$alkoxy, C$_1$–C$_6$alkylthio, haloC$_1$–C$_6$alkylthio and nitrile; and R$^4$ and R$^5$ are either both hydrogen or one of R$^4$ and R$^5$ is hydrogen and the other is a biolabile ester-forming group selected from:

i) C$_1$–C$_6$alkyl optionally substituted by hydroxy, oxo, halo, haloC$_1$–C$_6$alkyl, C$_1$–C$_6$alkoxy, haloC$_1$–C$_6$alkoxy, C$_1$–C$_6$alkylthio haloC$_1$–C$_6$alkylthio, nitrile, carbocyclyl, carbocyclyloxy, alkylcarbonyloxy, carbocyclylcarbonyloxy, alkylcarbonylamino, or alkylaminocarbonyl, wherein any carbocyclyl group is optionally substituted by C$_1$–C$_6$alkyl, halo, haloC$_1$–C$_6$alkyl, C$_1$–C$_6$alkoxy, haloC$_1$–C$_6$alkoxy, C$_1$–C$_6$alkylthio, haloC$_1$–C$_6$alkylthio or nitrile; or ii) carbocyclyl optionally substituted by C$_1$–C$_6$alkyl, halo, haloC$_1$–C$_6$alkyl, C$_1$–C$_6$alkoxy, haloC$_1$–C$_6$alkoxy, C$_1$–C$_6$alkylthio, haloC$_1$–C$_6$alkylthio or nitrile.

2. The compound according to claim 1 wherein R$^1$ is C$_1$–C$_6$alkyl or C$_1$–C$_6$alkoxyC$_1$–C$_3$alkyl.

3. The compound according to claim 2 wherein R$^1$ is propyl or methoxyethyl.

4. The compound according to claim 1 wherein R$^2$ is hydrogen.

5. The compound according to claim 3 wherein R$^2$ is hydrogen.

6. The compound according to claim 5 wherein L is —CH$_2$—CH$_2$—O— or CH$_2$—CH$_2$—CH$_2$—.

7. The compound according to claim 1 wherein R$^3$ is 4-fluorophenyl, 4-chlorophenyl, 4-methoxyphenyl or 4-methylphenyl.

8. The compound to claim 6 wherein R$^3$ is 4-fluorophenyl, 4-chlorophenyl, 4-methoxyphenyl or 4-methylphenyl.

9. The compound according to claim 1 wherein any carbocyclic group is phenyl.

10. The compound according to claim 1 wherein the biolabile ester-forming group is: ethyl, propyl, butyl isobutyl, cyclopentyl, benzyl, 1-(2,2-diethylbutyryloxy)ethyl, 2-ethylpropionyloxymethyl, 1-(2-ethylpropionyloxy)ethyl, 1-(2,4-dimethylbenzoyloxy)ethyl, 1-benzoyloxy)benzyl, 1-(benzoyloxy)ethyl, 2-methyl-1-propionyloxypropyl, 2,4,6-trimethylbenzoyloxymethyl, 1-(2,4,6-trimethylbenzyloxy)ethyl, pivaloyloxymethyl, phenethyl, phenpropyl, 2,2,2-trifluoroethyl, 1-naphthyl, 2-naphthyl, 2,4-dimethylphenyl, 4-t-butylphenyl, 5-(4-methyl-1,3-dioxalynyl-2-onyl)methyl, N,N-diethylaminocarbonylmethyl or 5-indanyl.

11. The compound according to claim 1 wherein R$^4$ and R$^5$ are both hydrogen.

12. The compound according to claim 8 wherein R$^4$ and R$^5$ are both hydrogen.

13. The compound according to claim 1 wherein the compound is of formula (Ia)

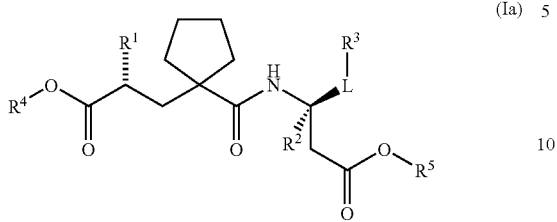

(Ia)

and $R^1$, $R^2$, $R^3$, $R^4$, $R^5$, and L are as defined in claim 1.

14. The compound according to claim 13 wherein $R^1$ is $C_1$–$C_6$alkyl or $C_1$–$C_6$alkoxy$C_1$–$C_3$alkyl.

15. The compound according to claim 14 wherein $R^1$ is propyl or methoxyethyl.

16. The compound to claim 13 wherein $R^2$ is hydrogen.

17. The compound according to claim 15 wherein $R^2$ is hydrogen.

18. The compound according to claim 17 wherein L is —$CH_2$—$CH_2$—O— or $CH_2$—$CH_2$—$CH_2$—.

19. The compound according to claim 13 wherein $R^3$ is 4-fluorophenyl, 4-chlorophenyl, 4-methoxyphenyl or 4-methylphenyl.

20. The compound according to claim 18 wherein $R^3$ is 4-fluorophenyl, 4-chlorophenyl, 4-methoxyphenyl or 4-methylphenyl.

21. The compound according to claim 13 wherein any carbocyclic group is phenyl.

22. The compound according to claim 13 wherein the biolabile ester-forming group is: ethyl, propyl, butyl isobutyl, cyclopentyl, benzyl, 1-(2,2-diethylbutyryloxy)ethyl, 2-ethylpropionloxymethyl, 1-(2-ethylpropionyloxy)ethyl, 1-(2,4-dimethylbenzoyloxy)ethyl, (1-benzoyloxy)benzyl, 1-(benzoyloxy)ethyl, 2-methyl-1-propionyloxypropyl, 2,4,6-trimethylbenzoyloxymethyl, 1-(2,4,6-trimethylbenzyloxy)ethyl, pivaloyloxymethyl, phenethyl, phenpropyl, 2,2,2-trifluoroethyl, 1-naphthyl, 2-naphthyl, 2,4-dimethylphenyl, 4-t-butylphenyl, 5-(4-methyl-1,3-dioxalynyl-2-onyl)methyl, N,N-diethylaminocarbonylmethyl or 5-indanyl.

23. The compound according to claim 13 wherein $R^4$ and $R^5$ are both hydrogen.

24. The compound according to claim 18 wherein $R^4$ and $R^5$ are both hydrogen.

25. The compound according to claim 20 wherein $R^4$ and $R^5$ are both hydrogen.

26. The compound according to claim 13 wherein
$R^1$ is $C_1$–$C_6$alkyl or $C_1$–$C_6$alkoxy$C_1$–$C_3$alkyl;
$R^2$ is hydrogen;
L is a three atom linkage selected from: —$CH_2$—O—$CH_2$—, $CH_2$—$CH_2$—O— and $CH_2$—$CH_2$—$CH_2$—, where the right hand side of the linkage is attached to $R^3$;
$R^3$ is phenyl which may be independently substituted by one or more groups selected from: $C_1$–$C_6$alkyl, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio and nitrile; and
$R^4$ and $R^5$ are either both hydrogen, or one of $R^4$ and $R^5$ is hydrogen and the other is a biolabile ester-forming group selected from:
i) $C_1$–$C_6$alkyl optionally substituted by hydroxy, oxo, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio, nitrile, carbocyclyl, carbocyclyloxy, alkylcarbonyloxy, carbocyclylcarbonyloxy, alkylcarbonylamino, or alkylaminocarbonyl, wherein any carbocyclyl group is optionally substituted by $C_1$–$C_6$alkyl, halo, halo$C_1$–$C_6$alkyl, $C_1$–$C_6$alkoxy, halo$C_1$–$C_6$alkoxy, $C_1$–$C_6$alkylthio, halo$C_1$–$C_6$-alkylthio or nitrile; or
ii) carbocyclyl optionally substituted by $C_1$–$C_6$alkyl, halo, halo$C_1$–$C_6$alkyl, $C_1$–$C_6$alkoxy, halo$C_1$–$C_6$alkoxy, $C_1$–$C_6$alkylthio, halo$C_1$–$C_6$alkylthio or nitrile.

27. The compound according to claim 13 wherein
$R^1$ is propyl or methoxyethyl;
$R^2$ is hydrogen;
L is —$CH_2$—$CH_2$—O— or $CH_2$—$CH_2$—$CH_2$—, where the right hand side of the linkage is attached to $R^3$;
$R^3$ is 4-fluorophenyl, 4-chlorophenyl, 4-methoxyphenyl or 4-methylphenyl; and
$R^4$ and $R^5$ are both hydrogen.

28. The compound according to claim 1 selected from:
(2S)-2-[(1-{[((1R)-2-carboxy-1-{[(2-chlorobenzyl)oxy]methyl}ethyl)-amino]carbonyl}cyclopentyl)methyl]-4-methoxybutanoic acid;

(3S)-3-[({1-[(2R)-2-carboxypentyl]cyclopentyl}carbonyl)amino]-5-(4-chlorophenoxy)pentanoic acid;

Ethyl (3S)-3-[({1-[(2S)-2-Carboxy-4-methoxybutyl]cyclopentyl}carbonyl)amino]-5-(4-chlorophenoxy)pentanoate;

(3S)-3-[({1-[(2S)-2-carboxy-4-methoxybutyl]cyclopentyl}carbonyl)amino]-5-(4-chlorophenoxy)pentanoic acid;

(2S)-2-({1-[({(1S)-3-butoxy-1-[2-(4-chlorophenoxy)ethyl]-3-oxopropyl}amino)carbonyl]cyclopentyl}methyl)-4-methoxybutanoic acid;

(3S)-3-[({1-[(2S)-2-carboxy-4-methoxybutyl]cyclopentyl}carbonyl)amino]-6-(4-chlorophenyl)hexanoic acid;

Ethyl (3S)-3-[({1-[(2S)-2-carboxy-4-methoxybutyl]cyclopentyl}-carbonyl)amino]-6-(4-chlorophenyl)hexanoate; and (3S)-3-[({1-[(2S)-2-carboxy-4-methoxybutyl]cyclopentyl}carbonyl)amino]-6-(4-methoxyphenyl)hexanoic acid.

29. The pharmaceutical composition comprising a compound defined in any one of claims 1 to 28, and a pharmaceutically acceptable salt thereof together with a pharmaceutically acceptable excipient, diluent or carrier.

30. A method of treating hypertension in a mammal with a therapeutically effective amount of a compound defined in any one of claims 1 to 28 and a pharmaceutically acceptable salt thereof.

* * * * *